US010233157B2

(12) United States Patent
Cohen et al.

(10) Patent No.: US 10,233,157 B2
(45) Date of Patent: *Mar. 19, 2019

(54) SIK INHIBITOR FOR USE IN A METHOD OF TREATING AN INFLAMMATORY AND/OR IMMUNE DISORDER

(71) Applicants: Dana-Farber Cancer Institute, Inc., Boston, MA (US); University Court of the University of Dundee, Dundee (GB)

(72) Inventors: Philip Cohen, Dundee (GB); Kristopher Clark, Dundee (GB); Hwan Geun Choi, Chestnut Hill, MA (US); Nathanael S. Gray, Boston, MA (US)

(73) Assignees: Dana-Farber Cancer Institute, Inc., Boston, MA (US); University Court of the University of Dundee, Dundee (GB)

(*) Notice: Subject to any disclaimer, the term of this patent is extended or adjusted under 35 U.S.C. 154(b) by 0 days.

This patent is subject to a terminal disclaimer.

(21) Appl. No.: 15/606,970

(22) Filed: May 26, 2017

(65) Prior Publication Data

US 2017/0342036 A1 Nov. 30, 2017
US 2018/0215719 A9 Aug. 2, 2018

Related U.S. Application Data

(62) Division of application No. 14/385,077, filed as application No. PCT/GB2013/050618 on Mar. 13, 2013, now Pat. No. 9,670,165.

(30) Foreign Application Priority Data

Mar. 13, 2012 (GB) .................... 1204384.0

(51) Int. Cl.
*A61K 31/506* (2006.01)
*C07D 239/48* (2006.01)
*C07D 403/12* (2006.01)
*A61K 31/519* (2006.01)
*A61K 31/5377* (2006.01)
*C07D 413/12* (2006.01)
*C07D 487/04* (2006.01)

(52) U.S. Cl.
CPC .......... *C07D 239/48* (2013.01); *A61K 31/506* (2013.01); *A61K 31/519* (2013.01); *A61K 31/5377* (2013.01); *C07D 403/12* (2013.01); *C07D 413/12* (2013.01); *C07D 487/04* (2013.01)

(58) Field of Classification Search
CPC .. A61K 31/505; A61K 31/506; C07D 239/48; C07D 403/12; C07D 487/04
USPC ...... 514/235.8, 252.14, 265.1; 544/122, 280, 544/295
See application file for complete search history.

(56) References Cited

U.S. PATENT DOCUMENTS

| 6,217,875 | B1 | 4/2001 | Murai et al. |
| 7,312,225 | B2 | 12/2007 | Luecking et al. |
| 9,586,936 | B2 | 3/2017 | Sim et al. |
| 9,670,165 | B2 | 6/2017 | Cohen et al. |
| 9,783,504 | B2 | 10/2017 | Gray et al. |
| 2004/0204427 | A1 | 10/2004 | Chen et al. |
| 2005/0026914 | A1* | 2/2005 | Buchanan ............. C04B 35/632 514/227.5 |
| 2006/0258687 | A1 | 11/2006 | Boehm et al. |
| 2007/0225286 | A1 | 9/2007 | Ren et al. |
| 2008/0249079 | A1* | 10/2008 | Chen .................... C07D 239/48 514/210.18 |
| 2009/0137804 | A1 | 5/2009 | Ding et al. |
| 2010/0056524 | A1* | 3/2010 | Mciver ................ C07D 239/48 514/235.8 |
| 2011/0086858 | A1 | 4/2011 | Wang et al. |
| 2011/0207711 | A1* | 8/2011 | Katz .................... A61K 31/535 514/210.16 |
| 2017/0204082 | A1 | 7/2017 | Gray et al. |
| 2017/0204116 | A1 | 7/2017 | Gray et al. |
| 2017/0224700 | A1 | 8/2017 | Shamji et al. |

FOREIGN PATENT DOCUMENTS

| CN | 104 482 860 A | 4/2015 |
| EP | 1 544 295 A1 | 6/2005 |
| EP | 2 746 283 A1 | 6/2014 |
| WO | WO 2000/024744 A1 | 5/2000 |
| WO | WO 2004/041821 A1 | 5/2004 |
| WO | WO 2004/041822 A1 | 5/2004 |
| WO | WO 2004/048343 A1 | 6/2004 |
| WO | WO 2005/009443 A1 | 2/2005 |

(Continued)

OTHER PUBLICATIONS

Takemori et al., Inactivation of HDAC5 by SIK1 in AICAR-treated C2C12 Myoblasts, Endocrine Journal, 56(1), 121-130 (2009).*
Liu et al., Salt-Inducible Kinase Is Involved in the Regulation of Corticotropin-Releasing Hormone Transcription in Hypothalamic Neurons in Rats, Endocrinology, 153(1), pp. 223-233 (Jan. 2012).*

(Continued)

*Primary Examiner* — Deepak R Rao

(74) *Attorney, Agent, or Firm* — Wolf, Greenfield & Sacks, P.C.

(57) ABSTRACT

The present invention relates to the discovery that salt inducible kinases (SIKs) suppress the formation of anti-inflammatory molecules such as IL-10, which are important for the resolution of inflammation and identifies SIK inhibitors that may be used to treat disorders associated with undesirable inflammation, such as inflammatory bowel disease and/or autoimmune disorders.

26 Claims, 15 Drawing Sheets

Specification includes a Sequence Listing.

(56) References Cited

FOREIGN PATENT DOCUMENTS

| | | | |
|---|---|---|---|
| WO | WO 2005/009978 A1 | 2/2005 | |
| WO | WO 2005/011597 A2 | 2/2005 | |
| WO | WO 2005/123719 A1 | 12/2005 | |
| WO | WO 2006/000420 A1 | 1/2006 | |
| WO | WO 2006/024545 A1 | 3/2006 | |
| WO | WO 2007/071752 A2 | 6/2007 | |
| WO | WO 2007/136465 A2 | 11/2007 | |
| WO | WO 2008/060248 A1 | 5/2008 | |
| WO | WO 2009/122180 A1 | 10/2009 | |
| WO | WO 2009/152027 | * | 12/2009 |
| WO | WO 2009/152027 A1 | 12/2009 | |
| WO | WO 2013/045653 A1 | 4/2013 | |
| WO | WO 2013/074986 A1 | 5/2013 | |
| WO | WO 2013/136070 A1 | 9/2013 | |
| WO | WO 2014/144737 A1 | 9/2014 | |
| WO | WO 2015/006492 A1 | 1/2015 | |
| WO | WO 2016/014542 A1 | 1/2016 | |
| WO | WO 2016/014551 A1 | 1/2016 | |
| WO | WO 2016/023014 A2 | 2/2016 | |

OTHER PUBLICATIONS

Invitation to Pay Additional Fees for PCT/US2017/040722, dated Oct. 18, 2017.
International Search Report and Written Opinion for PCT/US2017/040722, dated Dec. 12, 2017.
Extended European Search Report for EP 15824907.8, dated Jan. 2, 2018.
Invitation to Pay Additional Fees for PCT/US2015/041360 dated Sep. 24, 2015.
International Search Report and Written Opinion for PCT/US2015/041360 dated Dec. 15, 2015.
International Preliminary Report on Patentability for PCT/US2015/041360 dated Feb. 2, 2017.
Extended European Search Report for EP 15824975.5, dated Nov. 27, 2017.
International Search Report and Written Opinion for PCT/US2015/41348 dated Oct. 28, 2015.
International Preliminary Report on Patentability for PCT/US2015/41348 dated Feb. 2, 2017.
Partial Supplementary European Search Report for EP 15829427.2, dated Feb. 8, 2018.
Invitation to Pay Additional Fees for PCT/US2015/044387, dated Jan. 28, 2016.
International Search Report and Written Opinion for PCT/US2015/044387, dated Mar. 25, 2016.
International Preliminary Report on Patentability for PCT/US2015/044387, dated Feb. 23, 2017.
International Preliminary Report on Patentability for PCT/GB2013/050618, dated Sep. 25, 2014.
International Search Report and Written Opinion for PCT/GB2013/050618, dated May 17, 2013.
Altarejos et al., CREB and the CRTC co-activators: sensors for hormonal and metabolic signals. Nat Rev Mol Cell Biol. Mar. 2011;12(3):141-51. doi: 10.1038/nrm3072.
Antiga et al., Serum levels of the regulatory cytokines transforming growth factor-β and interleukin-10 are reduced in patients with discoid lupus erythematosus. Lupus. May 2011;20(6):556-60. doi: 10.1177/0961203310392424. Epub Mar. 3, 2011.
Bain et al., The selectivity of protein kinase inhibitors: a further update. Biochem J. Dec. 15, 2007;408(3):297-315.
Benoit et al., Macrophage polarization in bacterial infections. J Immunol. Sep. 2008 15;181(6):3733-9.
Berdesux et al., SIK1 is a class II HDAC kinase that promotes survival of skeletal myocytes. Nat Med. May 2007;13(5):597-603. Epub Apr. 29, 2007.
Bettencourt-Dias et al., Genome-wide survey of protein kinases required for cell cycle progression. Nature. Dec. 23, 2004;432(7020):980-7.

Clark et al., Phosphorylation of CRTC3 by the salt-inducible kinases controls the interconversion of classically activated and regulatory macrophages. Proc Natl Acad Sci U S A. Oct. 16, 2012;109(42):16986-91. doi: 10.1073/pnas.1215450109. Epub Oct. 2, 2012. With Supporting Information.
Eyers et al., Conversion of SB 203580-insensitive MAP kinase family members to drug-sensitive forms by a single amino-acid substitution. Chem Biol. Jun. 1998;5(6):321-8.
Fleming et al., Regulatory macrophages: setting the threshold for therapy. Eur J Immunol. Sep. 2011;41(9):2498-502. doi: 10.1002/eji.201141717.
Fraser et al., Dasatinib inhibits the secretion of TNF-alpha following TLR stimulation in vitro and in vivo. Exp Hematol. Dec. 2009;37(12):1435-44. doi: 10.1016/j.exphem.2009.09.007. Epub Sep. 26, 2009.
Fu et al., Parathyroid hormone controls receptor activator of NF-kappaB ligand gene expression via a distant transcriptional enhancer. Mol Cell Biol. Sep. 2006;26(17):6453-68.
Fu et al., Parathyroid hormone stimulates receptor activator of NFkappa B ligand and inhibits osteoprotegerin expression via protein kinase a activation of cAMP-response element-binding protein. J Biol Chem. Dec. 13, 2002;277(50):48868-75. Epub Oct 2, 2002.
Hahn et al., Targeted therapies in systemic lupus erythematosus: successes, failures and future. Ann Rheum Dis. Mar. 2011;70 Suppl 1:i64-i66. doi: 10.1136/ard.2010.142208.
Hart et al., SB1518, a novel macrocyclic pyrimidine-based JAK2 inhibitor for the treatment of myeloid and lymphoid malignancies. Leukemia. Nov. 2011;25(11):1751-9. doi: 10.1038/leu.2011.148. Epub Jun. 21, 2011.
Henriksson et al., SIK2 regulates CRTCs, HDAC4 and glucose uptake in adipocytes. J Cell Sci. Feb. 1, 2015;128(3):472-86.
Henriksson et al., The AMPK-related kinase SIK2 is regulated by cAMP via phosphorylation at Ser358 in adipocytes. Biochem J. Jun. 15, 2012;444(3):503-14. doi: 10.1042/BJ20111932.
Heppner et al., Immune attack: the role of inflammation in Alzheimer disease. Nat Rev Neurosci. Jun. 2015;16(6):358-72. doi: 10.1038/nrn3880.
Horike et al., Downregulation of SIK2 expression promotes the melanogenic program in mice. Pigment Cell Melanoma Res. Dec. 2010;23(6):809-19. doi: 10.1111/j.1755-148X.2010.00760.x. Epub Aug. 31, 2010.
Jansson et al., Glucose controls CREB activity in islet cells via regulated phosphorylation of TORC2. Proc Natl Acad Sci U S A. Jul. 22, 2008;105(29):10161-6. doi: 10.1073/pnas.0800796105. Epub Jul. 14, 2008.
Kantarjian et al., Dasatinib versus imatinib in newly diagnosed chronic-phase chronic myeloid leukemia. N Engl J Med. Jun. 17, 2010;362(24):2260-70.
Kopf et al., Averting inflammation by targeting the cytokine environment. Nat Rev Drug Discov. Sep. 2010;9(9):703-18. doi: 10.1038/nrd2805.
Kuhn et al., Interleukin-10-deficient mice develop chronic enterocolitis. Cell. Oct. 22, 1993;75(2):263-74.
Kumagai et al., A potent inhibitor of SIK2, 3, 3', 7-trihydroxy-4'-methoxyflavon (4'-O-methylfisetin), promotes melanogenesis in B16F10 melanoma cells. PLoS One. 2011;6(10):e26148. doi: 10.1371/journal.pone.0026148. Epub Oct. 13, 2011.
Liu et al., Engineering Src family protein kinases with unnatural nucleotide specificity. Chem Biol. Feb. 1998;5(2):91-101.
Liu et al., Salt-inducible kinase is involved in the regulation of corticotropin-releasing hormone transcription in hypothalamic neurons in rats. Endocrinology. Jan. 2012;153(1):223-33. doi: 10.1210/en.2011-1404. Epub Nov. 22, 2011.
Maier et al., Development of N-4,6-pyrimidine-N-alkyl-N'-phenyl ureas as orally active inhibitors of lymphocyte specific tyrosine kinase. Bioorg Med Chem Lett. Jul. 15, 2006;16(14):3646-50. Epub May 8, 2006.
Mair et al., Lifespan extension induced by AMPK and calcineurin is mediated by CRTC-1 and CREB. Nature. Feb 17, 2011;470(7334):404-8. doi: 10.1038/nature09706.
Mallinson et al., Macrocycles in new drug discovery. Future Med Chem. Jul. 2012;4(11):1409-38. doi: 10.4155/fmc.12.93.

(56) References Cited

OTHER PUBLICATIONS

Martin et al., Novel 2-aminopyrimidine carbamates as potent and orally active inhibitors of Lck: synthesis, SAR, and in vivo antiinflammatory activity. J Med Chem. Aug. 10, 2006;49(16):4981-91.

McWhirter et al., IFN-regulatory factor 3-dependent gene expression is defective in Tbk1-deficient mouse embryonic fibroblasts. Proc Natl Acad Sci U S A. Jan. 6, 2004;101(1):233-8. Epub Dec. 16, 2003.

Mosser et al., Interleukin-10: new perspectives on an old cytokine. Immunol Rev. Dec. 2008;226:205-18. doi: 10.1111/j.1600-065X.2008.00706.x.

O'Garra et al., Strategies for use of IL-10 or its antagonists in human disease. Immunol Rev. Jun. 2008;223:114-31. doi: 10.1111/j.1600-065X.2008.00635.x.

Park et al., SIK2 is critical in the regulation of lipid homeostasis and adipogenesis in vivo. Diabetes. Nov. 2014;63(11):3659-73. doi: 10.2337/db13-1423. Epub Jun. 4, 2014.

Patel et al., The LKB1-salt-inducible kinase pathway functions as a key gluconeogenic suppressor in the liver. Nat Commun. Aug. 4, 2014;5:4535. doi: 10.1038/ncomms5535.

Pethe et al., A chemical genetic screen in Mycobacterium tuberculosis identifies carbon-source-dependent growth inhibitors devoid of in vivo efficacy. Nature Communications 2010;1:57. doi:10.1038/ncomms1060.

Popov et al., Lack of salt-inducible kinase 2 (SIK2) prevents the development of cardiac hypertrophy in response to chronic high-salt intake. PLoS One. Apr. 21, 2014;9(4):e95771. doi: 10.1371/journal.pone.0095771. eCollection 2014.

Sakamaki et al., Role of the SIK2-p35-PJA2 complex in pancreatic β-cell functional compensation. Nat Cell Biol. Mar. 2014;16(3):234-44. doi: 10.1038/ncb2919.

Saraiva et al., The regulation of IL-10 production by immune cells. Nat Rev Immunol. Mar. 2010;10(3):170-81. doi: 10.1038/nri2711. Epub Feb. 15, 2010.

Sasagawa et al., SIK3 is essential for chondrocyte hypertrophy during skeletal development in mice. Development. Mar. 2012;139(6):1153-63. doi: 10.1242/dev.072652. Epub Feb. 8, 2012.

Sasaki et al., SIK2 is a key regulator for neuronal survival after ischemia via TORC1-CREB. Neuron. Jan. 13, 2011;69(1):106-19. doi: 10.1016/j.neuron.2010.12.004.

Screaton et al., The CREB coactivator TORC2 functions as a calcium- and cAMP-sensitive coincidence detector. Cell. Oct. 1, 2004;119(1):61-74.

Sundberg et al., Development of Chemical Probes for Investigation of Salt-Inducible Kinase Function in Vivo. ACS Chem Biol. Aug. 19, 2016;11(8):2105-11. doi: 10.1021/acschembio.6b00217. Epub Jun. 6, 2016.

Sundberg et al., Small-molecule screening identifies inhibition of salt-inducible kinases as a therapeutic strategy to enhance immunoregulatory functions of dendritic cells. Proc Natl Acad Sci U S A. Aug. 26, 2014;111(34):12468-73. doi: 10.1073/pnas.1412308111. Epub Aug. 11, 2014.

Takemori et al., Inactivation of HDAC5 by SIK1 in AICAR-treated C2C12 myoblasts. Endocr J. 2009;56(1):121-30. Epub Oct. 22, 2008.

Triantafillidis et al., Current and emerging drugs for the treatment of inflammatory bowel disease. Drug Des Devel Ther. Apr. 6, 2011;5:185-210. doi: 10.2147/DDDT.S11290.

Walkinshaw et al., The tumor suppressor kinase LKB1 activates the downstream kinases SIK2 and SIK3 to stimulate nuclear export of class IIa histone deacetylases. J Biol Chem. Mar. 29, 2013;288(13):9345-62. doi: 10.1074/jbc.M113.456996. Epub Feb. 7, 2013.

Wang et al. Cloning of a novel kinase (SIK) of the SNF1/AMPK family from high salt diet-treated rat adrenal. FEBS Lett. Jun. 18, 1999;453(1-2):135-9.

Wu et al., Exploring the selectivity of PI3Kα and mTOR inhibitors by 3D-QSAR, molecular dynamics simulations and MM/GBSA binding free energy decomposition. Med. Chem. Commun., 2013;4:1482-1496. DOI: 10.1039/C3MD00157A.

Yahara et al., Pterosin B prevents chondrocyte hypertrophy and osteoarthritis in mice by inhibiting Sik3. Nat Commun. Mar. 24, 2016;7:10959. doi: 10.1038/ncomms10959.

* cited by examiner

Figure 1A
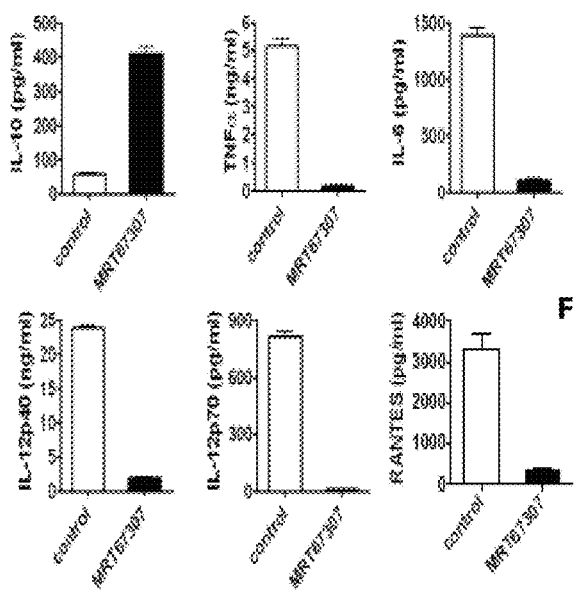
Figure 1B
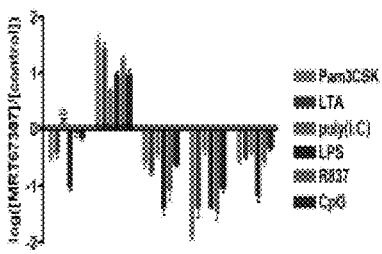
Figure 1C
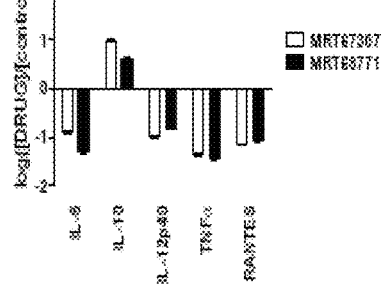
Figure 1D
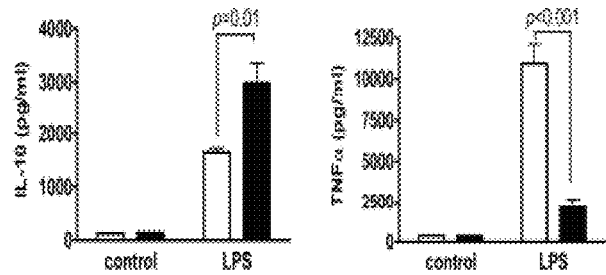
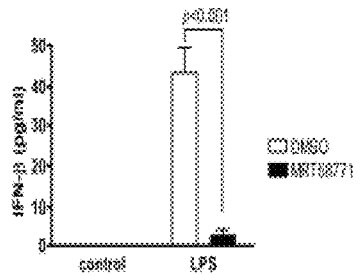

Figure 4A
| | MRT67307 | MRT199665 | KIN112 |
|---|---|---|---|
| AMPKα1/α2 | 810 | 10 | >10000 |
| MARK1 | 27 | 2 | >10000 |
| MARK2 | 52 | 2 | >10000 |
| MARK3 | 36 | 3 | >10000 |
| MARK4 | 41 | 2 | >10000 |
| SIK1 | 250 | 110 | 10 |
| SIK2 | 67 | 12 | 22 |
| SIK3 | 430 | 43 | 60 |
| NUAK1 | 230 | 3 | >10000 |
| NUAK2 | 2600 | 120 | 2100 |
| BRSK1 | >10000 | >10000 | >10000 |
| BRSK2 | 10000 | 10000 | >10000 |
| MELK | 900 | 29 | 2000 |
| TBK1 | 19 | 5400 | >10000 |
| IKKε | 160 | 7700 | >10000 |
Figure 4B
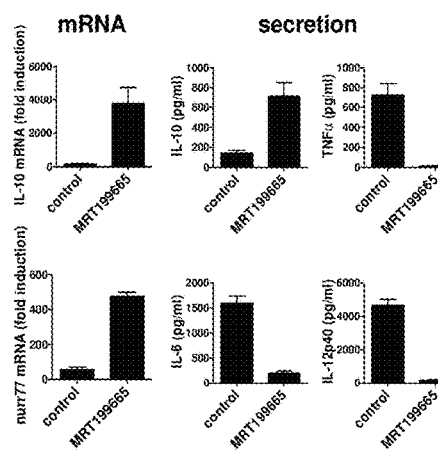
Figure 4C
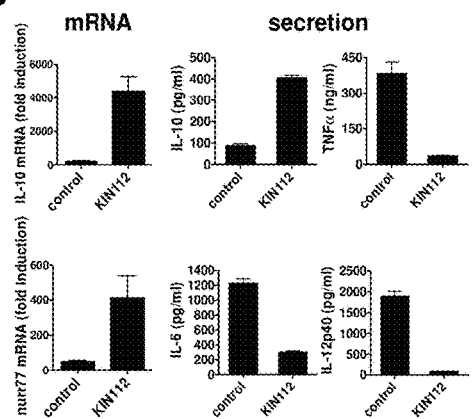
Figure 4D
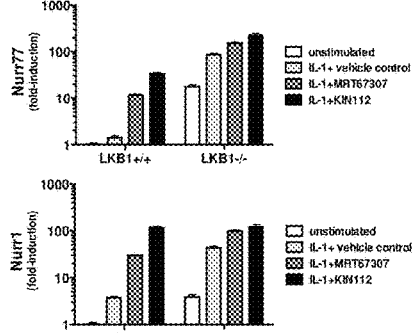
Figure 4E
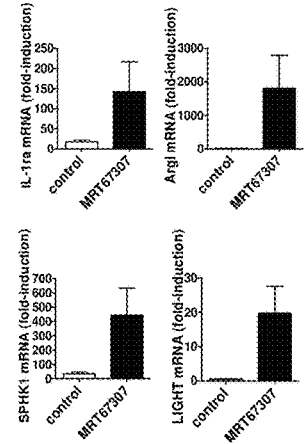

Figure 9F

MRT67307

MRT199665

KIN112

HG-9-91-01

Figure 12A
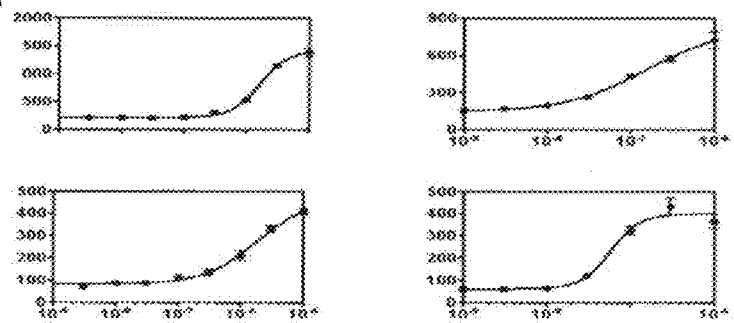
Figure 12B
Figure 12C
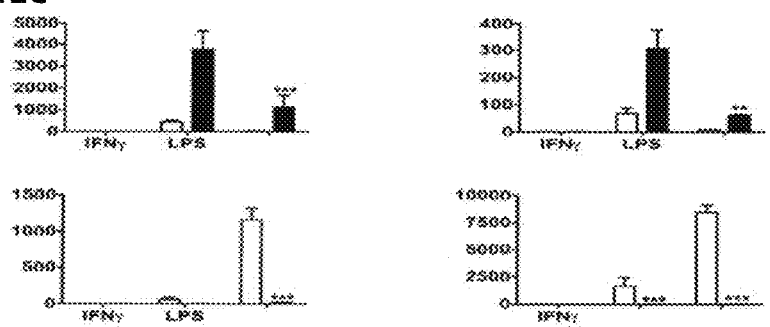
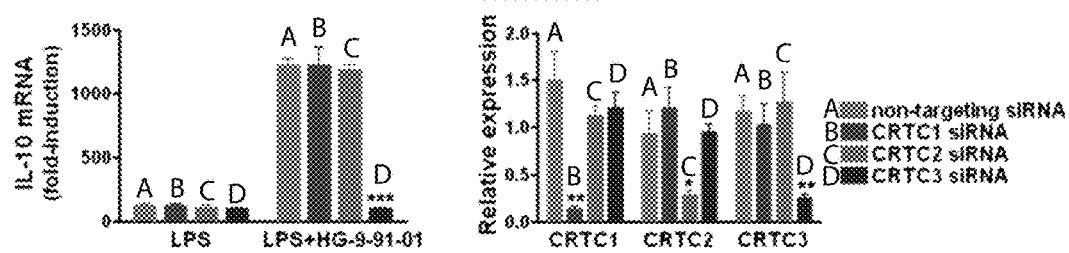

SIK INHIBITOR FOR USE IN A METHOD OF TREATING AN INFLAMMATORY AND/OR IMMUNE DISORDER

CROSS REFERENCE TO RELATED APPLICATIONS

This application is a divisional of and claims priority under 35 U.S.C. § 120 to U.S. patent application Ser. No. 14/385,077, filed Sep. 12, 2014 and issued as U.S. Pat. No. 9,670,165, which is a national stage application under 35 U.S.C. § 371 of international PCT application, PCT/GB2013/050618, filed on Mar. 13, 2013, which claims priority to and the benefit of United Kingdom patent application, GB 1204384.0, filed Mar. 13, 2012, the contents of each of which are incorporated herein by reference in their entireties.

FIELD OF THE INVENTION

The present invention relates to the discovery that salt inducible kinases (SIKs) suppress the formation of anti-inflammatory molecules such as IL-10, which are important for the resolution of inflammation and identifies SIK inhibitors that may be used to treat disorders associated with undesirable inflammation, such as inflammatory bowel disease and/or autoimmune disorders.

BACKGROUND TO THE INVENTION

Inflammatory Bowel Disease. (IBD) is a chronic, relapsing inflammatory disorder of the GI tract. It is caused by inappropriate and chronic activation of the innate immune system in the gut. Patients show elevated levels of pro-inflammatory cytokines including IL-12, IL-18, TNFα, IFNγ, IL-2, IL-1, IL-6 and IL-8. The most common forms of IBD are Crohn's Disease (CD) and Ulcerative Colitis (UC). Symptoms associated with these conditions include abdominal pain, vomiting, diarrhea, rectal bleeding, severe internal pelvic cramps and weight loss. These symptoms can severely restrict quality of life. In addition, complications of the disease can lead to bowel rupture, bleeding from deep ulcerations, intestinal blockages and fistulae, secondary infections and increased risk of colon cancer.

Estimates suggest that the global prevalence rate of IBD is as much as 396 people per 100,000. In the USA IBD is one of the five most prevalent gastrointestinal disease burdens with as many as 1.4 million sufferers leading to healthcare costs of more than $1.7 billion. Each year in the United States, IBD accounts for more than 700,000 physician visits, 100,000 hospitalizations, and disability in 119,000 patients (Centre for Disease Control and Prevention website).

IBD is a chronic condition and there is no pharmacological cure. Patients usually require treatment for symptomatic relief throughout their lifetime and over the long term up to 75% of patients with Crohn's disease and 25% of those with ulcerative colitis will require surgery.

The aim of current treatment strategies is to induce remission after which the patient can be switched to a lighter treatment regime with fewer side effects until the next flare up occurs.

The drugs commonly used to induce remission and alleviate the symptoms of IBD are antiinflammatories (aminosalicylates (5-ASA, mesalazine), steroids, immunosuppressors (azathioprine, 6-MP, and methotrexate), antibiotics (metronidazole, ampicillin, ciprofloxin, others), and anti-TNF biologics (inflixamab, humira). Surgery becomes necessary when medications can no longer control the symptoms. Ulcerative colitis can be effectively cured after removal of the colon (colectomy), but Crohn's disease can recur after surgery.

Macrophages express Toll-Like Receptors (TLRs) that detect core components of pathogens, triggering the activation of signaling pathways that lead to the production of inflammatory mediators needed to combat infection[1]. However this defence system is a double-edged sword because failure to resolve inflammation can cause chronic inflammatory diseases and/or autoimmune disorders, such as rheumatoid arthritis and systemic lupus erythematosus[1-3]. Regulatory macrophages that produce high levels of anti-inflammatory molecules, such as interleukin (IL)-10, and low levels of pro-inflammatory cytokines, like IL-12, are thought to be crucial for the resolution of inflammatory responses[4]. A central problem in this area is therefore to understand how to promote the formation of regulatory macrophages at sites of inflammation.

SIKs (Salt Induced Kinases) are serine threonine kinases of the AMPK-related kinase family. SIK1 was first cloned in 1999 as a kinase that was upregulated in the adrenal glands of rats in response to a high salt diet (Wang et al, FEBS Lett 1999). Since then two other isoforms SIK2 and SIK3 have been identified. SIK1 is expressed at high levels in the adrenal gland and also in the brain, pituitary, ovary, testis and lung. SIK2 is expressed in white and brown adipose tissue and SIK3 is ubiquitous. SIK1 is best characterized as mediating repression of steroidogenic genes by inhibiting CRTC-CREB-dependent transcription. SIK2 is best characterized as regulating gluconeogenesis under conditions of fasting. Increases in circulating glucagon promote PKA-dependent inhibition of SIK2, which leads to CRTC2 activation and CRTC2-CREB dependent induction of gluconeogenesis genes. Normally SIK2 is maintained in an active state in response to insulin-AKT-dependent regulation.

The physiological role of SIK3(QSK) remains unclear although it may play a role in cell proliferation based on the finding that the *drosophila* KO shows spindle defects and chromosomal abnormalities (M. Bettencourt-Dias, R. Giet, R. Sinka, A. Mazumdar, W. G. Lock, F. Balloux, P. J. Zafiropoulos, S. Yamaguchi, S. Winter, R. W. Carthew, M. Cooper, D. Jones, L. Frenz & D. M. Glover Nature 432, 980-987 (2004) Genome-wide survey of protein kinases required for cell cycle)

SUMMARY OF THE INVENTION

The present invention is based on a new discovery that inhibition of SIK in macrophages, resulted in development of the macrophages to a regulatory macrophage phenotype, which have previously been shown to be associated with controlling inflammation and/or autoimmune responses.

Thus, in a first aspect there is provided a SIK inhibitor for use in a method of treating an inflammatory and/or autoimmune disorder.

"Inflammation" "Inflammatory" or "inflammatory response" refers to both acute responses (i.e., responses in which the inflammatory processes are active) and chronic responses (i.e., responses marked by slow progression and optionally formation of new connective tissue). Acute and chronic inflammation can be distinguished by the cell types involved. Acute inflammation often involves polymorphonuclear neutrophils; whereas chronic inflammation is normally characterized by a lymphohistiocytic and/or granulomatous response. Inflammation includes reactions of both the specific and non-specific defence systems. A specific defence system reaction is a specific immune system reaction response to an antigen (possibly including an autoantigen). A non-specific defence system reaction is an inflammatory response mediated by leukocytes incapable of immunological memory. Such cells include granulocytes, macrophages, neutrophils and eosinophils. Examples of specific types of inflammation are diffuse inflammation, focal inflammation, croupous inflammation, interstitial inflammation, obliterative inflammation, parenchymatous inflammation, reactive inflammation, specific inflammation, toxic inflammation and traumatic inflammation. All such types of inflammation may be encompassed within the present invention, providing that the inflammatory response is associated with an effect caused by SIK expression/activity. However, in a preferred embodiment, the control of inflammation is mediated by the formation of regulatory macrophages, which are macrophages which are characterised by high levels of IL-10 secretion and lower levels of pro-inflammatory cytokines, such as IL-1, IL-6, TNFα and TGFβ.

Inflammatory Conditions which may be treated or prevented include inflammatory bowel diseases: Inflammatory bowel diseases, include Crohn's disease and ulcerative colitis, which involves autoimmune attack of the bowel. These diseases cause chronic diarrhea, frequently bloody, as well as symptoms of colonic dysfunction. Other inflammatory conditions/disease include peripheral inflammation, acute inflammation, chronic inflammation, arthritis, or rheumatoid arthritis, bone resorption, graft vs. host reaction, atherosclerosis, osteoarthritis, gout, psoriasis, topical inflammatory disorder state, adult respiratory distress syndrome, asthma, chronic pulmonary inflammatory disorder, cardiac reperfusion injury, renal reperfusion injury, thrombus, glomerulonephritis, or cachexia, inflammation associated with wound treatment.

As well as treating/preventing inflammation, the present invention may find application in treating autoimmune disease, examples of autoimmune diseases include those involving the thyroid (Grave's disease and Hashimoto's thyroiditis), peripheral nerves (Guillain-Barre Syndrome and other autoimmune peripheral neuropathies), the CNS (acute disseminated encephalomyelitis, ADEM), the skin (pemphigoid (bullous), pemphigus foliaceus, pemphigus vulgaris, coeliac sprue-dermatitis, vitiligo), the liver and gastrointestinal system (primary biliary cirrhosis, pernicious anemia, autoimmune hepatitis), and the eye (autoimmune uveitis). There are also multiple "autoimmune rheumatic diseases" (Sjogren's syndrome, discoid lupus, antiphospholipid syndrome, CREST, mixed connective tissue disease (MCTD), polymyositis and dermatomyositis, and Wegener's granulomatosus).

The present compositions and methods provide a novel approach to treating autoimmune and inflammatory diseases using SIK inhibitors.

The present invention also encompasses a method for preventing or treating an inflammatory and/or autoimmune condition/disease in a mammal comprising administering a SIK inhibitor in a therapeutic amount to a mammal in need thereof.

"Treat" or "treating" means any treatment, includes, but is not limited to, alleviating symptoms of a disease, disorder, or condition, eliminating the causation of a disease, disorder, or condition on either a temporary or permanent basis; or slowing, reducing, or inhibiting an ongoing pathological process in an asymptomatic individual. In such an asymptomatic individual, the pathological process would likely eventually cause symptoms.

"Preventing" refers to inhibiting the initial onset of a pathologic process, such that the pathologic process that could eventually lead to development of symptoms never develops (i.e., preventing the development of a disease, disorder, or condition in a prophylactic manner).

"Therapeutically effective amount" means an amount of a compound that is effective in treating or preventing a particular disorder or condition.

"Pharmaceutically acceptable carrier" is a nontoxic solvent, dispersant, excipient, or other material used in formation of a pharmaceutical composition, i.e., a dosage form capable of administration to a subject or patient.

The term SIK includes, but is not limited to SIK1, SIK2 and/or SIK3. The compounds of the present invention may be specific to one form of SIK or active against more than one form, e.g. two or all three known forms.

"Inhibitor" includes, but is not limited to, any suitable small molecule, compound, protein or fragment thereof, nucleic acid, formulation or substance that can inhibit SIK activity. According to the present invention, it is contemplated that the inhibitor can exhibit its regulatory effect upstream or downstream of SIK or on SIK directly. Examples of inhibitor regulated SIK activity include those where the inhibitor can decrease transcription and/or translation of SIK, can decrease or inhibit post-translational modification and/or cellular trafficking of SIK, or can shorten the half life of SIK. The inhibitor can also reversibly or irreversibly bind SIK, inactivate its enzymatic activity, or otherwise interfere with its interaction with downstream substrates The SIK inhibitor can be, for example, an antisense oligonucleotide to SIK, or for example, an interfering RNA to SIK. Inhibitors include agents that, e.g., alter the interaction of SIK with proteins that bind activators, or inhibitors, or receptors, SIK inhibitors may include proteins, antibodies and fragments thereof, peptides, lipids, carbohydrates, polysaccharides, or combinations of the above, e.g., lipoproteins, glycoproteins, and the like; genetically modified versions of naturally-occurring SIK ligands, e.g., with altered activity, as well as naturally occurring and synthetic ligands, antagonists, small chemical molecules and the like.

"Antagonist" is used in the broadest sense, and includes any molecule that partially or fully blocks, inhibits, or neutralizes a biological activity of a SIK polypeptide. Suitable antagonist molecules specifically include antagonist antibodies or antibody fragments, fragments or amino acid sequence variants of native SIK polypeptides, peptides, antisense oligonucleotides, small organic molecules, and the like. Methods for identifying antagonists of a SIK polypeptide can comprise contacting a SIK polypeptide with a candidate antagonist molecule and measuring a detectable change in one or more biological activities normally associated with the SIK polypeptide.

The skilled addressee is well aware of how to identify nucleic acid molecules, such as oligonucleotides and siRNA molecules which may inhibit SIK gene expression. Equally, the skilled addressee knows how to identify antibodies, both monoclonal and polyclonal antibodies, as well as fragments (e.g. Fc fragments) which may be of use in binding to SIK and therefore acting as an inhibitor.

Screens may be carried out to identify small molecules (typically less than 1000 Mn, or less than 500 Mn) which may act as SIK inhibitors as will be described in more detail herein. However, the present inventors have shown that five molecules MRT67307, MRT68771, MRT199665, KIN112 and HG-9-91-01 all possess SIK inhibitory activity and may be of use in the present invention, or as leads to develop further SIK inhibitors.

Thus, in a further aspect, the present invention provides a 2,4-diaminopyrimidine compound, having structure (X), in a method of treating an inflammatory and/or autoimmune disorder.

wherein
$Ar_1$ is a 5- or 6-membered hetero- or homo-cyclic aromatic ring optionally having a $C_1$-$C_4$ alkyl, or saturated heterocyclic or methyl-heterocyclic substituent;
$R_2$ is or $R_3$ is hydrogen or

;

and $R_4$ is hydrogen or where $R_5$ is H or a $C_1$-$C_4$ alkyl; or
$R_3$ and $R_4$ together form a pyrrolidine ring where one or both of the free carbons are substituted with an alkyl or oxygen-containing substituent. Preferably $R_4$ may be Preferably $Ar_1$ comprises a nitrogen atom which is an ε-N or a ζ-N to the C2 of the pyrimidine ring. Typically $Ar_1$ may comprises a benzene ring. Preferred $Ar_1$ groups are , or where X is a 5- or 6-membered alicyclic ring comprising up to one oxygen, such as wherein $Ar_1$ is or Preferably, when $R_2$ is $R_3$ and $R_4$ together form A preferred compound is (MRT199665)

Preferably,
Ar₁ may be

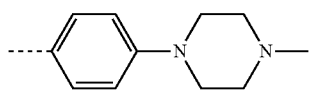

and
R₂ is

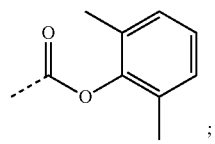
;

such that the 2,4-diaminopyrimidine compound has the structure;

(KIN112)

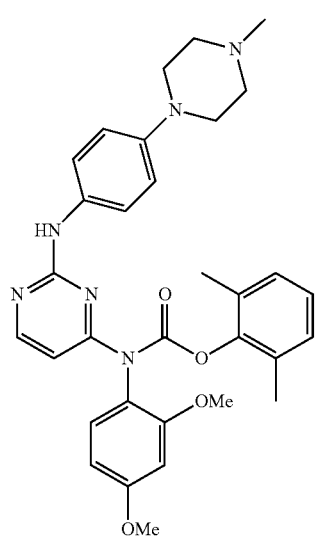

Preferably, R₂ is

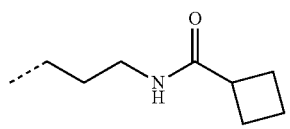

R₃ is

and Ar₁ is

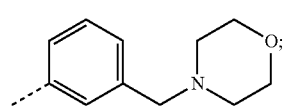
;

such that the 2,4-diaminopyrimidine compound has the structure;

(MRT67307)

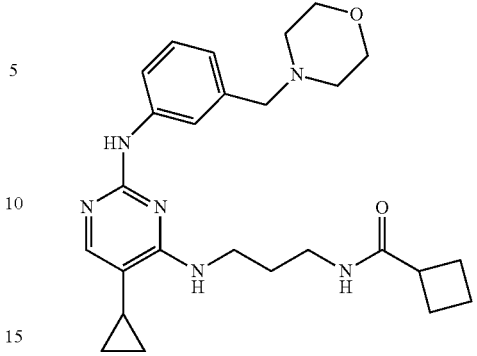

Preferably, R₂ may be

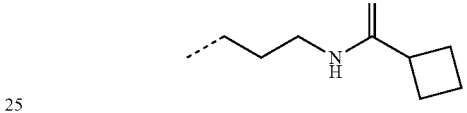

R₃ is

and Ar₁ is

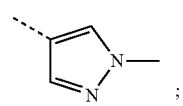
;

such that the 2,4-diaminopyrimidine compound has the structure;

(MRT68771)

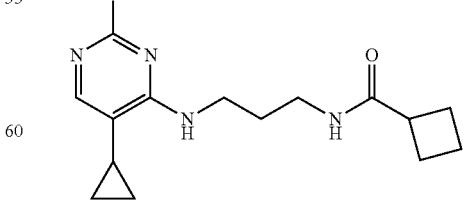

In a further aspect there is provided a compound of Formula (II) for use in a method of treating an inflammatory disorder and/or autoimmune disorder:

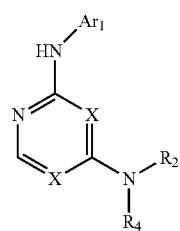
(II)

wherein Ar₁ is a 5- or 6-membered hetero- or homo-cyclic aromatic ring optionally having a $C_1$-$C_4$ alkyl, or saturated heterocyclic or methyl-heterocyclic substituent;

X is separately N or CH;

R₂ is

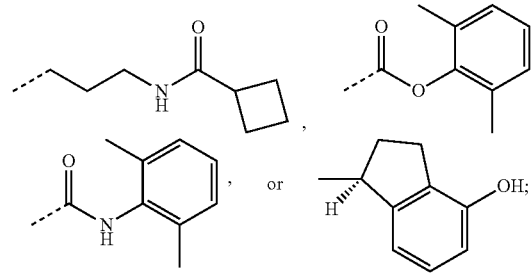

and
R₄ is hydrogen or

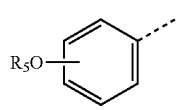
.

In a preferred embodiment Ar₁ is comprises a nitrogen atom which is an ε-N or a ζ-N to the C2 of the pyrimidine ring. Typically Ar₁ may comprises a benzene ring.

Preferred Ar₁ groups are

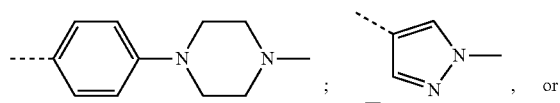

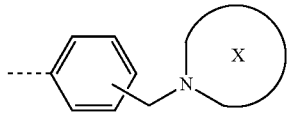

where X is a 5- or 6-membered alicyclic ring comprising up to one oxygen, such as wherein Ar₁ is

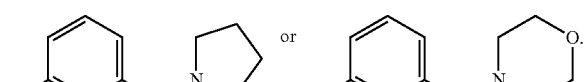

Preferably, when R₂ is

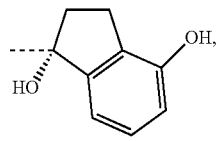

R₃ and R₄ together form

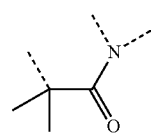

In one embodiment Ar₁ is

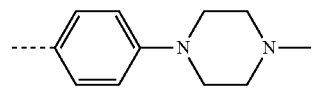

R₂ is

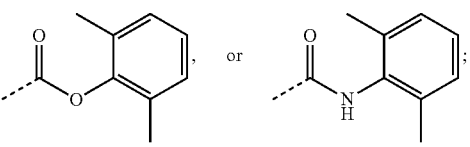

and R₄ is

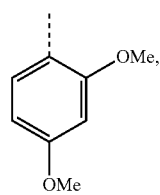

such that the compound may be KIN112 as previously defined or

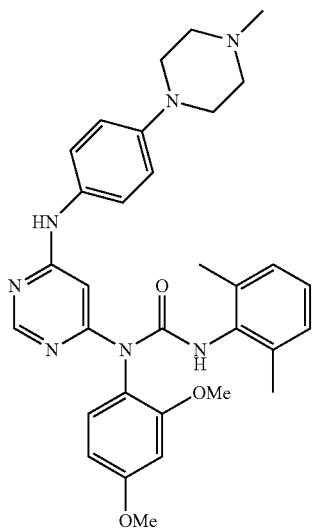

(HG-9-91-01)

In a further embodiment there is provided the compound HG-9-91-01 as defined above.

In a further embodiment there is provided a pharmaceutical formulation comprising the compound HG-9-91-01 together with a pharmaceutically acceptable excipient therefor. In a further embodiment there is provided the compound HG-9-91-01 for use in a method of therapy, such as in a method of treating inflammation and/or autoimmune disease.

All the compounds mentioned herein may also be present in an appropriate salt or solvate form, where appropriate.

The SIK inhibitors of the present invention may administered, for example, intravenously, parenterally, subcutaneously, intramuscularly, ophthalmically, intra-ventricularly, intraperitoneally, orally, or topically, to said mammal. In a further aspect, the SIK inhibitor may be administered in an encapsulated form, for example in a lipophilic compound or liposome. Such lipophilic compounds or liposomes may be modified as known in the art, to comprise targeting moieties designed to target the molecules to desired cells, such as macrophages.

Liposome Pharmaceutical Compositions

"Liposome" or "lipophilic compound" refer to unilamellar vesicles or multilamellar vesicles such as are described in U.S. Pat. No. 4,753,788 and U.S. Application No. 2004/0156889.

"Unilamellar liposomes," also referred to as "single lamellar vesicles," are spherical vesicles that includes one lipid bilayer membrane which defines a single closed aqueous compartment. The bilayer membrane includes two layers of lipids; an inner layer and an outer layer (leaflet). The outer layer of the lipid molecules are oriented with their hydrophilic head portions toward the external aqueous environment and their hydrophobic tails pointed downward toward the interior of the liposome. The inner layer of the lipid lays directly beneath the outer layer, the lipids are oriented with their heads facing the aqueous interior of the liposome and their tails toward the tails of the outer layer of lipid.

"Multilamellar liposomes," also referred to as "multilamellar vesicles" or "multiple lamellar vesicles," include more than one lipid bilayer membrane, which membranes define more than one closed aqueous compartment. The membranes are concentrically arranged so that the different membranes are separated by aqueous compartments, much like an onion.

"Encapsulation" and "entrapped" refer to the incorporation or association of the pharmaceutical agent in or with a liposome. The pharmaceutical agent may be associated with the lipid bilayer or present in the aqueous interior of the liposome, or both. In one embodiment, a portion of the encapsulated pharmaceutical agent takes the form of a precipitated salt in the interior of the liposome. The pharmaceutical agent may also self precipitate in the interior of the liposome.

"Excipient" "counterion" and "counterion excipient," refer to a substance that can initiate or facilitate drug loading and may also initiate or facilitate precipitation of the pharmaceutical agent in the aqueous interior of the liposome. Examples of excipients include, but are not limited to, the acid, sodium or ammonium forms of monovalent anions such as chloride, acetate, lactobionate and formate; divalent anions such as aspartate, succinate and sulfate; and trivalent ions such as citrate and phosphate. Preferred excipients include citrate and sulfate.

"Phospholipid" refers to any one phospholipid or combination of phospholipids capable of forming liposomes. Phosphatidylcholines (PC), including those obtained from egg, soy beans or other plant sources or those that are partially or wholly synthetic, or of variable lipid chain length and unsaturation are suitable for use in the present invention. Synthetic, semisynthetic and natural product phosphatidylcholines including, but not limited to, distearoylphosphatidylcholine (DSPC), hydrogenated soy phosphatidylcholine (HSPC), soy phosphatidylcholine (soy PC), egg phosphatidylcholine (egg PC), hydrogenated egg phosphatidylcholine (HEPC), dipalmitoylphosphatidylcholine (DPPC) and dimyristoylphosphatidylcholine (DMPC) are suitable phosphatidylcholines for use in this invention. All of these phospholipids are commercially available. Preferred PCs are HSPC and DSPC; the most preferred is HSPC. [0104] Further, phosphatidylglycerols (PG) andphosphatic acid (PA) are also suitable phospholipids for use in the present invention and include, but are not limited to, dimyristoylphosphatidylglycerol (DMPG), dilaurylphosphatidylglycerol (DLPG), dipalmitoylphosphatidylglycerol (DPPG), distearoylphosphatidylglycerol (DSPG) dimyristoylphosphatidic acid (DMPA), distearoylphosphatidic acid (DSPA), dilaurylphosphatidic acid (DLPA), and dipalmitoylphosphatidic acid (DPPA). Distearoylphosphatidylglycerol (DSPG) is the preferred negatively charged lipid when used in formulations. Other suitable phospholipids include phosphatidylethanolamines phosphatidylinositols, and phosphatidic acids containing lauric, myristic, stearoyl, and palmitic acidchains. Further, incorporation of polyethylene glycol (PEG) containing phospholipids is also contemplated by the present invention.

It is contemplated by this invention to optionally include cholesterol in the liposomal formulation. Cholesterol is known to improve liposome stability and prevent loss of phospholipid to lipoproteins in vivo.

Any suitable lipid:pharmaceutical agent ratio that is efficacious is contemplated by this invention. Preferred lipid:pharmaceutical agent molar ratios include about 5:1 to about 100:1, more preferably about 10:1 to about 40:1. The most preferred lipid:pharmaceutical agent molar ratios include about 15:1 to about 25:1. Preferred liposomal formulations include phospholipid:cholesterol molar ratios over the range of 1.5:0.5 to 2:1.5. Most preferred liposomal formulation is 2:1 PCxhol with or without 1 to 4 mole percent of a phosphatidylglycerol. The most preferred liposomal size is less than 100 nm. The preferred loading efficiency of pharmaceutical agent is a percent encapsulated pharmaceutical agent of about 70% or greater. Encapsulation includes molecules present in the interior aqueous space of the liposome, molecules in the inner or outer leaflet of the membrane bilayer, molecules partially buried in the outer leaflet of the bilayer and partially external to the liposome, and molecules associated with the surface of the liposome, e.g., by electrostatic interactions.

Generally, the process of preparing the formulation embodied in the present invention is initiated with the preparation of a solution from which the liposomes are formed. This is done, for example, by weighing out a quantity of a phosphatidylcholine optionally cholesterol and optionally a phosphatidylglycerol and dissolving them in an organic solvent, preferably chloroform and methanol in a 1:1 mixture (v/v) or alternatively neat chloroform. The solution is evaporated to form a solid lipid phase such as a film or a powder, for example, with a rotary evaporator, spray dryer or other means. The film or powder is then hydrated with an aqueous solution containing an excipient having a pH range from 2.0 to 7.4 to form a liposome dispersion. The preferred aqueous solution for purposes of hydration is a buffered solution of the acid, sodium or ammonium forms of citrate or sulfate. The preferred buffers are up to about 60 mM, citric acid (pH 2.0-5.0), ammonium citrate (pH 2.0-5.5), or ammonium sulfate (pH 2.0 to 5.5). It would be known by one of skill in the art that other anionic acid buffers could be used, such as phosphoric acid. The lipid film or powder dispersed in buffer is heated to a temperature from about 25° C. to about 70° C. depending on the phospholipids used.

The liposomes formed by the procedure of the present invention can be lyophilized or dehydrated in the presence of a hydrophilic agent.

Multilamellar liposomes are formed by agitation of the dispersion, preferably through the use of a thin-film evaporator apparatus such as is described in U.S. Pat. No. 4,935,171 or through shaking or vortex mixing. Unilamellar vesicles are formed by the application of a shearing force to an aqueous dispersion of the lipid solid phase, e.g., by sonication or the use of a microfluidizing apparatus such as a homogenizer or a French press. Shearing force can also be applied using either injection, freezing and thawing, dialyzing away a detergent solution from lipids, or other known methods used to prepare liposomes. The size of the liposomes can be controlled using a variety of known techniques including the duration of shearing force. Preferably, a homogenizing apparatus is employed to from unilamellar vesicles having diameters of less than 200 nanometers at a pressure of 3,000 to 14,000 psi preferably 10,000 to 14,000 psi, and a temperature of about the aggregate transition temperature of the lipids.

Drug loading via the pH gradient includes a low pH in the internal aqueous space of the liposomes, and this internal acidity is, by design, incompletely neutralized during the drug loading process. This residual internal acidity can cause chemical instability in the liposomal preparation (e.g., lipid hydrolysis), leading to limitations in shelf life. To quench this residual internal acidity, membrane permeable bases, such as amines (e.g., ammonium salts or alkyl-amines) can be added following the loading of the pharmaceutical agent in an amount sufficient to reduce the residual internal acidity to a minimum value (for example, pH at or above 4). Ammonium salts that can be used include ones having mono- or multivalent counterions, such as, but not limited to, ammonium sulfate, ammonium hydroxide ammonium acetate, ammonium chloride, ammonium phosphate, ammonium citrate, ammonium succinate, ammonium lactobionate, ammonium carbonate, ammonium tartrate, and ammonium oxalate. The analogous salt of any alkyl-amine compound which is membrane permeable can also be used, including, but not limited to, methylamine, ethylamine, diethylamine, ethylenediamine, and propylamine. During storage, for example at 2-8° C., the liposomal preparation will remain quenched, with reduced propensity for hydrolysis of either excipients or drug, relative to an un-quenched formulation. Upon injection, however, this quenching species rapidly leaks out of the liposome, thus restoring the residual gradient, which gradient is necessary for drug retention in vivo.

The therapeutic use of liposomes can include the delivery of drugs which are normally toxic in the free form. In the liposomal form, the toxic drug may be directed away from the sensitive tissue where toxicity can result and targeted to selected areas where they can exert their therapeutic effects. Liposomes can also be used therapeutically to release drugs slowly, over a prolonged period of time, thereby reducing the frequency of drug administration through an enhanced pharmacokinetic profile. In addition, liposomes can provide a method for forming an aqueous dispersion of hydrophobic drugs for intravenous delivery.

Biodegradable polyesters, such as poly(lactic acid) (PLA), poly(glycolic acid) (PGA), and poly(lactic-co-glycolic acid) (PLGA), have been extensively studied for a wide variety of pharmaceutical and biomedical applications. The biodegradable polyester family is a group of synthetic biodegradable polymers with controllable biodegradability, excellent biocompatibility, and high safety. The need for a variety of drug formulations for different drugs and delivery pathways has resulted in development of various types of block copolymers (e.g., diblock, triblock, multiblock, and starshaped block) consisting of the biodegradable polyesters and poly(ethylene glycol) (PEG). Studies have demonstrated many desirable, unique properties of PLGA-PEG block copolymers. Synthesis of PLGA-PEG block copolymers are useful in applications such as drug delivery vehicles, micro/nano-particles, micelles, hydrogels, and injectable delivery systems. (Akina, Inc., W. Lafayette, Ind., www.akinainc.com/polycelle)

In a further aspect the present invention provides a method of identifying SIK inhibitors for use in treating inflammation and/or autoimmune disease, the method comprising contacting a test agent with SIK protein or nucleic acid and detecting whether or not the test agent is able to inhibit SIK activity and/or gene expression.

Assays for inhibitors include, e.g., applying putative inhibitor compounds to a cell expressing SIK and then determining the functional effects on SIK signalling, as described herein. Samples or assays comprising SIK that are treated with a potential inhibitor, may be compared to control samples without the inhibitor, to examine the extent of inhibition. Control samples (untreated with inhibitors) can be assigned a relative SIK activity value of 100%. Inhibition of SIK is achieved when the SIK activity value relative to the control is about 80%, optionally 50% or 25-0%.

"Cell-based assays" include SIK binding assays, for example, radioligand or fluorescent ligand binding assays for SIK to cells, plasma membranes, detergent-solubilized plasma membrane proteins, immobilized collagen; or ELISA If acting on SIK directly, in one embodiment the inhibitor should exhibit an IC50 value of about 5 uM or less, preferably 500 nm or less, more preferably 100 nm or less.

In vitro assays can also assess the ability of the inhibitor to bind SIK or to reduce or block an identified downstream effect of activated SIK, e.g., cytokine secretion such as IL-1, IL-6, TNFα and/or TGFβ. IC50 values are calculated using the concentration of inhibitor that causes a 50% decrease as compared to a control.

A binding assay is a fairly inexpensive and simple in vitro assay to run. Binding of a molecule to SIK, in and of itself, can be inhibitory, due to steric, allosteric or charge-charge interactions. A binding assay can be performed in solution or on a solid phase using SIK or a fragment thereof as a target. By using this as an initial screen, one can evaluate libraries of compounds for potential SIK regulatory activity. The target in a binding assay can be either free in solution, fixed to a support, or expressed in or on the surface of a cell. A label (e.g., radioactive, fluorescent, quenching) can be placed on the target, compound, or both to determine the presence or absence of binding. This approach can also be used to conduct a competitive binding assay to assess the inhibition of binding of a target to a natural or artificial substrate or binding partner. In any case, one can measure, either directly or indirectly, the amount of free label versus bound label to determine binding. There are many known variations and adaptations of this approach to minimize interference with binding activity and optimize signal. For purposes of in vitro cellular assays, the compounds that represent potential inhibitors of SIK function can be administered to a cell in any number of ways. Preferably, the compound or composition can be added to the medium in which the cell is growing, such as tissue culture medium for cells grown in culture. The compound is provided in standard serial dilutions or in an amount determined by analogy to known modulators. Alternatively, the potential inhibitor can be encoded by a nucleic acid that is introduced into the cell wherein the cell produces the potential inhibitor itself.

One suitable in vitro assay involves detecting whether or not a test agent is able to inhibit the ability of SIK to phosphorylate a substrate, such as a peptide substrate. Such an assay can use radio labelled or isotopically labelled ATP, such that upon phosphorylation of the substrate the substrate becomes radio/isotopically labelled.

In terms of cell based assays, an exemplary assay would involve detecting whether or not a test agent is able to enhance, for example CREB-dependent gene transcription, IL-10 mRNA expression and/or IL-10, IL-1 receptor agonist or other pro-inflammatory cytokines.

Typically this will be carried out in response to adding a Toll-like receptor agonist, such as LPS, in order to induce cell, such as macrophage, stimulation.

Cytokines may be detected using ELISA assays commercially available from numerous suppliers (eg. Perkin-Elmer, R&D Systems) or MSD technology could be used for the quantification of multiple cytokines, including IL-10 from for example, LPS stimulated bone marrow derived primary mouse macrophages (assay that is currently used in Dundee). Alternatively, primary human PBMCs/monocytes or human THP-1 cells may be used. In such assays IL-10 levels should increase if SIK is inhibited. Secretion of additional cytokines (eg. the pro-inflammatory cytokines IL-6, IL-12p40, TNFα and IL-12p70) could also be measured in parallel for key compounds. In addition to detecting an effect as a SIK inhibitor, the test agents may be screened for their ability to modulate key pharmacodynamic markers regulated by SIK-CREB-IL-10, such as increases in IL-10 and inhibition of TNFα in a 384-well AlphaLISA format (Perkin-Elmer)

CREB-Dependent Gene Transcription qRT-PCR may be used to measure the increase in IL-10 mRNA after treatment with SIK inhibitors and to quantify the expression of other CREB-dependent genes (eg nurr1 and nurr77). In parallel, a suitable CREB-dependent IL-10 promoter reporter assay may be used to verify the mechanism of action of SIK inhibitors identified in biochemical and cell-based assays.

In Vivo Models

Compounds can be tested in vivo using, for example, Dextran Sulphate Sodium (DSS) to induce chronic ulcerative colitis. This is a recognized model of IBD and DSS may be administered in drinking water. The severity of the colitis is evaluated by assessing: clinical signs of disease including body weight loss, stool consistency and rectal bleeding; macroscopic markers of disease including colon macroscopic score, colon length and weight; and colon markers of inflammation including pro-inflammatory cytokines, colon histology and myeloperoxidase activity. IL-10−/− mice are also known in the art and may be employed. These mice could be used to investigate specificity for the mode of action for any lead compounds.

Candidate test agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents can be subjected to directed or random chemical modifications, such as acylation, alkylation, esterification, amidification to produce structural analogs. In some embodiments, the candidate bioactive agents are proteins. By "protein" herein is meant at least two covalently attached amino acids, which includes proteins, polypeptides, oligopeptides and peptides. The protein can be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the methods herein. "Amino acid" also includes imino acid residues such as proline and hydroxyproline. The side chains can be in either the (R) or the (S) configuration. In further embodiments, the amino acids are in the (S) or (L) configuration. If non-naturally occurring side chains are used, non-amino acid substituents can be used, for example to prevent or retard in vivo degradations.

Libraries of prokaryotic and eukaryotic proteins can be made for screening using the methods herein. The libraries can be bacterial, fungal, viral, and mammalian proteins, and human proteins. In some methods, the candidate bioactive agents are peptides of from about 5 to about 30 amino acids, typically from about 5 to about 20 amino acids, and typically from about 7 to about 15 amino acids. The peptides can be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they can incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents. In some methods, the library can be fully randomized, with no sequence preferences or constants at any position. In other methods, the library can be biased. Some positions within the sequence are either held constant, or are selected from a limited number of possibilities. For example, in some methods, the nucleotides or amino acid residues are randomized within a defined class, for example, of hydrophobic amino acids, hydrophilic residues, sterically biased (either small or large) residues, towards the creation of nucleic acid binding domains, the creation of cysteines, for crosslinking, prolines for SH-3 domains, serines, threonines, tyrosines or histidines for phosphorylation sites, or to purines. In other methods, the candidate bioactive agents are nucleic acids, as defined above.

As described above generally for proteins, nucleic acid candidate bioactive agents can be naturally occurring nucleic acids, random nucleic acids, or "biased" random nucleic acids. For example, digests of prokaryotic or eukaryotic genomes can be used as is outlined above for proteins. In some methods, the candidate bioactive agents are organic chemical moieties.

Several different drug screening methods can be accomplished to identify drugs or bioactive agents that modulate SIK activity. One such method is the screening of candidate agents that can act as an antagonist of SIK activity, thus generating the associated phenotype. Candidate agents that can act as an antagonist to SIK pathway signalling, as shown herein, is expected to result in the anti-inflammatory phenotype. Thus, in some methods, candidate agents can be determined that mimic or alter SIK pathway signalling.

In some methods, a candidate agent can be administered in any one of several cellular assays, e.g., SIK activity assay. By "administration" or "contacting" herein is meant that the candidate agent is added to the cells in such a manner as to allow the agent to act upon the cell, whether by uptake and intracellular action, or by action at the cell surface. In some embodiments, nucleic acid encoding a proteinaceous candidate agent (i.e., a peptide) can be put into a nucleic, such as a viral construct such as a retroviral construct and added to the cell, such that expression of the peptide agent is accomplished; see for example, PCT US97/01019, incorporated herein by reference in its entirety.

Pharmaceutical Compositions and Methods of Administration

SIK inhibitors, antagonists, anti-SIK antibodies and fragments thereof, can be used in treatment. In some methods, the genes encoding the inhibitors, antagonists, or antibodies are provided, such that the inhibitor, antagonist, or antibody bind to and modulate the SIK within the cell. In other methods, a therapeutically effective amount of SIK inhibitor or antagonist is administered to a patient. A "therapeutically effective amount", "pharmacologically acceptable dose", "pharmacologically acceptable amount" means that a sufficient amount of a SIK inhibitor or antagonist, or combination of agents is present to achieve a desired result, e.g., preventing, delaying, inhibiting or reversing a symptom of a disease or disorder or the progression of disease or disorder when administered in an appropriate regime. Pharmaceutically acceptable carriers are determined in part by the particular composition being administered, as well as by the particular method used to administer the composition. Accordingly, there is a wide variety of suitable formulations of pharmaceutical compositions (see, e.g., Alfonso R Gennaro (ed), Remington: *The Science and Practice of Pharmacy*, (Formerly Remington's Pharmaceutical Sciences) 20th ed., Lippincott, Williams & Wilkins, 2003, incorporated herein by reference in its entirety). The pharmaceutical compositions generally comprise MAP kinase antagonist in a form suitable for administration to a patient. The pharmaceutical compositions are generally formulated as sterile, substantially isotonic and in full compliance with all Good Manufacturing Practice (GMP) regulations of the U.S. Food and Drug Administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavour, usually sucrose and acacia ortragacanth, as well as pastilles comprising the active ingredient in an inert base, such as gelatin and glycerin or sucrose and acacia emulsions, gels, and the like containing, in addition to the active ingredient, carriers known in the art.

In some methods, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like, particularly the ammonium, potassium, sodium, calcium, and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The nucleic acids, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like. Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the packaged nucleic acid with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Compositions can be administered, for example, by intravenous infusion, orally, topically, intraperitoneally, intravesically or intrathecally. Formulations for injection can be presented in unit dosage form, e.g., in ampules or in multidose containers, with an added preservative.

Injection solutions and suspensions can be prepared from sterile powders, granules, and tablets of the kind previously described. Cells transduced by the packaged nucleic acid as described above in the context of ex vivo therapy can also be administered intravenously or parenterally as described above.

The dose administered to a patient should be sufficient to affect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient. In determining the effective amount of the vector to be administered in the treatment or prophylaxis of conditions resulting from expression of the SIK proteins of the methods and compositions, the physician evaluates circulating plasma levels of the vector, vector toxicities, progression of the disease, and the production of anti-vector antibodies. In general, the dose equivalent of a naked nucleic acid from a vector is from about 1 µg to 100 µg for a typical 70 kilogram patient, and doses of vectors which include a retroviral particle are calculated to yield an equivalent amount of therapeutic nucleic acid.

For administration, inhibitors and transduced cells can be administered at a rate determined by the LD50 of the inhibitor, vector, or transduced cell type, and the side-effects of the inhibitor, vector or cell type at various concentrations, as applied to the mass and overall health of the patient. Administration can be accomplished via single or divided doses.

Kits

SIK inhibitors, and antagonists are useful tools for examining expression and regulation of signalling in cells such as macrophages via the SIK signalling pathway. Reagents that specifically hybridize to nucleic acids encoding SIK proteins (including probes and primers of the proteins), and reagents that specifically bind to the proteins, e.g., antibodies, may be used to examine expression and regulation.

Nucleic acid assays for the presence of SIK gene expressions in a sample include numerous techniques as known to those skilled in the art, such as Southern analysis, northern analysis, dot blots, RNase protection, SI analysis, amplification techniques such as PCR and LCR, high density oligonucleotide array analysis, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4:230-250, 1986; Haase et al., *Methods in Virology*, P7/.T89-226, 1984; and *Nucleic Acid Hybridization: A Practical Approach* (Hames et al., eds. 1987), each incorporated herein by reference in their entirety. In addition, SIK protein can be detected with the various immunoassay techniques described above. The test sample is typically compared to both a positive control (e.g., a sample expressing recombinant SIK protein) and a negative control.

A wide variety of kits and components can be prepared depending upon the intended user of the kit and the particular needs of the user. For example, the kit can be tailored for in vitro or in vivo assays for measuring the activity of SIK protein. Kits comprising probe arrays as described above are provided. Optional additional components of the kit include, for example, enzyme substrate and label. Usually, the kits also contain instructions for carrying out the methods.

DETAILED DESCRIPTION

The present invention will now be further described by way of example and with reference to the figures which show:

BRIEF DESCRIPTION OF THE DRAWINGS

FIGS. 1A to 1D. MRT67307 and its derivatives increase IL-10 production and suppress pro-inflammatory cytokine production in vitro and in vivo. (FIG. 1A) MRT67307 increases IL-10 secretion while suppressing the release of pro-inflammatory cytokines in LPS-stimulated macrophages (6 h, n=4, mean±SEM). (FIG. 1B) Effect of MRT67307 on cytokine production in macrophages stimulated with a collection of TLR agonists (6 h, n=6, mean±SEM). (FIG. 1C) Comparing the effect of MRT67307 and MRT68771 on cytokine production in LPS-stimulated macrophages (6 h, n=4, mean±SEM). (FIG. 1D) Effect of MRT68771 on cytokine release into the serum of mice challenged with LPS (n=4, mean±SEM).

(FIG. 2A) MRT67307 increases LPS-induced phosphorylation of STAT3. Macrophages were treated with 2 µM MRT67307 or vehicle control prior to stimulation with LPS for the times indicated. (FIG. 2B) Phosphorylation of STAT3 does not occur in IL-10$^{-/-}$ macrophages. As in A except that cells were stimulated for 2 h with LPS. (FIGS. 2C to 2G) Comparing the effect of MRT67307 on cytokine production in IL-10$^{+/+}$ and IL-10$^{-/-}$ macrophages in response to different TLR agonists (6 h, n=7-11, mean±SEM).

(FIG. 3A) Effect of MRT67307 on IL-10 mRNA levels in macrophages stimulated for 2 h with different TLR agonists (n=4, mean±SEM). (FIG. 3B) Effect of MRT67307 on the transcription of CREB-dependent genes (IL-10, c-fos, nurr1, nurr77) in LPS-stimulated macrophages (n=4, mean±SEM). (FIG. 3C) Effect of MRT67307 on phosphorylation of CREB and ATF1 in response to LPS. (FIG. 3D) Proteomics pipeline to study the effects of MRT67307 on the phosphoproteome of Pam$_3$CSK$_4$-stimulated macrophages. (FIG. 3E) Mass spectrum showing phosphopeptide precursor ions corresponding to CRTC3 that is dephosphorylated at Ser329 in macrophages treated with MRT67307. (FIG. 3F) Summary of phosphoproteomic results showing the dephosphorylation of Ser329 and Ser370 of CRTC3 induced by MRT67307.

FIGS. 4A to 4E. Inhibition of SIKs simultaneously enhances IL-10 production and suppresses pro-inflammatory cytokine secretion. (FIG. 4A) IC50s of different inhibitors of the AMPK-related kinases. (FIGS. 4B and 4C) Effect of (FIG. 4B) MRT199665 and the SIK-specific inhibitor (FIG. 4C) KIN112 on CREB-dependent gene transcription and cytokine secretion in LPS-stimulated macrophages (n=4, mean±SEM). (FIG. 4D) Effect of MRT67307 and KIN112 on CREB-dependent gene transcription in IL-1 stimulated MEFs from LKB1+/+ and LKB1−/− mice. (FIG. 4E) Effect of MRT67307 on the transcription of IL-1ra, ArgI, SPHK1 and LIGHT in LPS-stimulated macrophages (4 h, n=4, mean±SEM).

(FIG. 6A) Comparing the dose response curves of MRT67307 on IFNβ and IL-10 mRNA levels in LPS-stimulated macrophages (n=4, mean±SEM). (FIG. 6B) Effect of MRT67307 on the mRNA levels of nurr77 in IL-1 stimulated TBK1/IKKi$^{+/-}$ and TBK1/IKKi$^{-/-}$ mouse embryonic fibroblasts.

(FIGS. 7A to 7C) The activity of a panel of 108 protein kinases was measured in the presence of (FIG. 7A) 1 µM MRT67307, (FIG. 7B) 1 µM MRT199665 and (FIG. 7C) 1 µM KIN112. The data are reported as the % activity remaining in the presence of the inhibitor. The red line indicates 90% inhibition of the protein kinase by the inhibitor. (n=2, mean±SD).

(FIG. 8A) Co-activator function of CRTC3 becomes constitutive and insensitive to SIK inhibitors when S62, S162, S329 and S370 are mutated to Ala. CRTC3-3A is the mutant CRTC3[S62A/S329A/S370A] whereas CRTC3-4A is CRTC3-3A also carrying the S162A mutation. (mean±SD, n=3). (FIG. 8B) Mutation of CRTC3 at Ser62, Ser162, Ser329 and Ser370 to Ala abolishes interaction with 14-3-3 proteins. (FIG. 8C) WT CRTC3 translocates to the nucleus after treatment with MRT199665 or HG-9-91-01, whereas CRTC3-4A is localised to the nucleus even in absence of SIK inhibitors. (FIG. 8D) SIKs phosphorylate CRTC3 in vitro inducing interactions with 14-3-3 proteins. NK, no kinase. (FIG. 8E) Inhibition of SIKs promotes dephosphorylation of endogenous CRTC3 and loss of 14-3-3 interaction. (FIG. 8F) Expression of FLAG-CRTC3-WT and -4A upon treatment of RAW264.7 macrophages with doxycyclin. (FIG. 8G) RAW264.7 macrophages expressing the phosphomutant CRTC3-4A produce elevated levels of IL-10 mRNA, which is not enhanced by SIK inhibition (n=4, mean±SD).

FIGS. 9A to 9I. Genetic evidence using LKB1-deficient macrophages and a drug-resistant mutant of SIK2 to establish that inhibition of SIKs induces IL-10 production. (FIG. 9A) Loss of CRTC3 phosphorylation in LKB1−/− MEFs. (FIG. 9B) Enhanced IL-10 production and reduced secretion of pro-inflammatory cytokines in LysM-Cre-LKB1flox/flox macrophages (n=3, mean±SD). (FIG. 9C) Sequence alignment of AMPK-related kinases. The 'gatekeeper' site is indicated using an asterisk. (FIG. 9D) 1050 curves of KIN112 against different SIK2 mutants. (FIG. 9E) 1050 curve of HG-9-91-01 against WT SIK2 and the SIK2[T960] mutant. (FIG. 9F) Induction of HA-SIK2 (WT and [T96Q]) expression in RAW264.7 macrophages. (FIG. 9G) HG-9-91-01 fails to induce IL-10 and Nurr77 mRNA production in cells expressing SIK2[T960]. RAW264.7 cells were induced to express HA-SIK2-WT or HA-SIK2[T96]. As a further control, cells transduced with the empty vector and which only express endogenous SIK isoforms were also used. Subsequently, cells were treated without or with 500 nM HG-9-91-01 and stimulated for 1 h with 100 ng/ml LPS. mRNA levels were measured by qPCR (mean±SD, n=3). (FIG. 9H) 1050 curve of MRT67307 against WT SIK2 and the SIK2[T960] mutant. (FIG. 9I) MRT67307 but not HG-9-91-01 can potentiate the production of IL-10 in macrophages expressing SIK2[T960]. Experiment was performed as in panel E but cells were treated with 2 µM MRT67307 or 500 nM HG-9-91-01 prior to stimulation for 1 h with Pam3CSK4 (mean±SD, n=3) (*p<0.001 when compared to cells stimulated with Pam3CSK4 in the absence of inhibitors).

(FIG. 10A) Effect of SIK inhibitors on the LPS-stimulated expression of LIGHT, SPHK1, Arg1 and IL-1ra (n=4, mean±SD). (FIG. 10B) Effect of HG-9-91-01 on macrophage marker expression in LPS-stimulated BMDMs. mRNA levels were normalised to 1 in unstimulated cells not treated with HG-9-91-01 (mean±SD, n=4). (FIG. 10C) Elevated expression of markers of regulatory macrophage in LKB1−/− macrophages. BMDMs were generated from LysM-Cre/LKB1+/+ and LysM-Cre/LKB1flox/flox mice and stimulated with 100 ng/ml LPS (mean±SD, n=3). (FIG. 10D) CRTC3 is required for the induction of markers of regulatory macrophages. BMDMs were transfected with control or CRTC3 siRNA oligonucleotides, treated without or with 500 nM HG-9-91-01 and then stimulated with 100 ng/ml LPS. LIGHT and SPHK1 mRNA was measured at 2 h and Arg1 at 8 h post-LPS stimulation (mean±SD, n=4). (FIG. 10E) Regulatory macrophage markers are not induced by HG-9-91-01 in IL-10−/− macrophages. The experiment was carried out as in (FIG. 10D) except that BMDMs were generated from IL-10+/+ and IL-10−/− mice (mean±SD, n=4).

(FIGS. 11A to 11C) The activities of 108 protein kinases were measured in the presence of (FIG. 11A) 1 µM MRT67307, (FIG. 11B) 1 µM MRT199665, (FIG. 11C) 1 µM KIN112. and (FIG. 11D) 0.1 µM HG-9-91-01 The data are reported as the % activity remaining in the presence of the inhibitor relative to the activity measured in the absence of inhibitor. The red bars indicate the protein kinases inhibited most potently (n=2, mean±SD).

FIGS. 12A to 12C. Effect of SIK inhibitors on TLR-stimulated cytokine production. (FIG. 12A) MRT67307, MRT199665, KIN112 and HG-9-91-01 stimulate IL-10 secretion in a dose dependent manner. BMDMs were treated for 1 h with the indicated concentrations of MRT67307, MRT199665, KIN112 and HG-9-91-01, then stimulated for 6 h with LPS. IL-10 levels in culture supernatants were measured using the Bio-Plex kit (n=4, mean±SD). (FIG. 12B) Effect of KIN112 on LPS-stimulated mRNA and cytokine production. BMDMs were treated for 1 h with 10 μM KIN112 and then stimulated for 1 h with 100 ng/ml LPS (mRNA expression) or for 6 h (protein secretion) (mean±SD, n=4). (FIG. 12C) Effect of HG-9-91-01 on cytokine production in macrophages co-stimulated with LPS and IFNγ. BMDMs were incubated for 1 h with 500 nM HG-9-91-01 then stimulated with 10 ng/ml IFNγ and/or 100 ng/ml LPS. IL-10 mRNA levels were measured by qPCR after stimulation for 1 h and cytokine secretion measured after 6 h of stimulation (mean±SD, n=4). p<0.01 and *p<0.001 when compared to samples treated with vehicle control.

FIG. 13. siRNA knockdown of CRTC3 abolishes the effects of HG-9-91-01 on IL-10 production in primary macrophages. BMDMs were transfected with siRNA oligonucleotides against CRTC1, CRTC2, CRTC3 or non-targeting oligonucleotides as a negative control. Cells were incubated for 1 h without or with or 500 nM HG-9-91-01, then stimulated for a further 1 h with 100 ng/ml LPS. Gene expression was quantified by qPCR and reported relative to mRNA levels measured in untreated cells (1.0). Knockdown efficiency was monitored by qPCR (mean±SD, n=4).

(FIGS. 14A to 14B) Effect of MRT67307 and KIN112 on LPS-stimulated CREB-dependent gene transcription and IL-10 production in dendritic cells. Bone marrow was differentiated into dendritic cells (BMDCs) by incubation for 7 days in the presence of GM-CSF. BMDCs were incubated for 1 h with 2 μM MRT67307 or 10 μM KIN112 and then stimulated for 1 h with 100 ng/ml LPS (mRNA expression) (FIG. 14A) or the culture supernatant was harvested at the times indicated and protein secretion measured (FIG. 14B) (mean±SD, n=4). (FIGS. 14C to 14D) Effect of SIK inhibitors on mRNA production in human cells. (FIG. 14C) THP-1 monocytes were treated with 1 μM MRT199665 or 10 μM KIN112 for 1 h and then stimulated with 1 mg/ml Pam$_3$CSK$_4$ for 1 h. (FIG. 14D) Primary human macrophages were incubated for 1 h with 1 μM MRT199665 or 500 nM HG-9-91-01 and then stimulated for 1 h with 100 ng/ml LPS. mRNA levels were measured by qPCR (mean±SD, n=4).

(FIG. 15A) HEK293 cells were transfected with FLAG-CRTC2, FLAG-CRTC3 or FLG-CRTC3[S162A]. Aliquots of the cell extracts were subjected to SDS-PAGE and immunoblotting using an antibody that recognizes CRTC2 phosphorylated at Ser171. The figure shows that this antibody also recognizes CRTC3 phosphorylated at Ser162. (FIG. 15B) HEK293 cells were transfected with FLAG-CRTC3, FLAG-CRTC3[S62A/S162A/S329A/S370A] (termed CRTC3-4A) or with empty vector (FLAG-ev). After transfection, cells were incubated for 1 h without (control) or with 2 μM MRT67307, 1 μM MRT199665, 10 μM KIN112 or 500 nM HG-9-91-01. (FIG. 15C) Inhibition of SIKs promotes the translocation of endogenous CRTC3 to the nucleus. RAW264.7 cells were treated with MRT67307, MRT199665, KIN112 or HG-9-91-01 for 1 h and stained for CRTC3 (red), tubulin (green), and DNA (DAPI-blue).

(FIG. 16A) mRNA abundance of SIK1, SIK2 and SIK3 in RAW264.7 macrophages. Gene expression was measured by qPCR. The number of copies of each SIK mRNA was normalized to GAPDH. (mean±SD, n=3). (FIG. 16B) The efficiency of SIK knock-down. RAW264.7 cells were transduced with lentiviral vectors encoding a control shRNA or shRNAs targetting SIK1, SIK2 and SIK3. The expression of SIK1, SIK2 and SIK3 was measured by qPCR and normalized to that of control cells using GAPDH (mean±SD, n=3). (FIG. 16C) The concentration of HG-9-91-01 required to stimulate IL-10 mRNA is reduced in cells with decreased SIK expression. Cells were incubated for 1 h with increasing concentrations of HG-9-91-01, then stimulated for 1 h with 1 μg/ml Pam3CSK4. The levels of IL-10 mRNA were measured by qPCR and normalized using GAPDH. Data are presented with the highest level of expression set to 1 (mean±SD, n=3). IC50 for control cells (closed symbols) was 260±10 nM and SIK1/2/3 shRNA cells (open symbols) was 150±20 nM (p<0.01). (FIG. 16D) Increased IL-10 expression in cells with decreased SIK expression. Same as panel C, except that HG-9-91-01 concentration was held at 100 nM (mean±SD, n=3).

METHODS

Figure 2A:
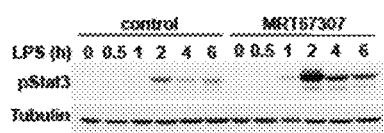
FIGS. 2A to 2G. MRT67307 inhibits pro-inflammatory cytokine production by an IL-10-dependent mechanism.

The following five compounds were studied:
MRT67307
MRT68771
MRT199665;
KIN112; and
HG-9-91-01.

MRT1199665 was prepared according to the methods discussed in Haidle, Andrew; Stanton, Matthew; Altman, Michael; Konrad, Kaleen; Zabierek, Anna; Katz, Jason; Jewell, James, PCT Int. Appl. (2009), WO 2009152027 A1.

I7-[(1S)-4-hydroxy-2,3-dihydro-1H-inden-1-yl]-5,5-dimethyl-2 (methylsulfonyl)-5,7-dihydro-6H-pyrrolo[2,3-d]pyrimidin-6-one

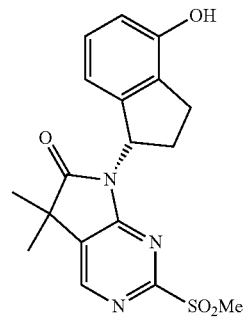

was prepared initially.

7-[(1S)-4-hydroxy-2,3-dihydro-1H-inden-1-yl]-5,5-dimethyl-2-{[3-(pyrrolidin-1-ylmethyl)phenyl]amino}-5,7-dihydro-6H-pyrrolo[2,3-d]pyrimidin-6-one

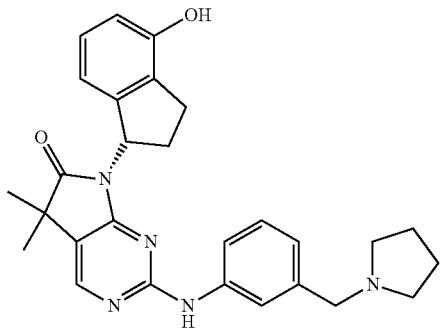

7-[(1S)-4-hydroxy-2,3-dihydro-1H-inden-1-yl]-5,5-dimethyl-2-(methylsulfonyl)-5,7-dihydro-6H-pyrrolo[2,3-d]pyrimidin-6-one (75 mg, 0.2 mmol) and 3-(pyrrolidin-1-ylmethyl)aniline (106 mg, 0.6 mmol) were added to NMP (0.5 ml), and the resulting mixture was irradiated at 180° C. for 1 h in a Biotage 1-60 microwave reactor. The mixture was cooled, filtered and the filtrate was purified by preparative LCMS to give a brown solid (20 mg, 21%). $^1$H NMR (400 MHz, DMSO-$d_6$) δp.p.m. 9.45 (s, 1H), 9.40 (s, 1H), 8.23 (s, 1H), 7.17-7.57 (m, 2H), 7.12 (t, J=7.8 Hz, 1H), 6.87-7.00 (m, 1H), 6.80 (d, J=7.3 Hz, 1H), 6.66 (d, J=8.2 Hz, 1H), 6.42 (d, J=7.3 Hz, 1H), 5.86 (t, J=8.70 Hz, 1H), 3.40-3.52 (m, 2H), 2.99-3.17 (m, 1H), 2.73-2.93 (m, 1H), 2.56-2.71 (m, 1H), 2.26-2.44 (m, 5H), 1.53-1.74 (m, 4H), 1.15-1.50 (m, 6H); $^{13}$C NMR (101 MHz, CDCl$_3$) δ p.p.m. 181.42, 162.93, 158.74, 153.15, 148.47, 142.40, 139.18, 138.55, 129.86, 128.99, 128.10, 123.46, 120.00, 118.28, 117.46, 114.64, 60.53, 56.02, 54.07, 42.48, 28.10, 27.23, 24.71, 24.04, 23.18; HRMS (m/z): [M+H]$^+$ calcd for $C_{28}H_{31}N_5O_2$, 470.2551; found 470.2547.

Preparative HPLC Conditions:

HPLC column: 4.6×50 mm (5 μm) C-18 Xbridge; flow rate: 3 ml/min; Run time: 3.2 min: Solvent A: 0.1% Ammonium Hydroxide in water; Solvent B: Methanol; Gradient: 10-100% B; Gradient time: 2.35 min. HPLC retention time (2.15 min).

Compounds MRT68771 and MRT67307 were prepared according to methods described by McIver, Edward Giles; Bryans, Justin Stephen; Smiljanic, Ela; Lewis, Stephen John; Hough, Joanne; Drake, Thomas, PCT Int. Appl. (2009), WO 2009122180 A1.

KIN112 was prepared as described in Martin, M., et al J. Med. Chem., 2006, 49, 4981-4991 and is identified as Compound 28, see also http://www.kinase-screen.mrc.ac.uk/kinase-inhibitors?field_compound inhibitor_value=&page=2.

Materials

MRT67307, MRT68771, MRT199665 and KIN112 were dissolved in DMSO and stored at −20° C. as 10 mM solutions. The TLR agonists Pam$_3$CSK$_4$, LTA, poly(I:C), R837 and CpG (ODN1826) were from Invivogen and LPS (E. coli 055:65) from Alexis Biochemicals. M-CSF was purchased from R&D Systems.

Mice

IL-10$^{-/-}$ mice on a C57Bl/6 background were purchased from The Jackson Laboratory, Maine, USA. C57Bl/6, and IL-10$^{-/-}$ mice were bred at the University of Dundee under specific pathogen-free conditions in accordance with European Union regulations. Work was approved by local ethical review and was performed with a UK Home Office project license.

Stimulation of Macrophages

Bone-marrow derived macrophages were differentiated for 7 days in DMEM supplemented with 5 ng/ml recombinant M-CSF (R&D systems), 2 mM glutamine, 10% foetal calf serum, penicillin and streptomycin. Macrophages were treated for 1 h with inhibitors (2 μM MRT67307, 2 μM MRT68771, 1 μM MRT199665, 10 μM KIN112) or an equivalent volume of DMSO for control incubations then stimulated for up to 24 h with either 1 μg/ml Pam$_3$CSK$_4$, 2 μg/ml LTA, 10 μg/ml poly(I:C), 100 ng/ml LPS, 1 μg/ml R837 or 2 μM CpG.

Immunoblotting

Cells were rinsed in ice-cold PBS and extracted in lysis buffer (50 mM Tris/HCl pH 7.4, 1 mM EDTA, 1 mM EGTA, 50 mM NaF, 5 mM sodium pyrophosphate, 10 mM sodium α-glycerol 1-phosphate, 1 mM dithiothreitol, 1 mM sodium orthovanadate, 0.27 M sucrose, 1% (v/v) Triton X-100, 1 μg/ml aprotinin, 1 μg/ml leupeptin and 1 mM phenylmethylsulphonyl fluoride). Cell extracts were clarified by centrifugation at 14000×g for 10 min at 4° C. and protein concentrations determined using the Bradford assay. To detect proteins in cell lysates, 20 μg of protein extract was separated by SDS-PAGE. After transfer to PVDF membranes, proteins were detected by immunoblotting and visualized by treating the blots with ECL (Amersham) followed by autoradiography. The antibody recognizing CREB phosphorylated at Ser133 was from Cell Signalling Technology and the one detecting α-tubulin was obtained from Sigma.

QPCR mRNA was extracted from macrophages using the RNeasy Micro Kit following the manufacturers' instructions (Qiagen). cDNA was generated from 1 μg of total RNA using the iScript cDNA synthesis kit and quantified by qPCR using the SsoFast EvaGreen Supermix on a CFX96 real time system (Bio-Rad Laboratories). The relative expression of each gene was calculated from Ct values using the Pfaffl method[30] and was normalized against the mRNA levels of 18S RNA. The following primers were used: IL-10-F, CCCTTTGCTATGGTGTCCTTTC; IL-10-R, GATCTCCCTGGTTTCTCTTCCC; c-Fos-F, CTACTGTGTTCCTGGCAATAGC; c-Fos-R, AACATTGACGCTGAAGGACTAC; nurr1-F, GAAGAGAGCGGACAAGGAGATC; nurr1-R, AAGGCATGGCTTCAGCAGAG; nurr77-F, CCTGTTGCTAGAGTCTGCCTTC; nurr77-R, CAATCCAATCACCAAAGCCACG; 18S-F, GTAACCCGTTGAACCCCATT; 18S-R, CCATCCAATCGGTAGTAGCG; IL-1ra-F, TCCTTTATACACAGCAAGTCTC; IL-1ra-R, TTCTGAAGGCTTGCATCTTG; SPHK1-F, ACAGCAGTGTGCAGTTGATGA; SPHK1-R, GGCAGTCATGTCCGGTGATG; LIGHT-F, CTGCATCAACGTCTTGGAGA; LIGHT-R, GATACGTCAAGCCCCTCAAG; ArgI-F, CTCCAAGCCAAAGTCCTTAGAG; ArgI-R, AGGAGCTGTCATTAGGGACATC; IFN-F, GGAAAAGCAAGAGGAAAGATTGAC; IFNγ-R, CCACCATCCAGGCGTAGC.

Cytokine Secretion

Following stimulation with ligands, the cell culture medium was removed, clarified by centrifugation for 10 min at 14000×g and the concentration of TNFα, IL-6, IL-10, IL-12p40, and RANTES were measured using the Bio-Plex Pro Assay system from Bio-Rad. IFNβ was measured using an ELISA kit from R&D Systems according to the manufacturers' instructions.

Cytokine Levels in Mouse Serum

C57BL/6 mice (8-12 week old male mice) were injected with vehicle control or 0-30 mg/kg of MRT68771. After 30 min, LPS was introduced by intraperitoneal injection (3.5 mg/kg). One hour later, the mice were sacrificed and the concentrations of TNFα, IL-10 and IFNβ in the sera were measured as described above.

Phosphoproteomics

RAW264.7 cells were labelled using the Stable Isotope Labelling of Amino Acids in Cell Culture (SILAC) method. Cells were treated with 2 µM MRT67307 or vehicle control for 1 h and subsequently, left unstimulated or stimulated with 1 µg/ml $Pam_3CSK_4$ for 30 min. The cells were lysed in detergent-free lysis buffer (8 M urea, 50 mM Tris pH8.2, 10 mM glycerol 2-phosphate, 50 mM sodium fluoride, 5 mM sodium pyrophosphate, 1 mM EDTA, 1 mM sodium orthovanadate, 10 mM DTT, 1 mM PMSF, 1 µg/ml aprotinin, 1 µg/ml leupeptin), the extract clarified by centrifugation and protein concentration determined using the Bradford method. 2 mg of cell extract protein from each experimental condition were mixed in a 1:1:1 ratio and then alkylated with 50 mM iodoacetamide for 30 min. The sample was diluted with 0.1 M ammonium bicarbonate to a final urea concentration of 1.5 M and the proteins were digested overnight with 100 µg trypsin at 37° C. The digests were acidified, desalted using a C18 Sep-Pak cartridges (Waters) and the peptides were dried using a SpeedVac. These peptides were dissolved in 750 µl of 80% (v/v) ACN/0.1% (v/v) TFA and fractionated by hydrophilic (HILIC) chromatography[31]. The samples were loaded on a TSKgel Amide-80 column (TOSOH, dimension: 4.6 mm×25 cm) and the gradient developed as previously described[32]. Under these conditions, the phosphopeptides elute between 20-70 min from the HILIC column. Phosphopeptides from these samples were enriched using a standard $Fe^{3+}$-IMAC enrichment protocol[32] and measured by LC-MS/MS. Samples were separated on a Proxeon Easy-nLC system (Thermo Fisher Scientific) using a 20 cm long, 75 µm internal diameter PicoFrit column (New Objective) home-packed with Magic C18 reverse phase material (Michrom Bioresources) and the following gradient: i) 0-170 min from 2% to 35% buffer B (0.08% (v/v) formic acid, 90% (v/v) acetonitrile in water); ii) 170-187 min from 35% to 80% buffer B; iii) 187-188 min from 80% to 90% buffer B; 188-198 min isocratic at 90% buffer B; 198-199 min from 90% to 2% buffer B; 199-204 min isocratic at 2% buffer B. Buffer A composition was: 0.1%% (v/v) formic acid, 2%% (v/v) acetonitrile in water. The nano-LC system was online with a Thermo Fisher Scientific IQ Orbitrap Velos instrument set to perform top-15 data-dependent CID analysis in the 350-1600 m/z range using a resolution of 60000 for the precursor scan and a minimal intensity for sequencing of 10000 counts. Monoisotopic precursor selection was used and +1 as well as unassigned charge states were excluded from sequencing. Dynamic exclusion was set to a repeat count of 2 within 30 sec, with exclusion duration of 90 sec and an exclusion mass width of 10 ppm. The data was analysed using MaxQUANT[33].

Statistical Analysis

Quantitative data are presented as the mean±SEM. Statistical significance of differences between experimental groups was assessed using the Student's t test. Differences in means were considered significant if p<0.05.

Results

While developing MRT67307 as an inhibitor of the IKK-related kinases[5,6], we noticed that macrophages incubated with this compound secreted far higher levels of IL-10 and much lower levels of pro-inflammatory cytokines in response to bacterial lipopolysaccharide, a ligand for TLR4 (FIG. 1A). Similar results were obtained when macrophages were stimulated with ligands that activate other TLRs (FIG. 1B) while MRT68771 (FIG. 5), a structurally related compound with improved drug metabolism and pharmacokinetic properties, induced the secretion of elevated levels of IL-10 and reduced levels of pro-inflammatory cytokines in the serum of LPS-injected mice (FIG. 1D), as well as in LPS-stimulated macrophages (FIG. 1C). These striking findings led us to investigate the molecular mechanism by which MRT67307 and related compounds were exerting this effect.

Figure 2B:
Figure 2C:
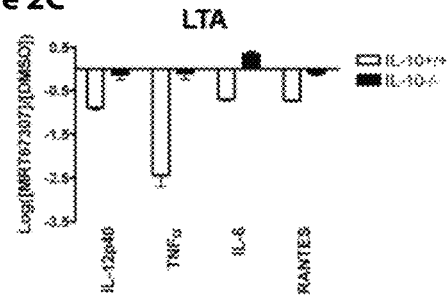

Following its secretion, IL-10 stimulates macrophages by activating the IL-10 receptor, leading to activation of the JAK1-STAT3 signaling axis[7]. Consistent with the elevated levels of IL-10 in MRT67307-treated macrophages, the LPS-stimulated phosphorylation of STAT3 was also increased in the presence of MRT67307 (FIG. 2A). In contrast, no phosphorylation of STAT3 occurred in LPS-stimulated macrophages from $IL-10^{-/-}$ mice in the presence or absence of MRT67307 (FIG. 2B). Thus the increased production of IL-10 observed in the presence of MRT67307 results in increased IL-10 signaling in macrophages.

$IL-10^{-/-}$ mice progressively develop inflammatory disorders due to a failure to adequately suppress the production of pro-inflammatory cytokines[8]. Similarly, we found that, in macrophages from $IL-10^{-/-}$ mice, MRT67307 failed to suppress the secretion of pro-inflammatory cytokines in response to all TLR ligands examined (FIGS. 2C to 2F), except for LPS (FIG. 2G). Taken together, the results show that MRT67307 can inhibit pro-inflammatory cytokine production by IL-10-dependent and IL-10-independent mechanisms depending on the particular TLR ligand. TLR4 is unique among the TLRs in signaling via the adaptor TRIF, as well as via the adaptor MyD88[1], suggesting that a TRIF-dependent signaling event may underlie the IL-10-independent suppression of pro-inflammatory cytokine production by LPS.

Figure 3A:
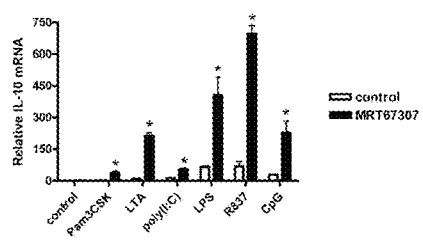
FIGS. 3A to 3F. MRT67307 increases CREB-dependent gene transcription by promoting the dephosphorylation of CRTCs.
Figure 3B:
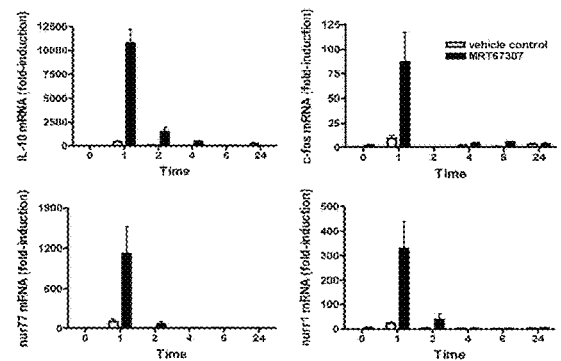
Figure 5:
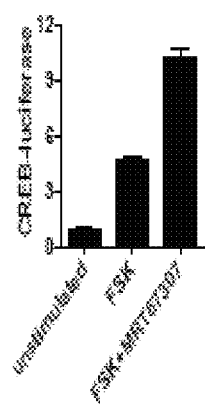
FIG. 5. MRT67307 increases CREB-dependent gene transcription. HEK293 cells were co-transfected with DNA encoding a CREB luciferase reporter construct and pTK-RL. At 24 h post-transfection, cells were incubated for 1 h without or with 2 µM MRT67307 prior to stimulation with 10 µM forskolin for 2 h. Luciferase activity was measured with a dual luciferase assay system (Promega) and was normalized to *Renilla* luciferase activity (n=3, mean±SEM).

To investigate how MRT67307 increases IL-10 secretion, we studied the molecular events leading to the formation of IL-10. Initial experiments revealed that MRT67307 dramatically increased the formation of IL-10 mRNA in TLR-stimulated macrophages (FIG. 3A). The effects were rapid and transient, IL-10 mRNA levels reaching a maximum after 1 h, and returning to near basal levels after 4 h (FIG. 3B). Since one pathway by which TLR ligands stimulate transcription of the IL-10 gene involves the activation of the transcription factor CREB[9], we initially studied whether MRT67307 could enhance the formation of the mRNA encoding other CREB-dependent genes, such as those encoding the transcription factor c-fos and the nuclear orphan receptors nurr1 and nurr77. MRT67307 did indeed increase the TLR-stimulated mRNA encoding these proteins (FIG. 3B) as well as the transcription of luciferase placed under the control of an isolated CREB element (FIG. 5). Our results therefore indicate that MRT67307 enhances IL-10 production by stimulating CREB-dependent gene transcription in TLR-stimulated macrophages.

Figure 6A:
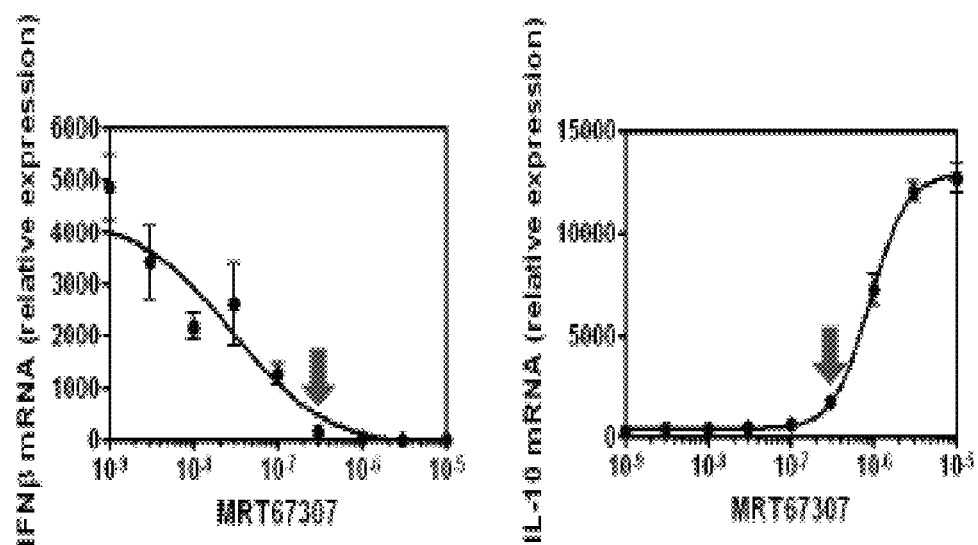
FIGS. 6A to 6B. The effects of MRT67307 on CREB-dependent gene transcription including that of the IL-10 gene are not the result of inhibition of the IKK-related kinases.
Figure 6B:
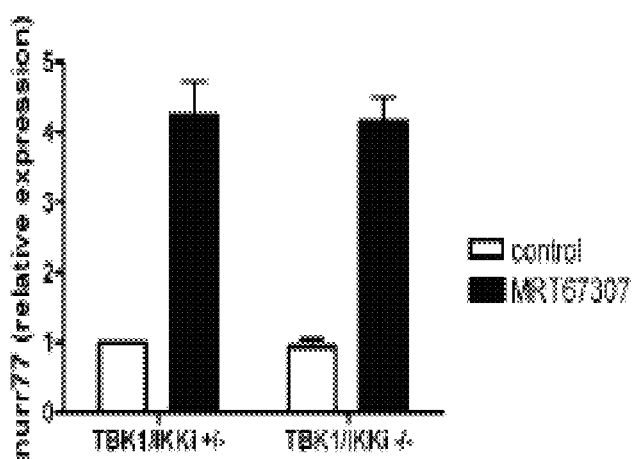

The effects of MRT67307 on CREB-dependent gene transcription were intriguing because this compound was developed as an inhibitor of the IKK-related kinases[5], which control the activity of the transcription factors IRF3 and NFκB[5,6,10,11] but have never been associated with CREB function. Phosphorylation of IRF3 by TBK1 and IKKε is required for the production of Type I interferons in response to bacterial and viral infection[12-14]. We noticed that MRT67307 potently inhibited IFNβ secretion at concentrations that were 10-fold lower than those required to increase the LPS-stimulated production of IL-10 (FIG. 6A). Moreover, MRT67307 could still enhance transcription of the CREB-dependent nurr77 gene in embryonic fibroblasts from mice that do not express either of the IKK-related kinases (FIG. 6B). These findings clearly indicated that MRT67307 was stimulating CREB-dependent gene transcription and IL-10 production by another mechanism, most likely by inhibiting a different protein kinase(s).

Figure 3D:
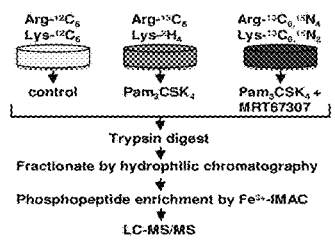
Figure 3C:
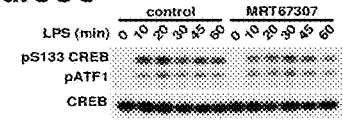
Figure 3E:
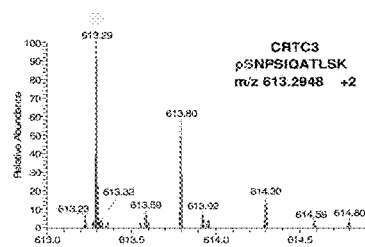
Figure 3F:
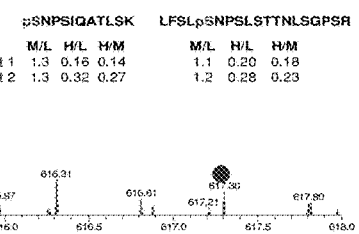

The activation of CREB by TLR ligands is known to require its phosphorylation at Ser133, which is catalysed by the Mitogen and Stress-activated Kinases 1 and 2[15], and generates a docking site for the cofactors CREB-Binding Protein (CBP) and the closely related p300[16]. CREB-dependent gene transcription can be further enhanced by interactions with the CREB-regulated Transcriptional Co-activators (CRTCs). Dephosphorylation of CRTCs releases them from 14-3-3 proteins facilitating their entry into the nucleus where they associate with CREB to promote CREB-dependent gene transcription[16]. We found that MRT67307 had little effect on the phosphorylation of CREB at Ser133 induced by LPS (FIG. 3C). However, a phosphoproteomic study to identify proteins whose phosphorylation was suppressed by MRT67307 (FIG. 3D) revealed that although the phosphorylation of CRTC3 was unaffected by stimulation with the TLR1/2 agonist $Pam_3CSK_4$, it was nevertheless robustly dephosphorylated at Ser329 and Ser370 when macrophages were incubated with MRT67307 (FIG. 3E).

To our knowledge, members of the CRTC family have not been studied previously in macrophages but, in other mammalian cells, are reported to be phosphorylated by members of the AMP-activated protein kinase (AMPK) subfamily of protein kinases, including the Microtubule Affinity-Regulating Kinases (MARKs) and the Salt-Inducible Kinases (SIKs), as well as AMPK itself[17-19]. These findings were intriguing because we have reported that BX795, from which MRT67307 was developed, is a potent inhibitor of the MARKs and the AMPK family member NUAK1, as well as the IKK-related kinases[20]. We therefore assayed MRT67307 against all the members of the AMPK subfamily, which revealed that this compound inhibited the MARK, NUAK and SIK isoforms with comparable potency to the IKK-related kinases (FIG. 4A). However it did not inhibit the Brain-Specific Kinases (BRSKs) and only inhibited the Maternal Embryonic Leucine zipper Kinase (MELK) and AMPK itself more weakly.

Figure 7A:
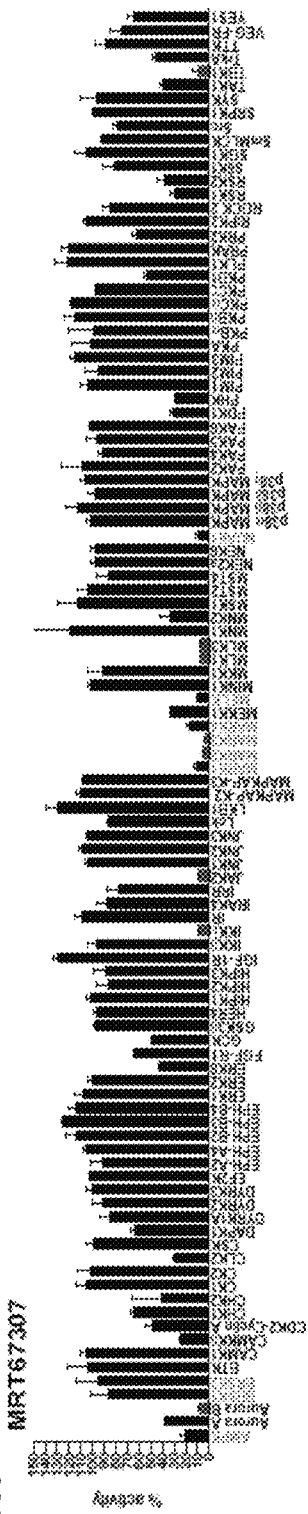
FIGS. 7A to 7C. Selectivity of MRT67307, MRT199665 and KIN112.
Figure 7B:
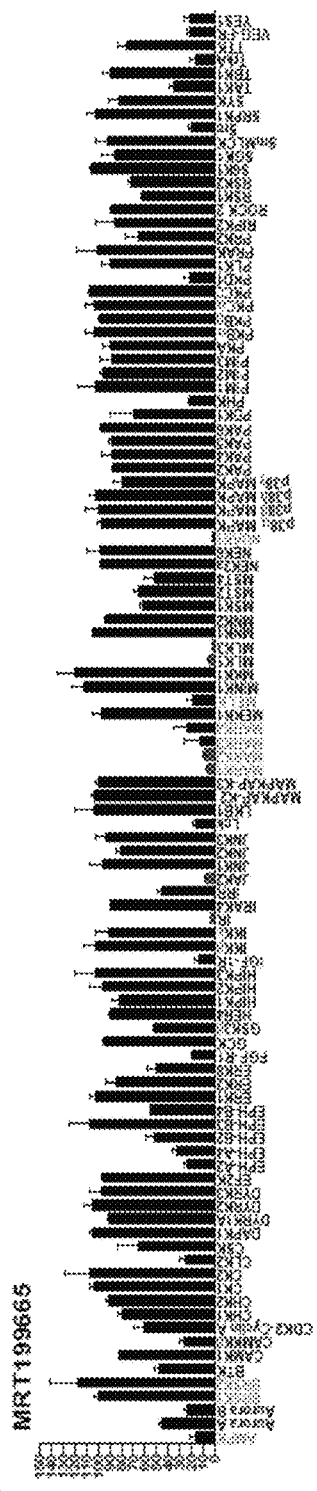
Figure 7C:
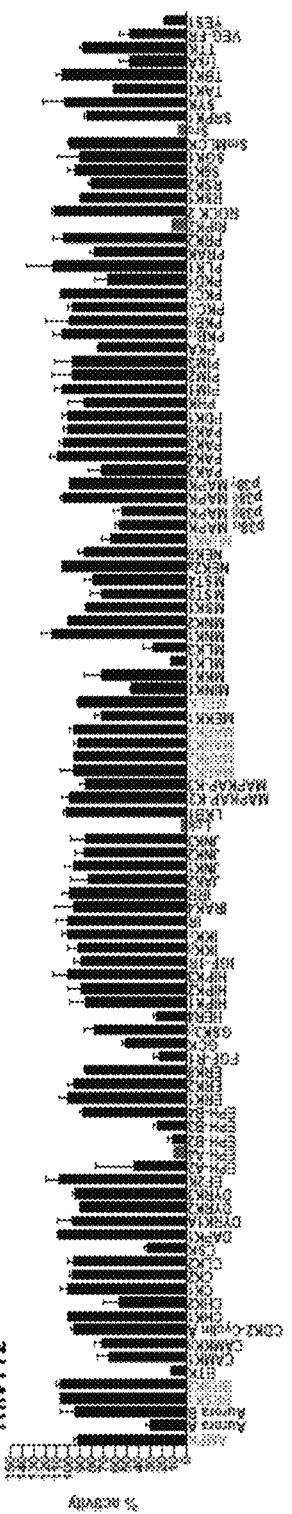

To identify which AMPK family member might be regulating CREB-dependent gene transcription and IL-10 production, we exploited additional pharmacological inhibitors with distinct specificities from MRT67307. MRT199665, a potent inhibitor of most AMPK-related kinases, which does not inhibit the IKK-related kinases (FIG. 4A), increased LPS-stimulated IL-10 mRNA and Nurr77 mRNA production, as well as IL-10 secretion (FIG. 4B), further supporting the view that inhibition of AMPK-related kinases drives IL-10 production. The SIKs are unique among the AMPK-related kinases in possessing a small amino acid residue (threonine) at the "gatekeeper" site[21,22]. We therefore developed KIN112, which not only targets the ATP-binding site, but also a small hydrophobic pocket adjacent to this site that is created by the presence of a small amino acid residue at the "gatekeeper" site. KIN112 was a potent inhibitor of many protein kinases that possess a threonine residue at the "gatekeeper" site, including the SIKs (FIG. 7C) but, importantly, did not inhibit any other member of the AMPK-related kinase subfamily (FIG. 4A), which all possess a large hydrophobic residue (Met or Leu) at this position. Like MRT67307 and MRT199665, KIN112 increased IL-10 and Nurr77 mRNA production and IL-10 secretion, and suppressed pro-inflammatory cytokine secretion (FIG. 4C).

To obtain genetic evidence that inhibition of the SIKs underlies the ability of MRT67307 and KIN112 to stimulate CREB-dependent gene transcription, we tested the effects of these compounds in LKB1−/− cells. All members of the AMPK-subfamily, apart from MELK, are active only after phosphorylation by the protein kinase LKB1[23]. The activity of SIKs should therefore be low in LKB1−/− cells leading to increased CREB-dependent gene transcription. These experiments confirmed this hypothesis by showing that transcription of the CREB-dependent genes Nurr1 and Nurr77 was much higher in LKB1−/− cells before or after stimulation with IL-1 (FIG. 4D). Moreover, the transcription of Nurr1 and Nurr77 could only be increased to a small extent by MRT67307 or KIN112 in LKB1−/− cells. In contrast, MRT67307 or KIN112 enhanced CREB-dependent gene transcription in LKB1+/+ cells to a level similar to that observed in LKB1−/− cells in the presence or absence of MRT67307 or KIN112 (FIG. 4E). Taken together, these findings identify the SIKs as the AMPK family members that suppress CREB-dependent gene transcription and IL-10 secretion by phosphorylating CRTC family members.

In contrast to classically activated macrophages, which secrete pro-inflammatory cytokines and possess enhanced microbicidal activity, regulatory macrophages are characterized by the production of high levels of the anti-inflammatory cytokine IL-10 and low levels of the pro-inflammatory molecule IL-12p40[4]. The regulatory macrophages are thought to be crucial for the resolution of the inflammatory response and we found that treatment of quiescent macrophages with MRT67307 or KIN112 switched their maturation programme from the classically activated route towards the regulatory phenotype, since they now secreted high levels of IL-10 and low levels of IL-12p40 in response to TLR ligands, as well as stimulating the production of other mRNAs that encode characteristic markers of regulatory macrophages. These include arginase-1, sphingosine kinase-1 and TNF receptor ligand superfamily member 14 (TNFSM14), also called LIGHT, Lymphotoxin like)[4,24] (FIG. 4E). Moreover, these inhibitors also greatly increased the production of the mRNA encoding the anti-inflammatory molecule IL-1 receptor antagonist (IL-1ra). Thus, inhibition of the SIKs appears to drive the maturation of regulatory macrophages, which should in turn facilitate resolution of the inflammatory response by activating CREB-dependent gene transcription. Our studies raise the intriguing possibility that the level of expression or activity of SIKs and/or CRTCs in macrophages or other immune cells may be an important factor in determining predisposition to inflammatory and autoimmune diseases The treatment of inflammatory diseases still relies primarily on the use of anti-inflammatories, such as glucocorticoids, or broad spectrum immunosuppressants, but these therapies have multiple side-effects due to the non-selective nature of these treatments, while many patients become resistant to glucocorticoids[25,26]. Neutralizing antibodies that inhibit the actions of particular pro-inflammatory cytokines, such as the anti-TNFα Humira, are having a major impact on the treatment of rheumatoid arthritis and other inflammatory diseases, but these therapies are very expensive and only half the patients are good responders[27]. The anti-inflammatory properties of IL-10 are currently being exploited in an attempt to develop therapeutics for psoriasis, Crohn's, rheumatoid arthritis and other diseases, but results in the clinic using recombinant IL-10 have been disappointing, perhaps because elevated levels of IL-10 are required locally rather than systemically and/or because the presence of additional anti-inflammatory molecules is also required[28,29]. For these reasons, there is undiminished interest in developing orally available drugs to treat chronic inflammatory and autoimmune diseases. By simultaneously activating several anti-inflammatory pathways and inhibiting production of pro-inflammatory pathways, the inhibition of SIKs may provide an advantage over current therapies and lead to the development of improved drugs to treat these disorders.

REFERENCES

1 Kawai, T. & Akira, S. The role of pattern-recognition receptors in innate immunity: update on Toll-like receptors. *Nat Immunol* 11, 373-384 (2010).
2 Ewald, S. E. & Barton, G. M. Nucleic acid sensing Toll-like receptors in autoimmunity. *Curr Opin Immunol* 23, 3-9 (2011).
3 Santegoets, K. C., van Bon, L., van den Berg, W. B., Wenink, M. H. & Radstake, T. R. Toll-like receptors in rheumatic diseases: Are we paying a high price for our defense against bugs? *FEBS Lett* 585, 3660-3666 (2011).
4 Mosser, D. M. & Edwards, J. P. Exploring the full spectrum of macrophage activation. *Nat Rev Immunol* 8, 958-969 (2008).
5 Clark, K. et al. Novel cross-talk within the IKK family controls innate immunity. *Biochem J* 434, 93-104 (2011).
6 Clark, K., Takeuchi, O., Akira, S. & Cohen, P. The TRAF-associated protein TANK facilitates cross-talk within the IkB kinase family during Toll-like receptor signaling. *Proc Natl Acad Sci USA* 108, 17093-17098 (2011).
7 Ghoreschi, K., Laurence, A. & O'Shea, J. J. Janus kinases in immune cell signaling. *Immunol Rev* 228, 273-287 (2009).
8 Kuhn, R., Lohler, J., Rennick, D., Rajewsky, K. & Muller, W. Interleukin-10-deficient mice develop chronic enterocolitis. *Cell* 75, 263-274 (1993).
9 Saraiva, M. & O'Garra, A. The regulation of IL-10 production by immune cells. *Nat Rev Immunol* 10, 170-181 (2010).
10 Fitzgerald, K. A. et al. IKKepsilon and TBK1 are essential components of the IRF3 signaling pathway. *Nat Immunol* 4, 491-496 (2003).
11 Sharma, S. et al. Triggering the interferon antiviral response through an IKK-related pathway. *Science* 300, 1148-1151 (2003).
12 Hemmi, H. et al. The roles of two IkappaB kinase-related kinases in lipopolysaccharide and double stranded RNA signaling and viral infection. *J Exp Med* 199, 1641-1650 (2004).
13 McWhirter, S. M. et al. IFN-regulatory factor 3-dependent gene expression is defective in Tbk1-deficient mouse embryonic fibroblasts. *Proc Natl Acad Sci USA* 101, 233-238 (2004).
14 Perry, A. K., Chow, E. K., Goodnough, J. B., Yeh, W. C. & Cheng, G. Differential requirement for TANK-binding kinase-1 in type I interferon responses to toll-like receptor activation and viral infection. *J Exp Med* 199, 1651-1658 (2004).
15 Ananieva, O. et al. The kinases MSK1 and MSK2 act as negative regulators of Toll-like receptor signaling. *Nat Immunol* 9, 1028-1036 (2008).
16 Altarejos, J. Y. & Montminy, M. CREB and the CRTC co-activators: sensors for hormonal and metabolic signals. *Nat Rev Mol Cell Biol* 12, 141-151 (2011).
17 Jansson, D. et al. Glucose controls CREB activity in islet cells via regulated phosphorylation of TORC2. *Proc Natl Acad Sci USA* 105, 10161-10166 (2008).
18 Mair, W. et al. Lifespan extension induced by AMPK and calcineurin is mediated by CRTC-1 and CREB. *Nature* 470, 404-408 (2011).
19 Screaton, R. A. et al. The CREB coactivator TORC2 functions as a calcium- and cAMP-sensitive coincidence detector. *Cell* 119, 61-74 (2004).
20 Clark, K., Plater, L., Peggie, M. & Cohen, P. Use of the pharmacological inhibitor BX795 to study the regulation and physiological roles of TBK1 and IkappaB kinase epsilon: a distinct upstream kinase mediates Ser-172 phosphorylation and activation. *J Biol Chem* 284, 14136-14146 (2009).
21 Eyers, P. A., Craxton, M., Morrice, N., Cohen, P. & Goedert, M. Conversion of SB 203580-insensitive MAP kinase family members to drug-sensitive forms by a single amino-acid substitution. *Chem Biol* 5, 321-328 (1998).
22 Liu, Y., Shah, K., Yang, F., Witucki, L. & Shokat, K. M. Engineering Src family protein kinases with unnatural nucleotide specificity. *Chem Biol* 5, 91-101 (1998).
23 Lizcano, J. M. et al. LKB1 is a master kinase that activates 13 kinases of the AMPK subfamily, including MARK/PAR-1. *EMBO J* 23, 833-843 (2004).
24 Benoit, M., Desnues, B. & Mege, J. L. Macrophage polarization in bacterial infections. *J Immunol* 181, 3733-3739 (2008).
25 Hahn, B. H. Targeted therapies in systemic lupus erythematosus: successes, failures and future. *Ann Rheum Dis* 70 Suppl 1, i64-i66 (2011).
26 Triantafillidis, J. K., Merikas, E. & Georgopoulos, F. Current and emerging drugs for the treatment of inflammatory bowel disease. *Drug Des Devel Ther* 5, 185-210 (2011).
27 Kopf, M., Bachmann, M. F. & Marsland, B. J. Averting inflammation by targeting the cytokine environment. *Nat Rev Drug Discov* 9, 703-718 (2010).
28 Mosser, D. M. & Zhang, X. Interleukin-10: new perspectives on an old cytokine. *Immunol Rev* 226, 205-218 (2008).
29 O'Garra, A., Barrat, F. J., Castro, A. G., Vicari, A. & Hawrylowicz, C. Strategies for use of IL-10 or its antagonists in human disease. *Immunol Rev* 223, 114-131 (2008).
30 Pfaffl, M. W. A new mathematical model for relative quantification in real-time RT-PCR. *Nucleic Acids Res* 29, e45 (2001).
31 McNulty, D. E. & Annan, R. S. Hydrophilic interaction chromatography reduces the complexity of the phosphoproteome and improves global phosphopeptide isolation and detection. *Mol Cell Proteomics* 7, 971-980 (2008).
32 Navarro, M. N., Goebel, J., Feijoo-Carnero, C., Morrice, N. & Cantrell, D. A. Phosphoproteomic analysis reveals an intrinsic pathway for the regulation of histone deacetylase 7 that controls the function of cytotoxic T lymphocytes. *Nat Immunol* 12, 352-361 (2011).
33 Cox, J. et al. A practical guide to the MaxQuant computational platform for SILAC-based quantitative proteomics. *Nat Protoc* 4, 698-705 (2009).

Further evidence in support of the present invention particularly in relation to the use of the compound HG-9-91-01, is provided in Clark et al (PNAS, 109, 2012 p16986-16991), the contents of which are hereby incorporated herein in their entirety by way of reference. Relevant parts of the paper are presented below and in the figures:

Materials and Methods

Materials

Protein kinase inhibitors were dissolved in DMSO and stored at −20° C. as 10 mM solutions. The TLR agonists Pam$_3$CSK$_4$, LTA, poly(I:C), R837 and CpG (ODN1826) were from Invivogen and LPS (*E. coli* 055:135) from Alexis Biochemicals. Mouse IL-1α was obtained from Sigma. Mouse and human recombinant M-CSF was purchased from R&D Systems. Murine IL-4 and IFNγ were from Peprotech.

Macrophages were treated for 1 h with inhibitors (2 μM MRT67307, 1 μM MRT199665, 500 nM HG-9-91-01, 10 μM KIN112), or an equivalent volume of DMSO for control incubations then stimulated for up to 24 h with either 1 μg/ml Pam3CSK4, 2 μg/ml LTA, 10 μg/ml poly(I:C), 100 ng/ml LPS, 1 μg/ml R837 or 2 μM CpG. Proteins were extracted and immunoblotted as described previously (Clark K, et al. (2011) Novel cross-talk within the IKK family controls innate immunity. Biochem J 434:93-104) using the indicated antibodies. RNA was extracted using the RNeasy Micro Kit (Qiagen). cDNA was generated using the iScript cDNA synthesis kit and quantified by qPCR using the SsoFast EvaGreen Supermix (Bio-Rad Laboratories). The relative expression of each gene was calculated from Ct values using the Pfaffl method (Pfaffl M W (2001) A new mathematical model for relative quantification in real-time RT-PCR. Nucleic Acids Res 29:e45) and was normalized against the mRNA levels of 18S or GAPDH RNA. Fold-induction for each gene was reported relative to untreated control cells, which was set to 1. The concentrations of TNFα, IL-6, IL-10, IL-12p40, and RANTES in culture supernatants were measured using the Bio-Plex Pro Assay system from Bio-Rad. Further details in supplementary information.

Chemical Synthesis

MRT67307 was synthesized as described (1). KIN112 is compound 28 in the article by Martin et al. (2) and was synthesized according to the authors' instructions. To generate MRT199665, 7-[(1S)-4-hydroxy-2,3-dihydro-1H-inden-1-yl]-5,5-dimethyl-2-(methylsulfonyl)-5,7-dihydro-6H-pyrrolo[2,3-d]pyrimidin-6-one was synthesized as previously reported (3). This intermediate (75 mg, 0.2 mmol) and 3-(pyrrolidin-1-ylmethyl)aniline (106 mg, 0.6 mmol) were added to NMP (0.5 ml), and the resulting mixture was irradiated for 1 h at 180° C. in a Biotage 1-60 microwave reactor. The mixture was cooled, filtered and the filtrate was purified by preparative LCMS {HPLC column: 4.6×50 mm (5 μm) C-18 Xbridge; flow rate: 3 ml/min; Run time: 3.2 min: Solvent A: 0.1% Ammonium Hydroxide in water; Solvent B: Methanol; Gradient: 10-100% B; Gradient time: 2.35 min. HPLC retention time (2.15 min)} to give a brown solid (20 mg, 21%). $^1$H NMR (400 MHz, DMSO-d$_6$) δ p.p.m. 9.45 (s, 1H), 9.40 (s, 1H), 8.23 (s, 1H), 7.17-7.57 (m, 2H), 7.12 (t, J=7.8 Hz, 1H), 6.87-7.00 (m, 1H), 6.80 (d, J=7.3 Hz, 1H), 6.66 (d, J=8.2 Hz, 1H), 6.42 (d, J=7.3 Hz, 1H), 5.86 (t, J=8.70 Hz, 1H), 3.40-3.52 (m, 2H), 2.99-3.17 (m, 1H), 2.73-2.93 (m, 1H), 2.56-2.71 (m, 1H), 2.26-2.44 (m, 5H), 1.53-1.74 (m, 4H), 1.15-1.50 (m, 6H); $^{13}$C NMR (101 MHz, CDCl$_3$) δ p.p.m. 181.42, 162.93, 158.74, 153.15, 148.47, 142.40, 139.18, 138.55, 129.86, 128.99, 128.10, 123.46, 120.00, 118.28, 117.46, 114.64, 60.53, 56.02, 54.07, 42.48, 28.10, 27.23, 24.71, 24.04, 23.18; HRMS (m/z): [M+H]$^+$ calculated for C$_{28}$H$_{31}$N$_5$O$_2$, 470.2551; found 470.2547.

Synthesis of HG-9-91-01

The urea formation was performed using a Biotage® Initiator$^+$ Microwave Synthesizer. All reactions were monitored by thin layer chromatography (TLC) with 0.25 mm E. Merck pre-coated silica gel plates (60 F$_{254}$) and Waters LCMS system (Waters 2489 UV/Visible Detector, Waters 3100 Mass, Waters 515 HPLC pump, Waters 2545 Binary Gradient Module, Waters Reagent Manager, Waters 2767 Sample Manager) using SunFire™ C18 column (4.6×50 mm, 5 μm particle size): solvent gradient=100% A at 0 min, 1% A at 5 min; solvent A=0.035% TFA in Water; solvent B=0.035% TFA in MeOH; flow rate: 2.5 mL/min. Purification of reaction products was carried out by flash chromatography using CombiFlash®Rf with Teledyne Isco RediSep®Rf High Performance Gold or Silicycle SiliaSep™ High Performance columns (4 g, 12 g, 24 g, 40 g, or 80 g) and Waters LCMS system using SunFire™ Prep C18 column (19×50 mm, 5 μm particle size): solvent gradient=80% A at 0 min, 10% A at 8 min; solvent A=0.035% TFA in Water; solvent B=0.035% TFA in MeOH; flow rate: 25 mL/min. The purity of all compounds was over 95% and was analyzed with Waters LCMS system. $^1$H NMR and $^{13}$C NMR spectra were obtained using a Varian Inova-600 (600 MHz for $^1$H, and 125 MHz for $^{13}$C) spectrometer. Chemical shifts are reported relative to chloroform (δ=7.24) for $^1$H NMR or dimethyl sulfoxide (δ=2.50) for $^1$H NMR and dimethyl sulfoxide (δ=39.51) for $^{13}$C NMR. Data are reported as (br=broad, s=singlet, d=doublet, t=triplet, q=quartet, m=multiplet).

Scheme of HG-9-91-01

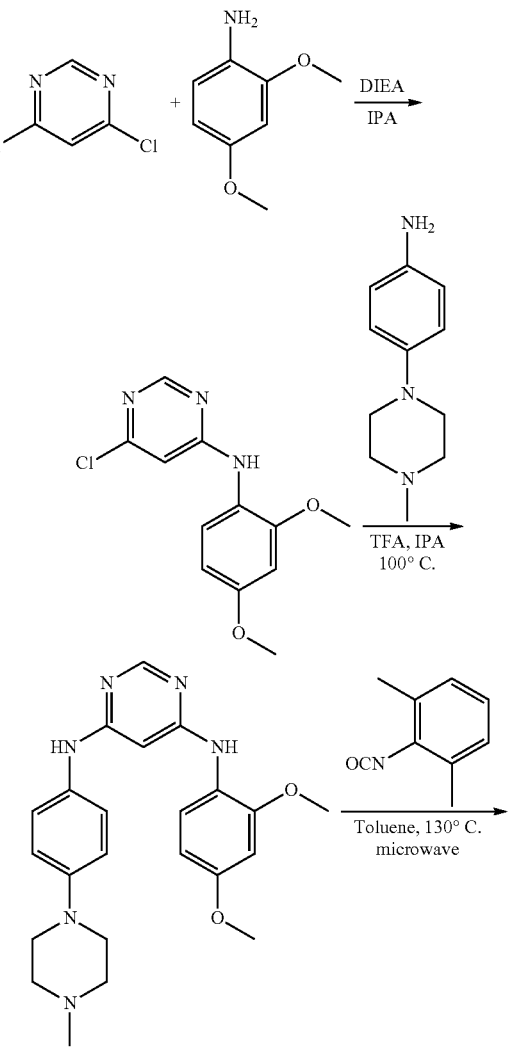

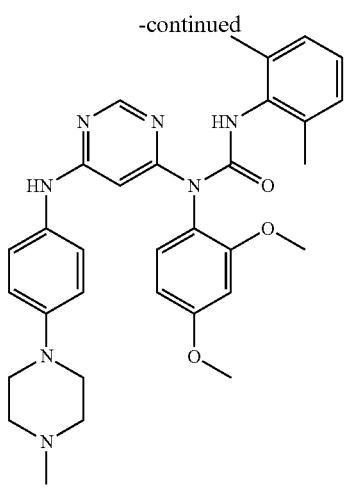

Synthesis of HG-9-91-01

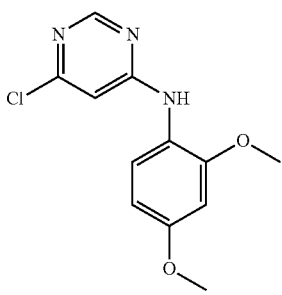 [SMILES: COc1ccc(Nc2cc(Cl)ncn2)c(OC)c1]

6-chloro-N-(2,4-dimethoxyphenyl)pyrimidin-4-amine

To a solution of 4,6-dichloropyrimidine (1.2 g, 8.11 mmol) in 2-propanol (34 mL) was added 2,4-dimethoxyaniline (1.03 g, 6.75 mmol) and N,N-diisopropylethylamine (2.82 ml, 16.22 mmol). The reaction mixture was stirred at 50° C. for 24 hrs and partitioned between ethyl acetate and saturated aqueous sodium bicarbonate solution. The organic layer was washed with brine, dried over MgSO₄, filtered through a pad of celite and concentrated under reduced pressure. The residue was purified by column chromatography on silica gel (1:9 to 3:7, ethyl acetate/hexane) to afford 6-chloro-N-(2,4-dimethoxyphenyl)pyrimidin-4-amine (1.4 g, 78% yield) as an off-white solid. Rt=3.80 min; $^1$H NMR 600 MHz (CDCl3) δ 8.39 (s, 1H), 7.44 (bs, 1H), 7.37 (bs, 1H), 6.49-6.52 (m, 3H), 3.81 (m, 6H); $^1$H NMR 600 MHz (DMSO-$d_6$) δ 9.02 (s, 1H), 8.23 (s, 1H), 7.36 (bs, 1H), 6.60 (d, J=2.4 Hz, 1H), 6.47 (m, 1H), 3.68 (m, 6H); MS m/z: 266.13 [M+1].

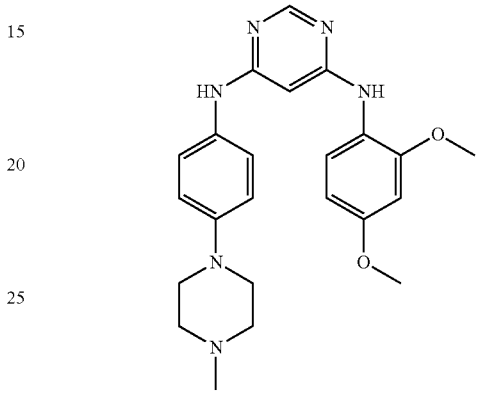

N4-(2,4-dimethoxyphenyl)-N6-(4-(4-methylpiperazin-1-yl)phenyl)pyrimidine-4,6-diamine To a solution 6-chloro-N-(2,4-dimethoxyphenyl)pyrimidin-4-amine (1.0 g, 3.77 mmol) in 2-butanol (9 mL) and trifluoroacetic acid (1 mL) was added 4-(4-methylpiperazin-1-yl)aniline (685 mg, 3.58 mmol, AK Scientific). The reaction mixture was stirred at 100° C. for 24 hrs and the solvent concentrated under reduced pressure. The reaction mixture was diluted with dichloromethane and washed with saturated aqueous potassium carbonate solution and brine. The organic layer was dried over MgSO₄, filtered through a pad of celite and concentrated under reduced pressure. The residue was purified by column chromatography on silica gel (1:99 to 3:97, ammonia solution 7.0 N in methanol/dichloromethane) to afford N4-(2,4-dimethoxyphenyl)-N6-(4-(4-methylpiperazin-1-yl)phenyl)pyrimidine-4,6-diamine (1.2 g, 80% yield) as an off-white solid. Rt=2.18 min; $^1$H NMR 600 MHz (DMSO-$d_6$) δ 8.67 (s, 1H), 8.05 (s, 1H), 8.01 (s, 1H), 7.36 (d, J=8.4 Hz, 1H), 7.30 (d, J=8.4 Hz, 2H), 6.87 (d, J=9.6 Hz, 2H), 6.63 (d, J=3.0 Hz, 1H), 6.51 (dd, J=9.0 Hz, J=3.0 Hz, 1H), 5.70 (s, 1H), 3.77 (s, 3H), 3.75 (s, 3H), 3.08 (m, 4H), 2.56 (m, 4H), 2.30 (s, 3H); $^{13}$C NMR 125 MHz (DMSO-$d_6$) δ 161.87, 160.80, 157.45, 157.31, 153.76, 146.20, 132.56, 126.40, 121.45, 120.93, 116.07, 104.38, 99.17, 83.76, 73.71, 55.56, 55.32, 54.26, 48.36, 45.13; MS m/z: 421.45 [M+1].

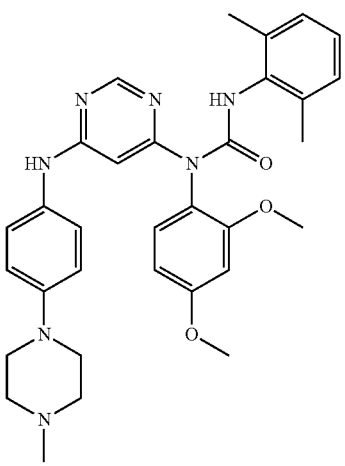 [SMILES: COc1ccc(N(C(=O)Nc2c(C)cccc2C)c2cc(Nc3ccc(N4CCN(C)CC4)cc3)ncn2)c(OC)c1]

1-(2,4-di methoxyphenyl)-3-(2,6-di methyl phenyl)-
1-(6-((4-(4-methylpiperazin-1-yl)phenyl)amino)py-
rimidin-4-yl)urea (HG-9-91-01)

A 5 mL microwave vial was charged with N4-(2,4-dimethoxyphenyl)-N6-(4-(4-methylpiperazin-1-yl)phenyl) pyrimidine-4,6-diamine (200 mg, 0.47 mmol), 2,6-dimethylphenyl isocyanate (345 mg, 2.35 mmol) and toluene (2 mL). The reaction vial was sealed and heated at 130° C. for 1 h. To a reaction vial was additionally added 2,6-dimethylphenyl isocyanate (345 mg, 2.35 mmol) and heated at 130° C. for 1 h. Two regioisomers, 1-(2,4-dimethoxyphenyl)-3-(2,6-dimethylphenyl)-1-(6-((4-(4-methylpiperazin-1-yl) phenyl)amino)pyrimidin-4-yl)urea and 1-(6-((2,4-dimethoxyphenyl)amino)pyrimidin-4-yl)-3-(2,6-dimethylphenyl)-1-(4-(4-methylpiperazin-1-yl)phenyl)urea were generated in a ratio of 4:1 by HPLC analysis. The reaction mixture was concentrated under reduced pressure. The residue was purified by column chromatography on silica gel (1:99 to 7:93, methanol/dichloromethane) and additionally purified with HPLC to afford 1-(2,4-dimethoxyphenyl)-3-(2,6-dimethylphenyl)-1-(6-((4-(4-methylpiperazin-1-yl)phenyl)amino)pyrimidin-4-yl)urea (90 mg, 34% yield) as an off-white solid. Rt=3.30 min; $^1$H NMR 600 MHz (DMSO-$d_6$) δ 11.54 (s, 1H), 9.19 (s, 1H), 8.38 (s, 1H), 7.29 (m, 2H), 7.15 (d, J=9.0 Hz, 1H), 7.07 (m, 3H), 6.85 (d, J=8.4 Hz, 2H), 6.74 (d, J=2.4 Hz, 1H), 6.63 (dd, J=8.4 Hz, J=2.4 Hz, 1H), 5.70 (s, 1H), 3.82 (s, 3H), 3.74 (s, 3H), 3.05 (m, 4H), 2.44 (m, 4H), 2.23 (s, 6H), 2.22 (s, 3H); $^{13}$C NMR 125 MHz (DMSO-$d_6$) δ 161.24, 160.34, 160.28, 156.51, 156.03, 152.59, 146.88, 135.46, 134.90, 131.38, 127.64, 125.99, 121.43, 120.62, 115.76, 105.42, 99.68, 55.75, 55.41, 48.57, 45.68, 18.30; MS m/z: 568.51 [M+1]

1-(6-((2,4-dimethoxyphenyl)amino)pyrimidin-4-yl)-
3-(2,6-di methyl phenyl)-1-(4-(4-methylpiperazin-1-
yl)phenyl)urea Rt=3.55 min; $^1$H NMR 600 MHz (DMSO-$d_6$) δ 11.67 (s, 1H), 8.70 (s, 1H), 8.31 (s, 1H), 7.26 (bs, 1H), 7.05 (m, 5H), 7.01 (d, J=9.0 Hz, 2H), 6.53 (d, J=3 Hz, 1H), 6.44 (dd, J=7.8 Hz, J=3.0 Hz, 1H), 3.73 (s, 3H), 3.70 (s, 3H), 3.19 (m, 4H), 2.54 (m, 4H), 2.29 (s, 3H), 2.23 (s, 6H); $^{13}$C NMR 125 MHz (DMSO-$d_6$) δ 162.15, 160.87, 155.76, 152.98, 150.12, 135.43, 134.78, 130.34, 129.90, 127.68, 126.37, 125.99, 115.96, 104.23, 98.83, 55.45, 55.29, 47.68, 45.42, 18.44; MS m/z: 568.45 [M+1]

Constructs

CRTC3 (NCBI AY360173.1) was amplified from brain mRNA using Superscript one step RT-PCR system (Life Technologies). The product was cloned into PCR2.1 (Life Technologies), sequenced to completion and then cloned into pCMVFLAG-1 using EcoRI and NotI or into pRetro-X-Tight (Clontech) using EcoRI. pBABEpuroGFP-CRTC3 was created by amplifying CRTC3 using KOD Hot Start DNA Polymerase (Novagen) and subcloned into the XhoI and NotI sites of pBABEpuroGFP. GST-SIK1, SIK2 and SIK3 constructs were described previously (4). HA-SIK2 in pRetro-X-Tight was generated by amplifying the SIK2 cDNA by PCR with oligos containing sequences encoding the HA-tag. The PCR product was cloned into pCR2.1, sequenced to completion and then transferred into the NotI site of pRetro-X-tight. CRTC2 (NCBI NM_181715) was amplified from IMAGE clone 6188068 and subcloned intro the EcoRI site of pCMVFLAG-1. Mutants were created using the Quickchange method (Agilent) but using KOD Hot Start DNA Polymerase (Novagen). pRetroX-Tet-On-Advanced vector and Retro-X Universal Packaging mix were from Clontech. The lentiviral vector PLKO.1 containing shRNA oligos targeting SIK1 (TRCN0000274520), SIK2 (TRCN0000024288), SIK3 (TRCN0000079130) and the negative control (SHC001) as well as the Mission Lentiviral Packaging Mix were purchased from Sigma.

Mice

IL-10$^{-/-}$ mice on a C57BL/6 background were purchased from The Jackson Laboratory, Maine, USA. LKB1$^{flox/flox}$ mice on a C57BL/6 background were a generous gift from Alan Ashworth and were crossed with LysM-Cre mice to delete LKB1 in macrophages. Mice were bred at the University of Dundee under specific pathogen-free conditions in accordance with European Union regulations. Water supply for IL-10$^{-/-}$ mice was supplemented with antibiotics to prevent the development of colitis. Work was approved by local ethical review and was performed with a UK Home Office project license.

Cell Culture

Bone marrow-derived macrophages were differentiated for 7 days in DMEM supplemented with 5 ng/ml recombinant M-CSF (R&D systems), 2 mM glutamine, 10% foetal calf serum (FCS), penicillin and streptomycin. RAW264.7 cells and immortalized mouse embryonic fibroblasts (MEFs) from TBK1/IKKε$^{+/-}$, TBK1/IKKε$^{-/-}$, LKB1$^{+/+}$ and LKB1$^{-/-}$ mice were cultured in DMEM containing 10% FCS, 2 mM glutamine and penicillin and streptomycin, while THP-1 monocytes were grown in RPMI-1640 supplemented with 10% FCS and antibiotics. For the culture of primary human macrophages, PBMCs were isolated from human blood using Ficoll and the monocytes were purified using anti-CD14 magnetic beads (Miltenyi Biotec). Monocytes were differentiated into macrophages for 6 days in the presence of 100 ng/ml M-CSF. Cells were treated for 1 h without or with inhibitors (2 μM MRT67307, 1 μM MRT199665, 10 μM KIN112, 500 nM HG-9-91-01) then stimulated for up to 24 h with either 1 μg/ml Pam$_3$CSK$_4$, 2 μg/ml LTA, 10 μg/ml poly(I:C), 100 ng/ml LPS, 1 μg/ml R837 or 2 μM CpG.

Retroviral Transduction of RAW264.7 Cells

RAW264.7 cells stably expressing CRTC3 and SIK2 were generated by retroviral transduction using a Murine Moloney Leukemia virus-based system prepared with VSV-G envelope protein. Retrovirus particles were prepared according to the manufacturer's instructions (Clontech). Viruses encoding the gene of interest and the Tet-On protein were harvested 48 h post-transfection, diluted 4-fold with fresh media and incubated with RAW264.7 cells in the presence of 2 µg/ml protamine sulfate (Sigma) for 24 h. Fresh media containing 1 mg/ml G418 (Tet-On) and 3 µg/ml puromycin (gene of interest) was added to select the transduced cells. To induce gene expression, cells were cultured in the presence of 20-1000 ng/ml doxycyclin for 8-24 h.

RNAi in Macrophages RAW264.7 cells or BMDMs were transfected with 100 pmol of SMARTpool siRNA oligos against CREB, CRTC1, CRTC2, CRTC3 or a non-targetting control (Dharmacon) using AMAXA nucleofection. Cells were cultured for 24 h prior to incubation with inhibitors for 1 h followed by stimulation for 1 h with 100 ng/ml LPS. Gene expression was measured by real-time quantitative PCR. For shRNA knockdown of SIKs, lentivirus was generated according to the manufacturer's instructions (Sigma) and RAW264.7 cells were infected using virus harvested 48 and 72 h post-transfection. Infected cells were selected using 3 µg/ml puromycin.

QPCR mRNA was extracted from cells using the RNeasy Micro Kit following the manufacturers' instructions (Qiagen). cDNA was generated from 1 µg of total RNA using the iScript cDNA synthesis kit and quantified by qPCR using the SsoFast EvaGreen Supermix on a CFX96 real time system (Bio-Rad Laboratories). The relative expression of each gene was calculated from Ct values using the Pfaffl method (5) and was normalized against the mRNA levels of 18S RNA or GAPDH. Results are reported relative to untreated control cells, which was set to 1. The following primers were used:

```
IL-10-F,   CCCTTTGCTATGGTGTCCTTTC;
IL-10-R,   GATCTCCCTGGTTTCTCTTCCC;
c-Fos-F,   CTACTGTGTTCCTGGCAATAGC;
c-Fos-R,   AACATTGACGCTGAAGGACTAC;
Nurr1-F,   GAAGAGAGCGGACAAGGAGATC;
Nurr1-R,   AAGGCATGGCTTCAGCAGAG;
Nurr77-F,  CCTGTTGCTAGAGTCTGCCTTC;
Nurr77-R,  CAATCCAATCACCAAAGCCACG;
18S-F,     GTAACCCGTTGAACCCCATT;
18S-R,     CCATCCAATCGGTAGTAGCG;
IL-1ra-F,  TCCTTTATACACAGCAAGTCTC;
IL-1ra-R,  TTCTGAAGGCTTGCATCTTG;
SPHK1-F,   ACAGCAGTGTGCAGTTGATGA;
SPHK1-R,   GGCAGTCATGTCCGGTGATG;
LIGHT-F,   CTGCATCAACGTCTTGGAGA;
LIGHT-R,   GATACGTCAAGCCCCTCAAG;
Arg1-F,    CTCCAAGCCAAAGTCCTTAGAG
Arg1-R,    AGGAGCTGTCATTAGGGACATC;
FIZZ-F,    CCCAGGATGCCAACTTTGAA;
FIZZ-R,    GGCCCATCTGTTCATAGTCT;
Mgl2-F,    TTAGCCAATGTGCTTAGCTGG;
Mgl2-R,    GGCCTCCAATTCTTGAAACCT;
YM1-F,     AGAAGGGAGTTTCAAACCTGGT;
YM1-R,     GTCTTGCTCATGTGTGTAAGTGA;
SIK1-F,    ACAGCACCACTCTTCTACCGC;
SIK1-R,    TCACAGGGAGCAAGCACATAGG;
SIK2-F,    TTAATGAGCAGGTTCTTC;
SIK2-R,    AAATAAATGGCAGCAAAG;
SIK3-F,    CAGGTTAATAGCGGAGTG;
SIK3-R,    ATAGCCAAGAGGACATCA;
CRTC1-F,   ACTCAAAGAAGGCGGGTTCC;
CRTC1-R,   TGGGTGGCAGGGATCAGG;
CRTC2-F,   TGCGACTGGCTTATACAAGG;
CRTC2-R,   GAGTGCTCCGAGATGAATCC;
CRTC3-F,   AGCCATCACTTCATCAAGC;
CRTC3-R,   ATTCCCATCAAACTGTCTCC;
GAPDH-F,   GCCTTCCGTGTTCCTACCC;
GAPDH-R,   TGCCTGCTTCACCACCTTC;
Human IL-10-F,   ACCTTATTGTACCTCTCTTAT;
Human IL-10-R,   GGGCTTCTTTCTAAATCG;
Human TNFα-F,    CATCCAACCTTCCCAAA;
Human TNFα-R,    GGTGGTCTTGTTGCTTA;
Human Nurr77-F,  GGAGAGTTTGACACCTT;
Human Nurr77-R,  TACACCTGGAAGTCCTC;
Human GAPDH-F,   TTAACTCTGGTAAAGTGGAT;
Human GAPDH-R,   ACTTGATTTTGGAGGGAT;
```

Cytokine Secretion

Following stimulation with ligands, the cell culture medium was removed, clarified by centrifugation for 10 min at 14000×g and the concentration of TNFα, IL-6, IL-10, IL-12p40 and RANTES were measured using the Bio-Plex Pro Assay system from Bio-Rad. IL-1ra and IFNβ were measured using ELISA kits from R&D Systems.

Luciferase Assays

HEK293 cells were co-transfected with DNA encoding FLAG-CRTC3 or phosphomutants along with a CREB firefly luciferase reporter construct (pCRE-luc from Stratagene) and pTK-RL which encodes renilla luciferase under the control of a constitutive promoter. At 24 h post-transfection, cells were treated with or without 10 µM KIN112 for a further 24 h. Firefly luciferase activity was measured with a dual luciferase assay system (Promega) and was normalized to Renilla luciferase activity.

Immunoblotting

Cells were rinsed in ice-cold PBS and extracted in lysis buffer (50 mM Tris/HCl pH 7.4, 1 mM EDTA, 1 mM EGTA, 50 mM NaF, 5 mM sodium pyrophosphate, 10 mM sodium β-glycerol 1-phosphate, 1 mM dithiothreitol, 1 mM sodium orthovanadate, 0.27 M sucrose, 1% (v/v) Triton X-100, 1 µg/ml aprotinin, 1 µg/ml leupeptin and 1 mM phenylmethylsulphonyl fluoride). Cell extracts were clarified by centrifugation at 14000×g for 10 min at 4° C. and protein concentrations were determined using the Bradford assay. FLAG-CRTC3 was purified on anti-FLAG M2 agarose whereas endogenous CRTC3 was immunoprecipitated from cell extracts using anti-CRTC3 raised against the peptide CWKEEKHPGFR (S277D bleed 2) and coupled to Protein G-Sepharose. To detect proteins in cell lysates, 20 µg of protein extract was separated by SDS-PAGE. After transfer to PVDF membranes, proteins were detected by immunoblotting and visualized by treating the blots with ECL (Amersham) followed by autoradiography. The following antibodies were used for immunoblotting: pSer133 CREB, pSer171 CRTC2, total CRTC2, GAPDH, total STAT3 and pTyr705 STAT3 were purchased from Cell Signaling Technology; FLAG (M2 clone) was obtained from Sigma; CRTC3 was from Abcam; HA (3F10) was from Roche, 14-3-3 was obtained from Santa Cruz and antibodies against pSer329 (S256D bleed 2) and pSer370 (S253D bleed 2) of CRTC3 were raised against the phosphopeptides GLQSSRpSNPSIQ and RLFSLpSNPSLST in sheep and purified by affinity chromatography in the Division of Signal Transduction Therapy, University of Dundee.

Immunofluorescence

RAW264.7 cells were grown on glass coverslips and treated with inhibitors for 1 h. Cells were then fixed for 10 min in 3.7% paraformaldehyde, permeabilized for 5 min using 0.1% Triton X-100 in PBS and blocked for 45 min using 3% BSA in PBS. Cells were stained with anti-CRTC3 (Abcam 1:200) and anti-α-tubulin (Santa Cruz 1:500) followed by anti-rabbit-alexa488 and anti-mouse-alexa594 (Invitrogen 1:500), respectively. Antibodies were diluted in blocking buffer and incubated with the cells for 45 min. Cells were mounted in Prolong Gold Antifade Reagent containing DAPI (Invitrogen) and visualized under a Nikon Eclipse-Ti-S microscope equipped with a 60×/1.4 oil-immersion lens. For live imaging, RAW264.7 cells were transduced with MMLV-based retroviral vectors encoding GFP-CRTC3 or GFP-CRTC3[S62A/S162A/S329A/S370A] and plated onto glass-bottom dishes. Cells were imaged on a Zeiss LSM 700 confocal microscope equipped with a ×100 Plan Apochromat NA 1.46 lens. Images were recorded every 30 s for 1.5 min prior to the addition of drug after which cells were imaged for a further 60 min.

Kinase Assays

Recombinant SIK1, SIK2, SIK3 were expressed as GST-fusion proteins in HEK293 cells and purified on a glutathione-Sepharose column. To purify dephosphorylated CRTC3, FLAG-CRTC3 was co-expressed with lambda phosphatase in HEK293 cells which were also treated for 1 h with 2 µM MRT67307 prior to cell lysis. FLAG-CRTC3 was immunoprecipitated using anti-FLAG M2 agarose, washed in kinase buffer (50 mM Tris/HCl pH 7.4, 10 mM Mg acetate, 0.1 mM EGTA, 2 mM DTT) and reactions initiated by adding 4 U/ml recombinant kinase with 0.1 mM ATP (specific activity 3000 cpm/pmol). Phosphorylation of CRTC3 was monitored by autoradiography as well as immunoblotting using phosphospecific antibodies raised against Ser162, Ser329 and Ser370. For the 1050 curve measurements, kinase assays were performed as described by Hastie and colleagues (6) but using a peptide derived from sequences surrounding Ser171 of CRTC2 (ALNRTSSD-SALHRRR) as a substrate. Kinase profiling was performed as previously described (7) and performed by the International Centre for Kinase Profiling (www.kinase-screen.mr-c.ac.uk).

14-3-3 Binding Assay

CRTC3 was immunoprecipitated from cell extracts, resolved by SDS-PAGE and transferred onto PVDF membrane. The membrane was incubated with purified yeast 14-3-3 that had been coupled to digoxygenin (DIG) (1 µg/ml) overnight. An interaction with 14-3-3 was detected by subsequently incubating the membrane with anti-DIG-horseradish peroxidase conjugate followed by ECL and autoradiography.

Phosphoproteomics

RAW264.7 cells were labelled using the Stable Isotope Labelling of Amino Acids in Cell Culture (SILAC) method. Cells were treated for 1 h with 2 µM MRT67307 or vehicle control and subsequently, left unstimulated or stimulated for 30 min with 1 µg/ml $Pam_3CSK_4$. The cells were lysed in detergent-free lysis buffer (50 mM Tris/HCl pH 8.2, 10 mM glycerol 2-phosphate, 50 mM sodium fluoride, 5 mM sodium pyrophosphate, 1 mM EDTA, 1 mM sodium orthovanadate, 10 mM DTT, 1 mM PMSF, 1 mg/ml aprotinin, 1 mg/ml leupeptin) containing 8 M urea, the extract clarified by centrifugation and protein concentrations determined using the Bradford method. 2 mg of cell extract protein from each experimental condition were mixed in a 1:1:1 ratio and then alkylated for 30 min with 50 mM iodoacetamide. The sample was diluted with 0.1 M ammonium bicarbonate to a final urea concentration of 1.5 M and the proteins were digested overnight with 100 µg trypsin at 37° C. The digests were acidified, desalted using a C18 Sep-Pak cartridges (Waters) and the peptides were dried using a SpeedVac. These peptides were dissolved in 750 µl of 80% (v/v) ACN/0.1% (v/v) trifluoroacetic acid and fractionated by hydrophilic (HILIC) chromatography (8). The samples were loaded on a TSKgel Amide-80 column (TOSOH, dimension: 4.6 mm×25 cm) and the gradient developed as previously described (9). Under these conditions, the phosphopeptides eluted from the HILIC column between 20-70 min. Phosphopeptides from these samples were enriched using a standard $Fe^{3+}$-IMAC enrichment protocol (8, 9) and measured by LC-MS/MS. Samples were separated on a Proxeon Easy-nLC system (Thermo Fisher Scientific) using a 20 cm long, 75 µm internal diameter PicoFrit column (New Objective) home-packed with Magic $C_{18}$ reverse phase material (Michrom Bioresources) and the following gradient: i) 0-170 min from 2% to 35% buffer B (0.08% (v/v) formic acid, 90% (v/v) acetonitrile in water); ii) 170-187 min from 35% to 80% buffer B; iii) 187-188 min from 80% to 90% buffer B; 188-198 min isocratic at 90% buffer B; 198-199 min from 90% to 2% buffer B; 199-204 min isocratic at 2% buffer B. The composition of Buffer A was: 0.1% (v/v) formic acid, 2% (v/v) acetonitrile. The nano-LC system was online with a Thermo Fisher Scientific LTQ Orbitrap Velos instrument set to perform top-15 data-dependent CID analysis in the 350-1600 m/z range using a resolution of 60000 for the precursor scan and a minimal intensity for sequencing of 10000 counts. Monoisotopic precursor selection was used and +1 as well as unassigned charge states were excluded from sequencing. Dynamic exclusion was set to a repeat count of 2 within 30 sec, with exclusion duration of 90 sec and an exclusion mass width of 10 ppm. The data was analysed using MaxQUANT (10).

Statistical Analysis

Quantitative data are presented as the mean±SD. Statistical significance of differences between experimental groups was assessed using the Student's t test or two-way Anova with the Bonferroni posttest. Differences in means were considered significant if p<0.05. Unless otherwise indicated, the symbols represent the following *p<0.05, p<0.01, *p<0.001.

REFERENCES

1. McIver E G, et al. (2009) Preparation of pyrimidine derivatives capable of inhibiting one or more kinases. PCT. Int. Appl.: WO 2009122180 A2009122181
2. Martin M W, et al. (2006) Novel 2-aminopyrimidine carbamates as potent and orally active inhibitors of Lck: synthesis, SAR, and in vivo antiinflammatory activity. *J Med Chem* 49:4981-4991
3. Haidle A, et al. (2009) Preparation of dihydropyrrolopyrimidinone derivatives for use as MARK inhibitors. PCT Int. Appl.: WO 2009152027 A2009152021
4. Lizcano J M, et al. (2004) LKB1 is a master kinase that activates 13 kinases of the AMPK subfamily, including MARK/PAR-1. *EMBO J* 23:833-843
5. Pfaffl M W (2001) A new mathematical model for relative quantification in real-time RT-PCR. *Nucleic Acids Res* 29:e45
6. Hastie C J, McLauchlan H, & Cohen P (2006) Assay of protein kinases using radiolabeled ATP: a protocol. *Nat Protoc* 1:968-971
7. Bain J, et al. (2007) The selectivity of protein kinase inhibitors: a further update. *Biochem J* 408:297-315
8. McNulty D E & Annan R S (2008) Hydrophilic interaction chromatography reduces the complexity of the phosphoproteome and improves global phosphopeptide isolation and detection. *Mol Cell Proteomics* 7:971-980
9. Navarro M N, Goebel J, Feijoo-Carnero C, Morrice N, & Cantrell D A (2011) Phosphoproteomic analysis reveals an intrinsic pathway for the regulation of histone deacetylase 7 that controls the function of cytotoxic T lymphocytes. *Nat Immunol* 12:352-361
10. Cox J, et al. (2009) A practical guide to the MaxQuant computational platform for SILAC-based quantitative proteomics. *Nat Protoc* 4:698-705

Results

MRT67307 Increases IL-10 Production Via a CREB-CRTC3 Dependent Mechanism

Figure 2D:
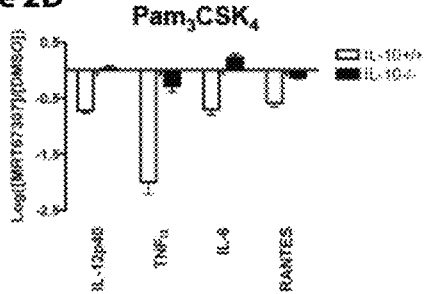
Figure 2E:
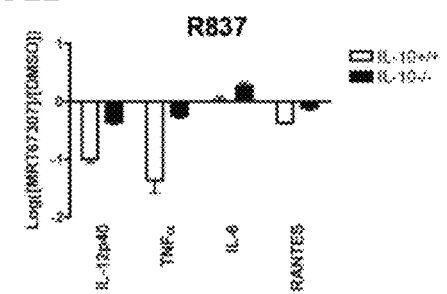
Figure 2F:
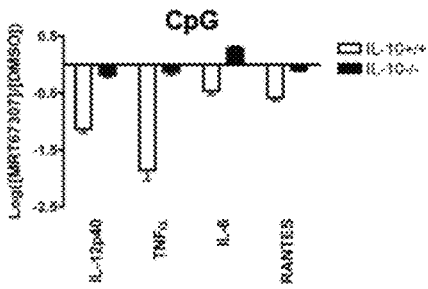
Figure 2G:
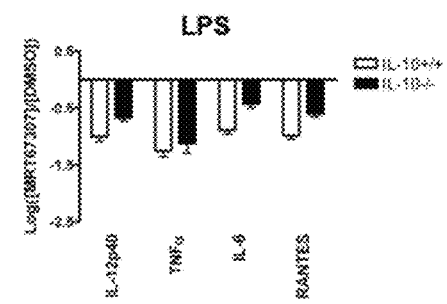

Phosphorylation of CREB at Ser133 or the closely-related ATF1 at Ser63 (FIG. 2D). However, in a phosphoproteomic study to identify proteins whose phosphorylation was suppressed by MRT67307, we found that the phosphorylation of CRTC3 was unaffected by stimulation with the TLR1/2 agonist Pam$_3$CSK$_4$, but nevertheless was robustly dephosphorylated at Ser62, Ser329 and Ser370 when macrophages were incubated with MRT67307. Similarly, phosphorylation of CRTC3 at Ser370 was unaffected by LPS stimulation but blocked by MRT67307. siRNA knockdown of CRTC3, but not CRTC1 or CRTC2, completely suppressed the effects of MRT67307 on TLR-stimulated IL-10 production in macrophages. Collectively, these results suggested that the effects of MRT67307 on CREB-dependent gene transcription, including IL-10 transcription, were mediated by the inactivation of a protein kinase leading to the dephosphorylation and activation of CRTC3 in macrophages.

Inhibition of SIKs by MRT67307, MRT199665 and HG-9-91-01 Increases IL-10 Production while Suppressing IL-6, IL-12 and TNF Secretion We found that the concentration of MRT67307 required to enhance IL-10 secretion was 20-fold higher than that needed to block the TBK/IKKε-dependent production of IFNβ by LPS. Moreover, MRT67307 could still enhance transcription of the CREB-dependent Nurr77 gene in TBK1/IKKε$^{-/-}$ fibroblasts. These observations suggested that inhibition of the IKK-related kinases did not underlie the effects of MRT67307 on CREB-dependent gene transcription and IL-10 production. We therefore examined whether members of the AMPK subfamily might be inhibited by MRT67307, which revealed that this compound inhibited the MARK, NUAK and SIK isoforms in vitro with comparable potency to the IKK-related kinases (FIG. 4A). MRT67307 did not inhibit the Brain-Specific Kinases (BRSKs) and only inhibited the Maternal Embryonic Leucine zipper Kinase (MELK) and AMPK itself more weakly.

Figure 11A:
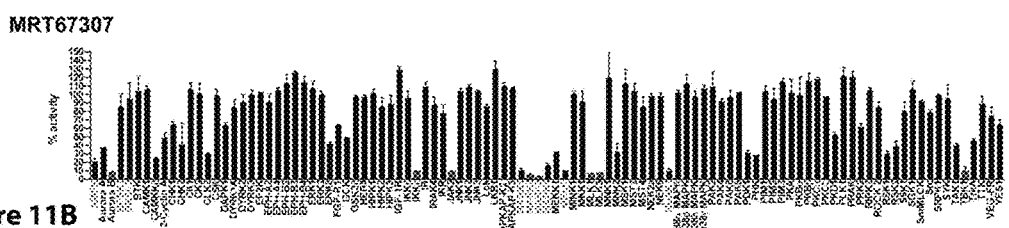
FIGS. 11A to 11D. Selectivity of MRT67307, MRT199665, KIN112 and HG-9-91-01 for different protein kinases.
Figure 11B:
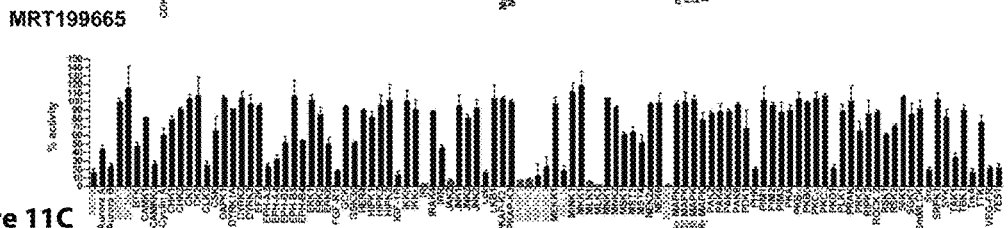
Figure 11C:
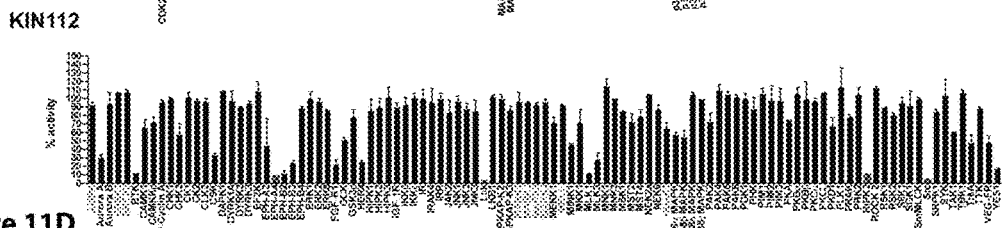
Figure 11D:
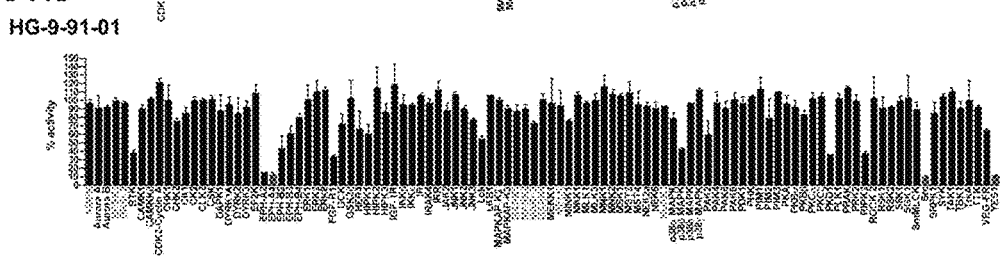
Figure 14A:
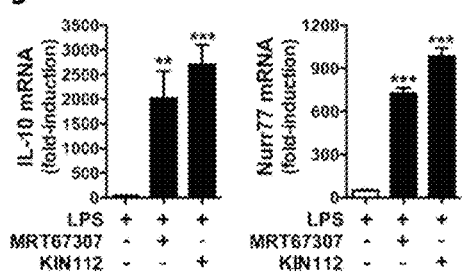
FIGS. 14A to 14D. Conservation of the effect of SIK inhibitors on IL-10 production in myeloid cells and across species.
Figure 14B:
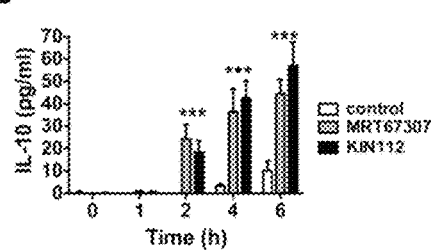
Figure 14C:
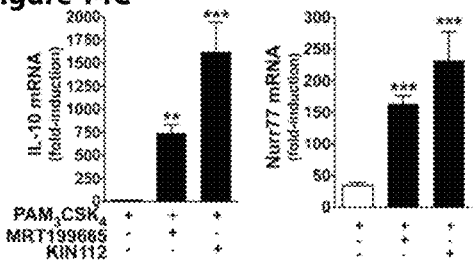
Figure 14D:
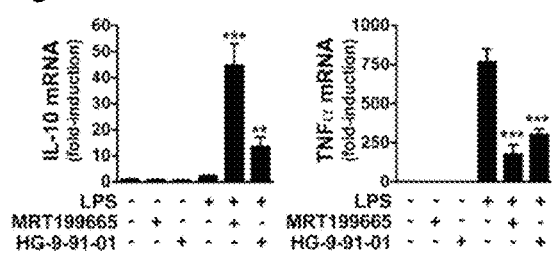

To investigate whether and which AMPK family member might be regulating CREB-dependent gene transcription and IL-10 production, we exploited additional pharmacological inhibitors with specificities that were distinct from MRT67307. MRT199665, a potent inhibitor of most AMPK-related kinases, which does not inhibit the IKK-related kinases (FIG. 11A), increased LPS-stimulated IL-10 mRNA and Nurr77 mRNA production, as well as IL-10 secretion (FIG. 11B), further supporting the view that inhibition of AMPK-related kinases, and not the IKK-related kinases, drives IL-10 production. The SIKs are unique among the AMPK-related kinases in possessing a small amino acid residue (threonine) at the "gatekeeper" site. We therefore examined KIN112 and, subsequently, a much more potent analogue HG-9-91-01, which not only target the ATP-binding site, but also a small hydrophobic pocket adjacent to this site that is created by the presence of a small amino acid residue at this 'gatekeeper' site. KIN112 and HG-9-91-01 inhibited a number of protein tyrosine kinases that possess a threonine residue at the 'gatekeeper' site, such as Src family members (Src, Lck and Yes), BTK, and the FGF and Ephrin receptors (FIGS. 11C and 11D). However, they also potently inhibited the SIKs and, crucially, did not inhibit any other member of the AMPK-related kinase subfamily (FIG. 11A), which all possess a large hydrophobic residue (Met or Leu) at the 'gatekeeper' site. Like MRT67307 and MRT199665, HG-9-91-01 and KIN112 increased LPS-stimulated IL-10 production and greatly suppressed pro-inflammatory cytokine secretion (FIG. 11C and FIGS. 12A to 12B), even when cells were co-stimulated with IFNγ to generate fully polarized classically-activated (M1) macrophages (FIG. 12C). Moreover, CRTC3 was required for HG-9-91-01 to elevate IL-10 production in LPS-stimulated primary mouse macrophages (FIG. 13). SIK inhibitors also enhanced CREB-dependent gene transcription and IL-10 production in bone marrow-derived dendritic cells (FIGS. 14A and 14B), human THP-1 cells and human primary macrophages (FIGS. 14C and 14D). Taken together, these results indicate that the SIK-CRTC3 signaling pathway and its role in regulating IL-10 production is present in different cells of the myeloid lineage and conserved in man.

Figure 8A:
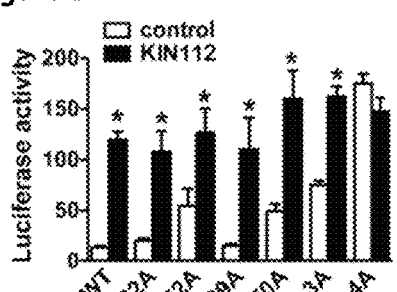
FIGS. 8A to 8G. Dephosphorylation of CRTC3 at Ser62, Ser162, Ser329 and Ser370 leads to dissociation from 14-3-3 proteins, nuclear translocation and activation of CREB-dependent gene transcription.
Figure 8C:
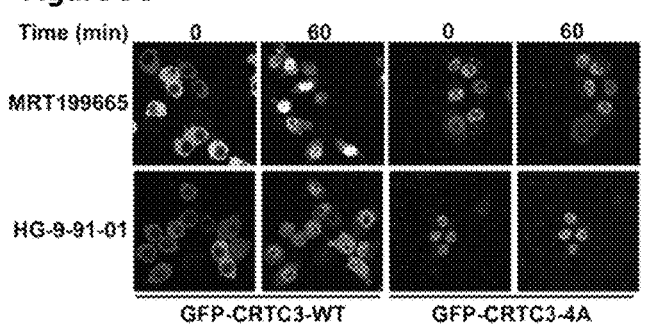
Figure 8B:
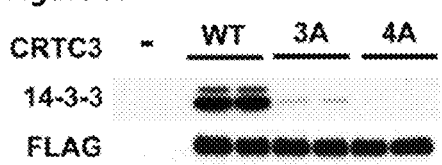
Figure 15A:
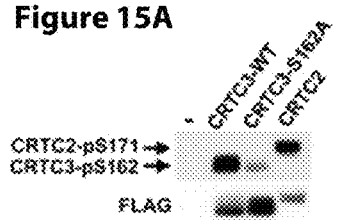
FIGS. 15A to 15C. SIK inhibitors induce the dephosphorylation of CRTC3 at Ser62, Ser162, Ser329 and Ser370 and its translocation to the nucleus.
Figure 15B:
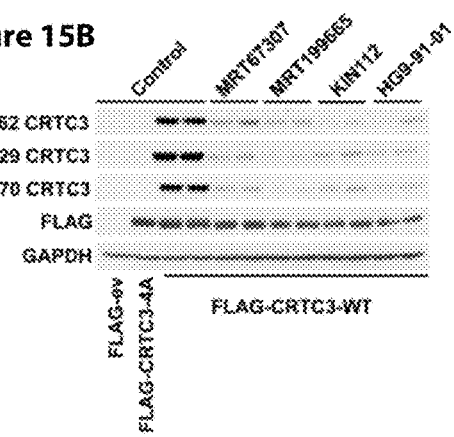

SIKs Phosphorylate CRTC3 at Ser62, Ser162, Ser329 and Ser370 to Regulate 14-3-3 Protein Binding, Nuclear Transport and CREB Co-Activator Function To address the regulation of CRTC3 in macrophages, we mapped the key phosphorylation sites on this protein. Although we detected phosphorylation of CRTC3 at Ser62, Ser329 and Ser370 that was blocked by MRT67307 and the mutation of these three sites to Ala increased CREB-dependent luciferase reporter gene expression, the inclusion of SIK inhibitors still produced a further increase in luciferase activity induced by the CRTC3[S62A/S329A/S370A] mutant (FIG. 8A). This suggested the existence of an additional phosphorylation site(s). Ser171 is thought to be a key regulatory phosphorylation site in CRTC2 (14) and corresponds to Ser162 in CRTC3. We found that Ser162 was phosphorylated when CRTC3 was overexpressed, which was lost when the cells were treated with SIK inhibitors (FIG. 15B). Moreover, the further mutation of Ser162 to Ala to create the CRTC3[S62A/S162A/S329A/S370A] mutant completely abolished the interaction of CRTC3 with 14-3-3 proteins, led to persistent nuclear localization and, as a consequence, induced maximal activation of CRTC3 in a CREB-luciferase assay, which was insensitive to SIK inhibitors (FIGS. 8A to 8C). These results identify Ser62, Ser162, Ser329 and Ser370 as four of the key phosphorylation sites suppressing CRTC3 function.

Figure 8E:
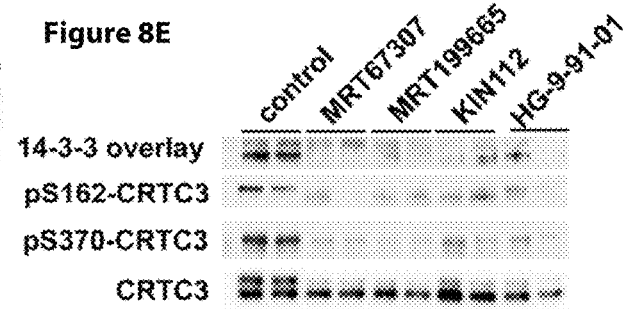
Figure 8D:
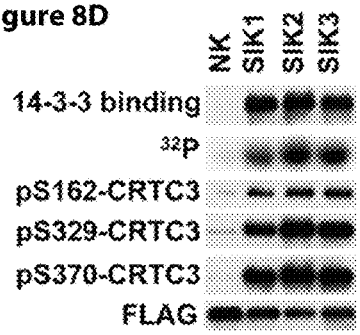
Figure 8F:
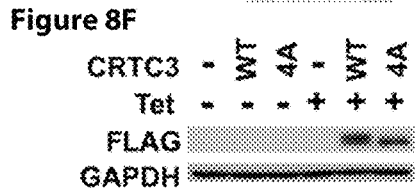
Figure 8G:
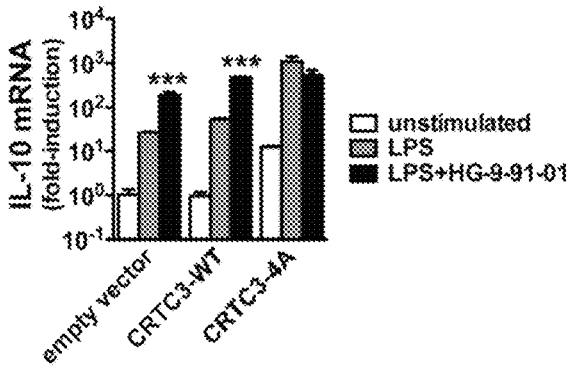
Figure 15C:
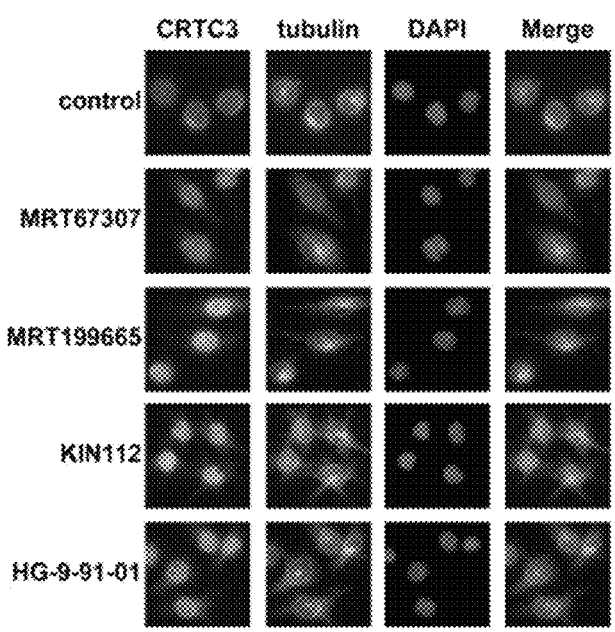

We also found that purified preparations of SIK1, SIK2 and SIK3 phosphorylated CRTC3 at Ser162, Ser329 and Ser370 in vitro leading to an interaction with 14-3-3 proteins (FIG. 8D). Moreover, the phosphorylation of these sites and 14-3-3 binding to SIKs could be blocked and nuclear translocation enhanced by any of the SIK inhibitors (FIGS. 8E and 15C). Finally, expression of the constitutively active mutant CRTC3[S62A/S162A/S329A/S370A] led to an increase in TLR-stimulated IL-10 production in macrophages which could not be increased further by SIK inhibition (FIGS. 8F and 8G).

Genetic Evidence that Inhibition of SIKs Induces IL-10 Production

Figure 9A:
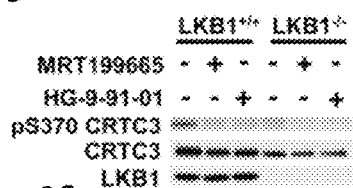
Figure 9B:
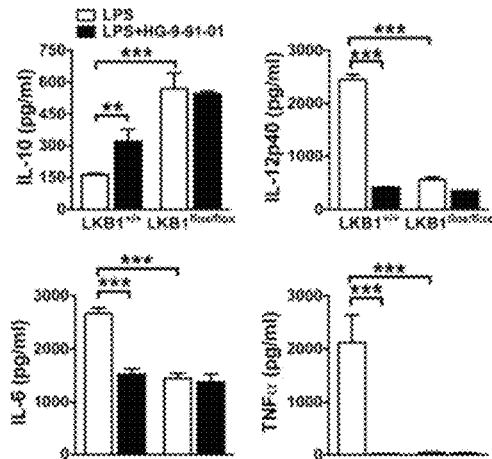

To obtain further evidence that inhibition of the SIKs underlies the ability of MRT67307, MRT199665, KIN112 and HG-9-91-01 to stimulate IL-10 production and suppress pro-inflammatory cytokine production, we investigated the effect of these compounds in LKB1$^{-/-}$ macrophages. All members of the AMPK-subfamily, apart from MELK, are only active if they are phosphorylated by the protein kinase LKB1 (17). The activity of SIKs should therefore be low in LKB1$^{-/-}$ cells and these cells should phenocopy the effects of SIK inhibitors. As predicted, CRTC3 phosphorylation at Ser370 was indeed greatly reduced in LKB1$^{-/-}$ cells, indicating that the activity of SIKs was low (FIG. 9A). Moreover, LKB1$^{-/-}$ macrophages secreted higher levels of IL-10 and greatly reduced levels of IL-12 and TNFα in response to LPS, which were unaffected by HG-9-91-01 (FIG. 9B).

Figure 16A:
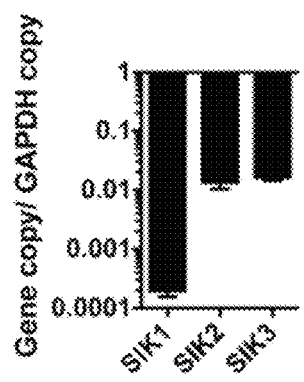
FIGS. 16A to 16D. shRNA knockdown of SIKs sensitizes macrophages to HG-9-91-01.
Figure 16B:
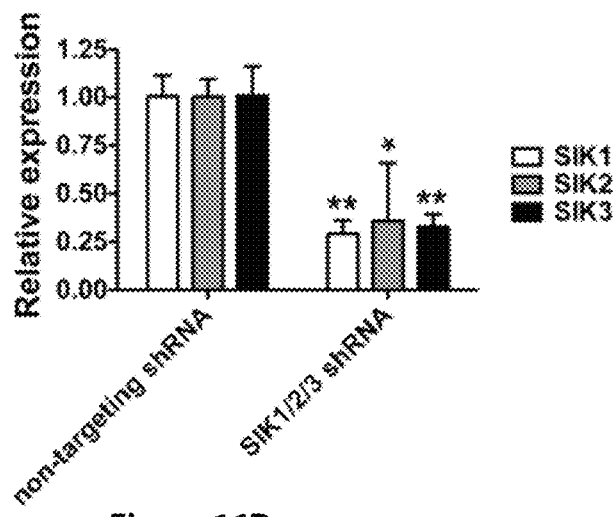
Figure 16C:
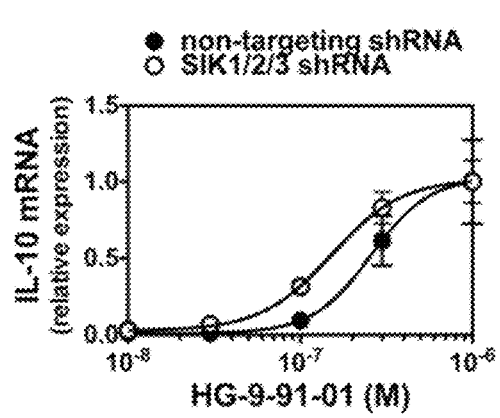
Figure 16D:
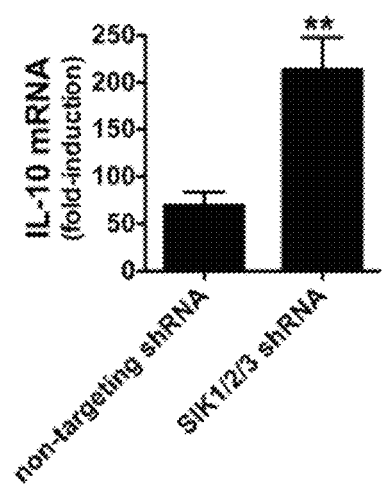

Quiescent macrophages express all three SIK isoforms with SIK2 and SIK3 mRNA being expressed at much higher levels than SIK1 mRNA. We used RNA interference to knockdown the expression of all three SIK isoforms in macrophages (FIG. 16B). Reduced expression of SIK1, SIK2 and SIK3 consistently sensitized macrophages to HG-9-91-01 (FIG. 16C), with suboptimal concentrations of HG-9-91-01 inducing a 4-fold higher expression of IL-10 mRNA in SIK-depleted macrophages compared to wild-type (WT) macrophages (FIG. 16D).

Figure 9C:
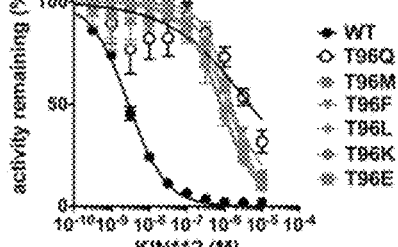

The most stringent experiment that can be carried out to establish that the effects of a pharmacological inhibitor are mediated via the inhibition of the presumed target, and not by an "off target" effect, is to show that the effects of the compound disappear when the WT enzyme is replaced by a drug-resistant mutant (15, 18, 19). As mentioned above, the compounds KIN112 and HG-9-91-01 inhibit SIKs and not other members of the AMPK subfamily because they target a hydrophobic pocket created by the presence of a small amino acid residue at the "gatekeeper" site (FIG. 9C).

Figure 9D:
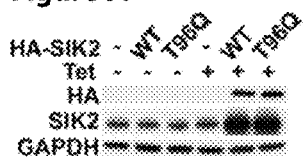
Figure 9E:
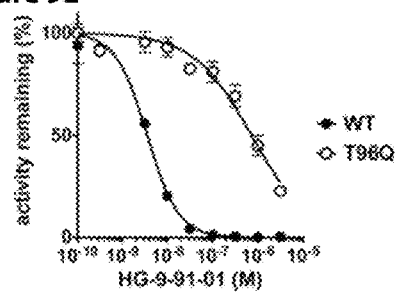
Figure 9G:
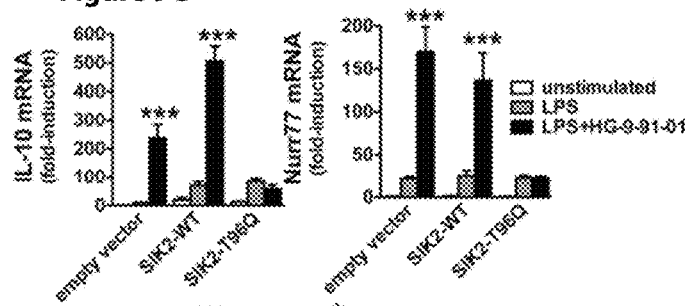
Figure 9H:
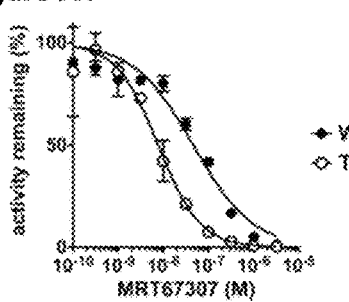
Figure 9I:
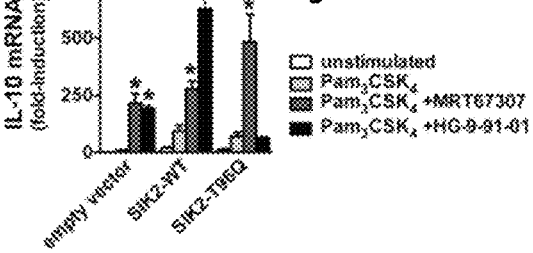

Mutation of the gatekeeper threonine to an amino acid residue with a larger side chain renders the SIKs 100-1000-fold less sensitive to KIN112 and HG-9-91-01, with mutation to glutamine generating the most drug-resistant mutant (FIGS. 9D and 9E). When RAW264.7 macrophages were generated to inducibly express the SIK2[T96Q] mutant (FIG. 9F), the LPS-stimulated production of IL-10 mRNA could no longer be enhanced by HG-9-91-01 (FIG. 9G). In contrast, HG-9-91-01 continued to greatly enhance LPS-stimulated IL-10 mRNA production when WT SIK2 was expressed to the same level (FIGS. 9F and 9G). The same results were obtained when the mRNA encoding another CREB-dependent gene (Nurr77) was studied instead of IL-10 (FIG. 9G). In contrast to KIN112 and HG-9-91-01, MRT67307 potently inhibits members of the AMPK subfamily with bulky amino acids at the gatekeeper site. Notably, MRT67307 inhibited the SIK2[T96Q] mutant more potently than the WT enzyme (FIG. 9H) and therefore still increased Pam$_3$CSK$_4$-stimulated IL-10 production in macrophages expressing the SIK2[T96Q] mutant (FIG. 9I). Collectively, these genetic studies prove that HG-9-91-01 exerts its effects by inhibiting SIKs and not another target, but further studies are needed to establish whether SIK2, or another SIK isoform(s) mediates these effects on macrophage biology.

Figure 10A:
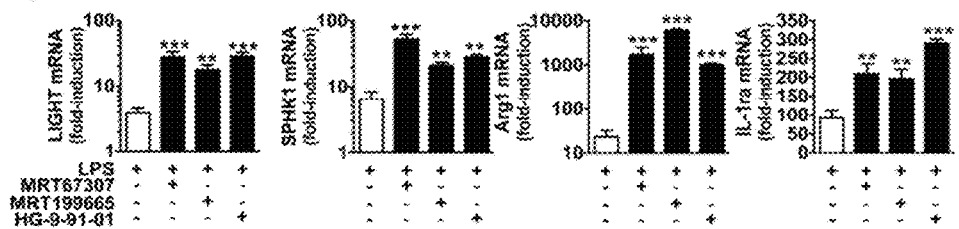
FIGS. 10A to 10E. Inhibition of the LKB1-SIK-CRTC3-IL10 signaling axis drives the expression of markers of regulatory macrophages.
Figure 10B:
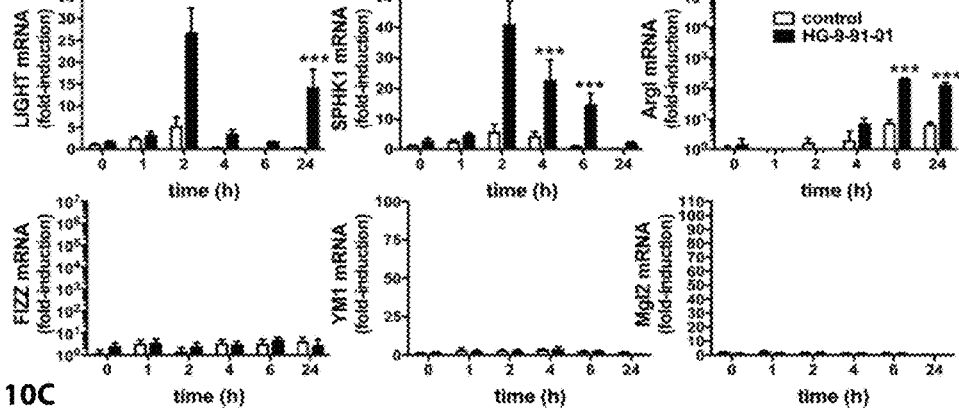
Figure 10C:
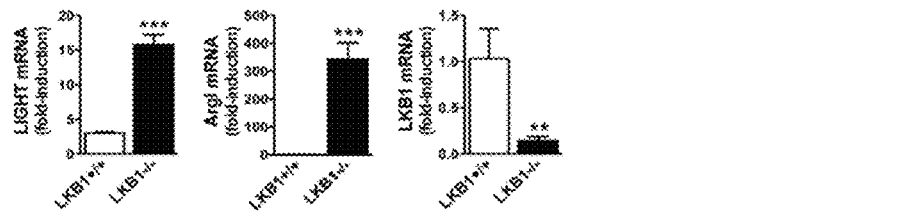
Figure 10D:
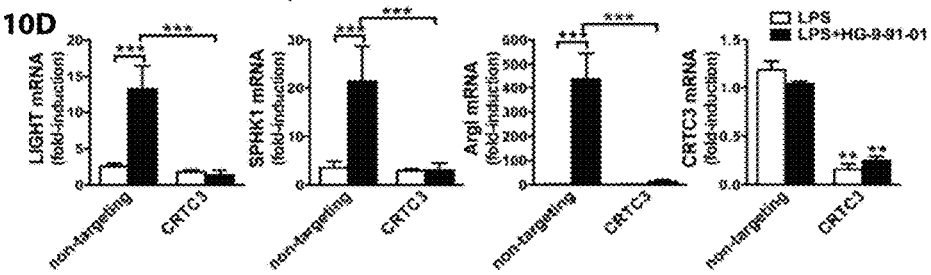
Figure 10E:
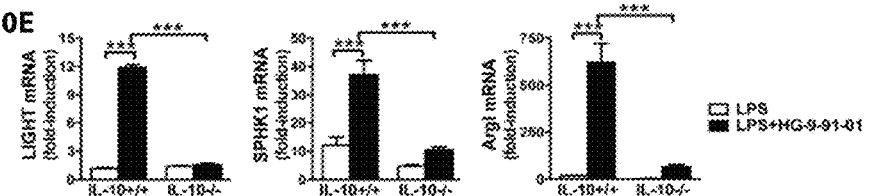

Inhibition of SIKs Induces the Expression of Regulatory Macrophage Markers Via a CRTC3-IL-10 Pathway Strikingly, we found that treatment of quiescent macrophages with SIK inhibitors, did not just enhance TLR agonist-stimulated IL-10 production, but also switched their gene expression program from the classically-activated (M1) route towards the regulatory (M2b) phenotype. In particular, production of other mRNAs including SPHK1, LIGHT and Arginase 1 that encode characteristic markers of regulatory macrophages was increased (FIG. 10A). In contrast, inhibition of SIKs had no effect on the expression of FIZZ, Ym1 or Mgl2 (FIG. 10B), which are markers of wound-healing (M2a) macrophages. In contrast, control experiments showed that, as expected, IL-4 induced the expression of FIZZ, Ym1 or Mgl2 but not LIGHT or SPHK1. Expression of the markers of regulatory macrophages was also enhanced in LKB1$^{-/-}$ macrophages after stimulation with LPS (FIG. 10C). The ability of HG-9-91-01 to increase the LPS-stimulated expression of SPHK1, LIGHT and Arginase 1 did not occur in cells treated with CRTC3 siRNA oligonucleotides and was greatly reduced in IL-10$^{-/-}$ macrophages (FIGS. 10D and 10E). Thus, the IL-10 produced by inhibition of the LKB1-SIK-CRTC3 signaling axis reinforces the anti-inflammatory phenotype of macrophages by inducing a gene transcription program associated with regulatory macrophages. Finally, LPS-stimulated transcription and secretion of the anti-inflammatory molecule IL-1 receptor antagonist (IL-1ra) was also increased by pharmacological inhibition of SIKs (FIG. 10A). Thus, inhibition of the SIKs drives the gene expression program of regulatory macrophages.

The invention claimed is:

1. A method of treating Crohn's disease or discoid lupus in a subject in need thereof comprising administering to the subject in need thereof a therapeutically effective amount of a compound, or a pharmaceutically acceptable salt or solvate thereof, wherein the compound is of Formula (X):

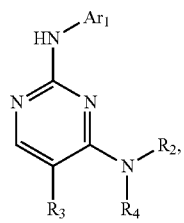

wherein:
Ar$_1$ is a 5- or 6-membered, hetero- or homo-cyclic, aromatic ring substituted with saturated heterocyclic or methylene-heterocyclic;
R$_2$ is

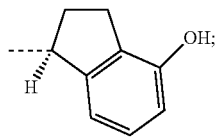

R$_3$ is hydrogen or

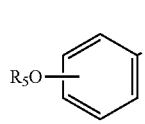

and
R$_4$ is hydrogen,

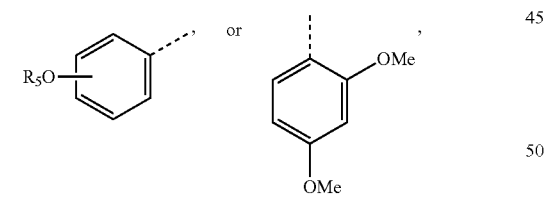

wherein R$_5$ is hydrogen or C$_1$-C$_4$ alkyl;
or R$_3$ and R$_4$ together form a pyrrolidine ring, wherein one or both of the free carbon atoms of the pyrrolidine ring are substituted with an alkyl;
or R$_3$ and R$_4$ together form

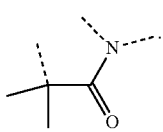

2. The method of claim 1, wherein R$_4$ is hydrogen or

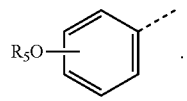

3. A method of treating a disease in a subject in need thereof comprising administering to the subject in need thereof a therapeutically effective amount of a compound, or a pharmaceutically acceptable salt or solvate thereof, wherein the disease is Crohn's disease or discoid lupus, and the compound is of Formula (II):

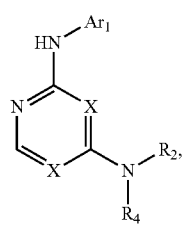

wherein:
Ar$_1$ is a 5- or 6-membered, hetero- or homo-cyclic, aromatic ring, optionally substituted with C$_1$-C$_4$ alkyl, saturated heterocyclic, or -methylene-heterocyclic;
one instance of X is N, and the other instance of X is CH;
R$_2$ is

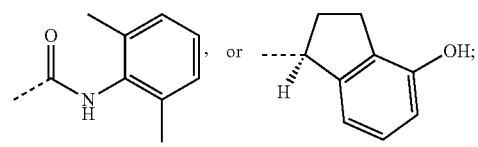

and
R$_4$ is hydrogen,

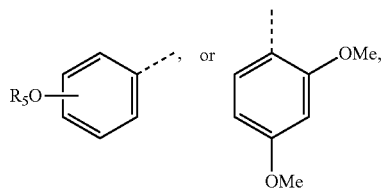

wherein R$_5$ is hydrogen or C$_1$-C$_4$ alkyl.

4. The method of claim 3, wherein:
Ar$_1$ is

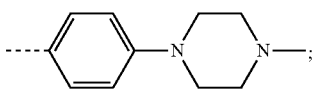

$R_2$ is

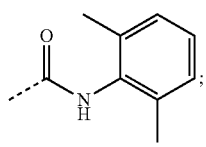

and $R_4$ is

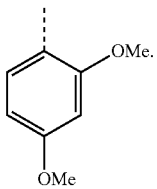

5. The method of claim 1, wherein the compound is of the formula:

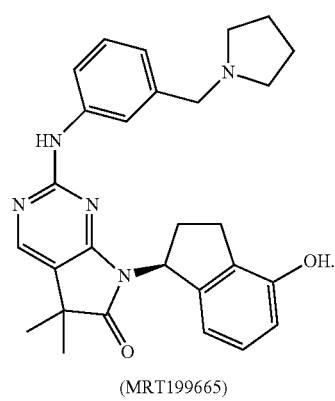 [SMILES: CC1(C)C(=O)N([C@H]2CCc3c(O)cccc32)c2nc(Nc3cccc(CN4CCCC4)c3)ncc21]
(MRT199665)

6. The method of claim 3, wherein the compound, or pharmaceutically acceptable salt or solvate thereof, is administered in an encapsulated form.

7. A method of treating Crohn's disease in a subject in need thereof comprising administering to the subject in need thereof a therapeutically effective amount of a compound of the formula:

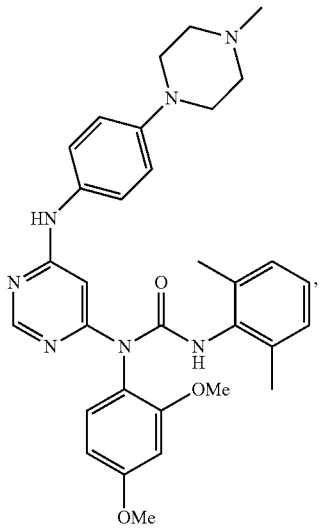 [SMILES: COc1ccc(N(C(=O)Nc2c(C)cccc2C)c2cc(Nc3ccc(N4CCN(C)CC4)cc3)ncn2)c(OC)c1]

or a pharmaceutically acceptable salt or solvate thereof.

8. The method of claim 3, wherein $Ar_1$ is a benzene ring, optionally substituted with $C_1$-$C_4$ alkyl, saturated heterocyclic, or -methylene-heterocyclic.

9. The method of claim 3, wherein $Ar_1$ is a benzene ring substituted with saturated heterocyclic.

10. The method of claim 3, wherein $Ar_1$ is

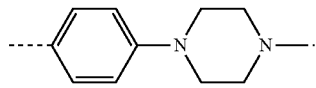

11. The method of claim 3, wherein $Ar_1$ is

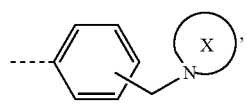

wherein

is 5- or 6-membered heterocyclyl comprising up to one oxygen atom in the heterocyclic ring system.

12. The method of claim 3, wherein $Ar_1$ is a 5- or 6-membered, heterocyclic aromatic ring, optionally substituted with $C_1$-$C_4$ alkyl, saturated heterocyclic, or -methylene-heterocyclic.

13. The method of claim 3, wherein $Ar_1$ is

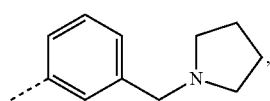

-continued

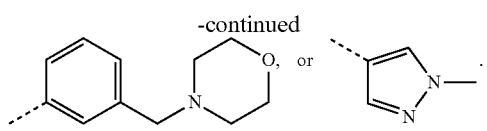

14. The method of claim 3, wherein the compound is of the formula:

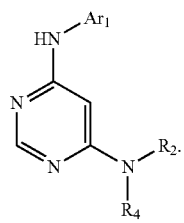

15. The method of claim 3, wherein the compound is of the formula:

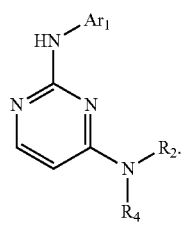

16. The method of claim 3, wherein $R_4$ is

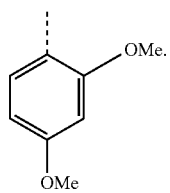

17. The method of claim 3, wherein $R_4$ is hydrogen or

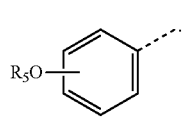

18. The method of claim 3, wherein the compound, or pharmaceutically acceptable salt or solvate thereof, is administered in the form of a liposome.

19. The method of claim 3, wherein the therapeutically effective amount is effective for inhibiting a salt inducible kinase (SIK).

20. The method of claim 3, wherein the therapeutically effective amount is effective for increasing the formation of macrophages with a regulatory phenotype.

21. The method of claim 3, wherein $R_2$ is

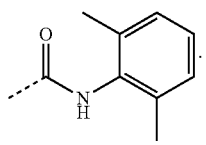

22. The method of claim 3, wherein the disease is Crohn's disease.

23. The method of claim 3, wherein the disease is discoid lupus.

24. A method of treating discoid lupus in a subject in need thereof comprising administering to the subject in need thereof a therapeutically effective amount of a compound of the formula:

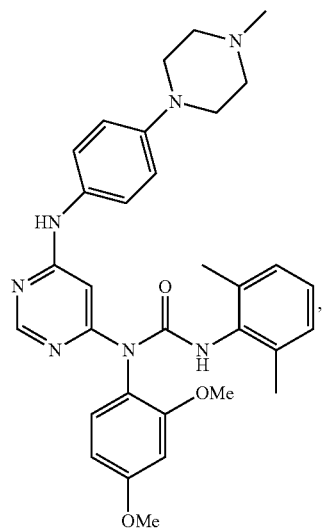 [SMILES: COc1ccc(N(C(=O)Nc2c(C)cccc2C)c2cc(Nc3ccc(N4CCN(C)CC4)cc3)ncn2)c(OC)c1]

or a pharmaceutically acceptable salt or solvate thereof.

25. The method of claim 1, wherein $Ar_1$ is a benzene ring substituted with saturated heterocyclic or -methylene-heterocyclic.

26. The method of claim 1, wherein $Ar_1$ is

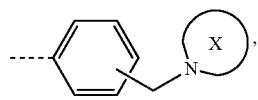

wherein

is 5- or 6-membered heterocyclyl comprising up to one oxygen atom in the heterocyclic ring system.

* * * * *

SEQUENCE LISTING

<160> NUMBER OF SEQ ID NOS: 52

<210> SEQ ID NO 1
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 1
ccctttgcta tggtgtcctt tc                                                22

<210> SEQ ID NO 2
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 2
gatctccctg gtttctcttc cc                                                22

<210> SEQ ID NO 3
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 3
ctactgtgtt cctggcaata gc                                                22

<210> SEQ ID NO 4
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 4
aacattgacg ctgaaggact ac                                                22

<210> SEQ ID NO 5
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 5
gaagagagcg gacaaggaga tc                                                22

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 6
aaggcatggc ttcagcagag                                                   20

<210> SEQ ID NO 7
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 7
cctgttgcta gagtctgcct tc                                                22

<210> SEQ ID NO 8

```
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 8
caatccaatc accaaagcca cg                                              22

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 9
gtaacccgtt gaaccccatt                                                 20

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 10
ccatccaatc ggtagtagcg                                                 20

<210> SEQ ID NO 11
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 11
tcctttatac acagcaagtc tc                                              22

<210> SEQ ID NO 12
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 12
ttctgaaggc ttgcatcttg                                                 20

<210> SEQ ID NO 13
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 13
acagcagtgt gcagttgatg a                                               21

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 14
```
ggcagtcatg tccggtgatg                                        20

<210> SEQ ID NO 15
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 15
ctgcatcaac gtcttggaga                                        20

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 16
gatacgtcaa gcccctcaag                                        20

<210> SEQ ID NO 17
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 17
ctccaagcca aagtccttag ag                                     22

<210> SEQ ID NO 18
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 18
aggagctgtc attagggaca tc                                     22

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 19
cccaggatgc caactttgaa                                        20

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 20
ggcccatctg ttcatagtct                                        20

<210> SEQ ID NO 21
<211> LENGTH: 21
<212> TYPE: DNA

```
<213> ORGANISM: Artificial Sequence
<220> FEATURE:
<223> OTHER INFORMATION: Synthetic Oligonucleotide

<400> SEQUENCE: 21
ttagccaatg tgcttagctg g                                              21

<210> SEQ ID NO 22
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 22
ggcctccaat tcttgaaacc t                                              21

<210> SEQ ID NO 23
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 23
agaagggagt tcaaacctg gt                                              22

<210> SEQ ID NO 24
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 24
gtcttgctca tgtgtgtaag tga                                            23

<210> SEQ ID NO 25
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 25
acagcaccac tcttctaccg c                                              21

<210> SEQ ID NO 26
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 26
tcacagggag caagcacata gg                                             22

<210> SEQ ID NO 27
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 27
ttaatgagca ggttcttc                                                  18
```

<210> SEQ ID NO 28
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 28
aaataaatgg cagcaaag                                                 18

<210> SEQ ID NO 29
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 29
caggttaata gcggagtg                                                 18

<210> SEQ ID NO 30
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 30
atagccaaga ggacatca                                                 18

<210> SEQ ID NO 31
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 31
actcaaagaa ggcgggttcc                                               20

<210> SEQ ID NO 32
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 32
tgggtggcag ggatcagg                                                 18

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 33
tgcgactggc ttatacaagg                                               20

<210> SEQ ID NO 34
<211> LENGTH: 20
<212> TYPE: DNA
<213> ORGANISM: Artificial Sequence
<220> FEATURE:

<223> OTHER INFORMATION: Synthetic Oligonucleotide

<400> SEQUENCE: 34
gagtgctccg agatgaatcc                                               20

<210> SEQ ID NO 35
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 35
agccatcact tcatcaagc                                                19

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
attcccatca aactgtctcc                                               20

<210> SEQ ID NO 37
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 37
gccttccgtg ttcctaccc                                                19

<210> SEQ ID NO 38
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 38
tgcctgcttc accaccttc                                                19

<210> SEQ ID NO 39
<211> LENGTH: 21
<212> TYPE: DNA
<213> ORGANISM: Homo sapiens

<400> SEQUENCE: 39
accttattgt acctctctta t                                             21

<210> SEQ ID NO 40
<211> LENGTH: 18
<212> TYPE: DNA
<213> ORGANISM: Homo sapiens

<400> SEQUENCE: 40
gggcttcttt ctaaatcg                                                 18

<210> SEQ ID NO 41
<211> LENGTH: 17
<212> TYPE: DNA
<213> ORGANISM: Homo sapiens

```
<400> SEQUENCE: 41
catccaacct tcccaaa                                                    17

<210> SEQ ID NO 42
<211> LENGTH: 17
<212> TYPE: DNA
<213> ORGANISM: Homo sapiens

<400> SEQUENCE: 42
ggtggtcttg ttgctta                                                    17

<210> SEQ ID NO 43
<211> LENGTH: 17
<212> TYPE: DNA
<213> ORGANISM: Homo sapiens

<400> SEQUENCE: 43
ggagagtttg acacctt                                                    17

<210> SEQ ID NO 44
<211> LENGTH: 17
<212> TYPE: DNA
<213> ORGANISM: Homo sapiens

<400> SEQUENCE: 44
tacacctgga agtcctc                                                    17

<210> SEQ ID NO 45
<211> LENGTH: 20
<212> TYPE: DNA
<213> ORGANISM: Homo sapiens

<400> SEQUENCE: 45
ttaactctgg taaagtggat                                                 20

<210> SEQ ID NO 46
<211> LENGTH: 18
<212> TYPE: DNA
<213> ORGANISM: Homo sapiens

<400> SEQUENCE: 46
acttgatttt ggagggat                                                   18

<210> SEQ ID NO 47
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 47
ggaaaagcaa gaggaaagat tgac                                            24

<210> SEQ ID NO 48
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 48
ccaccatcca ggcgtagc                                                   18
```

```
<210> SEQ ID NO 49
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 49

Ala Leu Asn Arg Thr Ser Ser Asp Ser Ala Leu His Arg Arg Arg
1               5                   10                  15

<210> SEQ ID NO 50
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 50

Cys Trp Lys Glu Glu Lys His Pro Gly Phe Arg
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (7)..(7)
<223> OTHER INFORMATION: PHOSPHORYLATION

<400> SEQUENCE: 51

Gly Leu Gln Ser Ser Arg Ser Asn Pro Ser Ile Gln
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (6)..(6)
<223> OTHER INFORMATION: PHOSPHORYLATION

<400> SEQUENCE: 52

Arg Leu Phe Ser Leu Ser Asn Pro Ser Leu Ser Thr
1               5                   10
```